US011254932B2

(12) United States Patent
Short et al.

(10) Patent No.: US 11,254,932 B2
(45) Date of Patent: Feb. 22, 2022

(54) CONDITIONALLY ACTIVE BIOLOGICAL PROTEINS

(71) Applicant: BIOATLA, LLC, San Diego, CA (US)

(72) Inventors: Jay M. Short, Del Mar, CA (US); Hwai Wen Chang, San Marcos, CA (US); Gerhard Frey, San Diego, CA (US)

(73) Assignee: BioAtla, Inc., San Diego, CA (US)

( * ) Notice: Subject to any disclaimer, the term of this patent is extended or adjusted under 35 U.S.C. 154(b) by 59 days.

(21) Appl. No.: 16/733,358

(22) Filed: Jan. 3, 2020

(65) Prior Publication Data
US 2020/0199578 A1  Jun. 25, 2020

Related U.S. Application Data

(63) Continuation of application No. 15/546,883, filed as application No. PCT/US2016/019242 on Feb. 24, 2016, now Pat. No. 10,563,194.
(Continued)

(51) Int. Cl.
C40B 30/04 (2006.01)
C12N 15/10 (2006.01)
(Continued)

(52) U.S. Cl.
CPC .......... C12N 15/1058 (2013.01); C07K 16/00 (2013.01); C07K 16/005 (2013.01); C07K 16/2803 (2013.01); C07K 16/2809 (2013.01); C07K 16/30 (2013.01); C12N 15/1093 (2013.01); C40B 40/08 (2013.01);
(Continued)

(58) Field of Classification Search
None
See application file for complete search history.

(56) References Cited

U.S. PATENT DOCUMENTS 4,946,778 A   8/1990 Ladner et al.
5,143,854 A   9/1992 Pirrung et al.
(Continued)

FOREIGN PATENT DOCUMENTS

WO   WO9617958 A1   6/1996
WO   WO9733899 A1   9/1997
(Continued)

OTHER PUBLICATIONS

Communication pursuant to Article 94(3) EPC for corresponding European application No. 18862643.0; dated Jan. 27, 2020 (5 pages).
(Continued)

Primary Examiner — Christian C Boesen
(74) Attorney, Agent, or Firm — Mendelsohn Dunleavy, P.C.

(57) ABSTRACT

Methods of generating conditionally active biologic proteins, in particular therapeutic or diagnostic proteins, which are more active at an aberrant condition than at a normal physiological condition. The methods include discovery methods using libraries of proteins and assays employing physiological concentrations of components of bodily fluids. The conditionally active biologic proteins may be further evolved, conjugated to other molecules, masked, reduced in activity by attaching a cleavable moiety. Criteria for selecting starting proteins for the discovery methods, as well as formats of the proteins are also disclosed.

32 Claims, 1 Drawing Sheet
Specification includes a Sequence Listing.

Related U.S. Application Data

(60) Provisional application No. 62/249,907, filed on Nov. 2, 2015, provisional application No. 62/120,312, filed on Feb. 24, 2015.

(51) Int. Cl.

| | | |
|---|---|---|
| *C07K 16/00* | (2006.01) | |
| *C40B 40/08* | (2006.01) | |
| *C40B 40/10* | (2006.01) | |
| *C07K 16/28* | (2006.01) | |
| *C07K 16/30* | (2006.01) | |

(52) U.S. Cl.
CPC .......... *C40B 40/10* (2013.01); *C07K 2317/14* (2013.01); *C07K 2317/31* (2013.01); *C07K 2317/56* (2013.01); *C07K 2317/90* (2013.01); *C07K 2317/94* (2013.01); *C40B 30/04* (2013.01)

(56) References Cited

U.S. PATENT DOCUMENTS

| | | |
|---|---|---|
| 5,208,020 A | 5/1993 | Chari et al. |
| 5,434,049 A | 7/1995 | Okano et al. |
| 5,556,752 A | 9/1996 | Lockhart et al. |
| 5,632,957 A | 5/1997 | Heller et al. |
| 5,700,637 A | 12/1997 | Southern |
| 5,744,305 A | 4/1998 | Fodor et al. |
| 5,770,456 A | 6/1998 | Holmes |
| 5,800,992 A | 9/1998 | Fodor et al. |
| 5,807,522 A | 9/1998 | Brown et al. |
| 5,830,645 A | 11/1998 | Pinked et al. |
| 5,856,174 A | 1/1999 | Lipshutz et al. |
| 5,959,098 A | 9/1999 | Goldberg et al. |
| 5,965,452 A | 10/1999 | Kovacs |
| 6,013,440 A | 1/2000 | Lipshutz et al. |
| 6,022,963 A | 2/2000 | McGall et al. |
| 6,045,996 A | 4/2000 | Cronin et al. |
| 6,048,695 A | 4/2000 | Bradley et al. |
| 6,054,270 A | 4/2000 | Southern |
| 6,258,606 B1 | 7/2001 | Kovacs |
| 6,261,776 B1 | 7/2001 | Pirrung et al. |
| 6,277,489 B1 | 8/2001 | Abbott et al. |
| 6,277,628 B1 | 8/2001 | Johann et al. |
| 6,723,538 B2 | 4/2004 | Mack et al. |
| 7,112,324 B1 | 9/2006 | Dorken et al. |
| 7,235,641 B2 | 6/2007 | Kufer et al. |
| 7,527,804 B2 | 5/2009 | Narhi et al. |
| 7,575,923 B2 | 8/2009 | Dorken et al. |
| 7,635,472 B2 | 12/2009 | Kufer et al. |
| 7,820,166 B2 | 10/2010 | Lanzavecchia |
| 7,919,089 B2 | 4/2011 | Kufer et al. |
| 8,007,796 B2 | 8/2011 | Baeuerle et al. |
| 8,709,755 B2 | 4/2014 | Short et al. |
| 8,859,467 B2 | 10/2014 | Short |
| 9,637,734 B2 | 5/2017 | Short et al. |
| 10,024,867 B2 | 7/2018 | Igawa et al. |
| 2001/0008765 A1 | 7/2001 | Shinoki et al. |
| 2001/0012537 A1 | 8/2001 | Anderson et al. |
| 2001/0014448 A1 | 8/2001 | Chappa et al. |
| 2001/0014449 A1 | 8/2001 | Nerenberg et al. |
| 2001/0016322 A1 | 8/2001 | Caren et al. |
| 2001/0018642 A1 | 8/2001 | Balaban et al. |
| 2001/0019827 A1 | 9/2001 | Dawson et al. |
| 2002/0004587 A1 | 1/2002 | Miller et al. |
| 2006/0141456 A1 | 6/2006 | Edwards et al. |
| 2008/0044413 A1 | 2/2008 | Hammond et al. |
| 2008/0213256 A1 | 9/2008 | Kufer et al. |
| 2009/0035836 A1 | 2/2009 | Datta et al. |
| 2009/0130718 A1 | 5/2009 | Short |
| 2009/0226432 A1 | 9/2009 | Lutterbuse et al. |
| 2009/0252683 A1 | 10/2009 | Kischel et al. |
| 2010/0183615 A1 | 7/2010 | Kufer et al. |
| 2010/0260739 A1 | 10/2010 | Short et al. |
| 2010/0330635 A1 | 12/2010 | Burgard et al. |
| 2011/0294178 A1 | 12/2011 | Soucaille et al. |
| 2012/0108455 A1 | 5/2012 | Kodandapani et al. |
| 2012/0164127 A1 | 6/2012 | Short et al. |
| 2012/0329113 A1 | 12/2012 | Burgard et al. |
| 2014/0024810 A1 | 1/2014 | Stagliano et al. |
| 2014/0206596 A1 | 7/2014 | Shen et al. |
| 2014/0378660 A1 | 12/2014 | Short et al. |

FOREIGN PATENT DOCUMENTS

| | | |
|---|---|---|
| WO | WO9734911 A1 | 9/1997 |
| WO | WO9746313 A1 | 12/1997 |
| WO | WO9909217 A1 | 2/1999 |
| WO | WO9923105 A1 | 5/1999 |
| WO | WO9951773 A1 | 10/1999 |
| WO | WO2006031370 A2 | 3/2006 |
| WO | WO2010037837 A2 | 4/2010 |
| WO | WO2010037838 A2 | 4/2010 |
| WO | WO2010052014 A1 | 5/2010 |
| WO | WO2010104821 A1 | 9/2010 |
| WO | WO2011005782 A2 | 1/2011 |
| WO | WO2011009058 A2 | 1/2011 |
| WO | WO2012033953 A1 | 3/2012 |
| WO | WO2013046722 A1 | 4/2013 |
| WO | WO2013134743 A9 | 9/2013 |

OTHER PUBLICATIONS

Notification of Violation of Unity Requirement for corresponding Russian application No. 2017127972; dated Apr. 9, 2020; Machine Translation (10 pages).
Office Action for corresponding Canadian application No. 2,977,687; dated Mar. 12, 2021 (4 pages).
Invitation to Respond to Written Opinion for corresponding Singaporean application No. 11201705988U; dated Mar. 12, 2021 (7 pages).
First Office Action for Chinese application No. 201680077540.7; dated Mar. 31, 2021 (19 pages).
Non-Final Office Action for U.S. Appl. No. 15/773,122; dated Mar. 17, 2021 (16 pages).
Youn, Ahrim, et al. "Identifying cancer driver genes in tumor genome sequencing studies." Bioinformatics 27.2 (2011): 175-181.
Goldberg, Robert N., et al. "Thermodynamic Quantities for the Ionization Reactions of Buffers in Water." CRC Handbook of Chemistry and Physics, 101st Edition (Internet Version 2020), John R. Rumble ed., CRC Press/Taylor & Francis, Boca Raton, FL (2003): 1193-1195.
Examination Report No. 2 for corresponding Australian application No. 2016222830; dated Oct. 12, 2020 (4 pages).
Office Action for corresponding Canadian application No. 2,977,687; dated Oct. 2, 2020 (4 pages).
Notice of Reasons for Rejection for corresponding Japanese application No. 2018-522662; dated Sep. 29, 2020 (13 pages).
Notice of Rejection for corresponding Japanese application No. 2018-522662; dated Aug. 3, 2021 (12 pages).
Communication pursuant to Article 94(3) EPC for corresponding European application No. 16862643.0; dated Aug. 23, 2021 (4 pages).
Final Office Action for U.S. Appl. No. 15/773,122; dated Sep. 15, 2021 (11 pages).
Lactic Acid, www.nih.gov, 2021 [retrieved on Jul. 27, 2021] Retrieved from the Internet: <URL: https://pubchem.ncbi.nlm.nih.gov/compound/612> (1 page).
Hseih, S., "Lowry Protein Assay Protocol." www.ucla.edu, 2008 [retrieved on Jun. 12, 2020] Retrieved from the Internet: <URL: http://www.chem.ucla.edu/dept/Faculty/merchant/pdf/Lowry_Assay.pdf> (3 pages).
"Alpha Assays: User Guide to Alpha Assays Protein: Protein Interactions". Maryland, PerkinElmer (2011): 40 pages.
Johnson, M. "Protein Quantitation." www.labome.com, 2012 [retrieved on Jun. 12, 2020] Retrieved from the Internet: <URL: https://www.labome.com/method/Protein-Quantitation.html> (11 pages).
Examination Report for corresponding Australian application No. 2016222830; dated Apr. 8, 2020 (5 pages).

(56) References Cited

OTHER PUBLICATIONS

Restriction Requirement for U.S. Appl. No. 15/773,122; dated Dec. 2, 2020 (8 pages).
Notice of Reasons for Refusal for corresponding Japanese application No. 2017-562970; dated Nov. 4, 2020; Machine Translation (6 pages).
Notification of Reason for Refusal for corresponding Korean application No. 10-2017-7023331; dated Dec. 1, 2020; Machine Translation (11 pages).
Baird, Geoffrey S., et al. "Circular permutation and receptor insertion within green fluorescent proteins." Proceedings of the National Academy of Sciences 96.20 (1999): 11241-11246.
Solbak, Arne I., et al. "Discovery of pectin-degrading enzymes and directed evolution of a novel pectate lyase for processing cotton fabric." Journal of Biological Chemistry 280.10 (2005): 9431-9438.
Office Action for Russian Application No. 2017127972/10; dated Aug. 9, 2019.
Second Written Opinion for corresponding Singaporean Application No. 11201705988U; dated Sep. 20, 2019 (7 pages).
Notice of Rejection for Japanese Application No. 2017-562970; dated Dec. 3, 2019 (13 pages).
Notification of Patentability of the Invention for Russian Application No. 2018115781; dated Dec. 30, 2019; Machine Translation (8 pages).
Mariuzza, R. A. et al. "The structural basis of antigen-antibody recognition." Annual Review of Biophysics and Biophysical Chemistry 16.1 (1987): 139-159.
First Office Action for corresponding Chinese application No. 201680012058.5; dated May 8, 2021 (15 pages).
Communication Pursuant to Article 94(3) EPC for corresponding European application No. 16756238.8; dated May 21, 2021 (5 pages).
International Search Report and Written Opinion; dated Jun. 23, 2016 for PCT Application No. PCT/US2016/019242.
Smith, Temple F., and Michael S. Waterman. "Comparison of biosequences." Advances in applied mathematics 2.4 (1981): 482-489.
Smith, Temple F., and Michael S. Waterman. "Overlapping genes and information theory." Journal of theoretical biology 91.2 (1981): 379-380.
Merrifield, Robert B. "Solid phase peptide synthesis. I. The synthesis of a tetrapeptide." Journal of the American Chemical Society 85.14 (1963): 2149-2154.
Needleman, Saul B., and Christian D. Wunsch. "A general method applicable to the search for similarities in the amino acid sequence of two proteins." Journal of molecular biology 48.3 (1970): 443-453.
Köhler, Georges, and Cesar Milstein. "Continuous cultures of fused cells secreting antibody of predefined specificity." Nature 256.5517 (1975): 495-497.
Bruce, C. H. R. I. S. T. I. N. E., et al. "Histamine levels in plasma, blood, and urine in severe asthma, and the effect of corticosteroid treatment." Thorax 31.6 (1976): 724-729.
Gluzman, Yakov. "SV40-transformed simian cells support the replication of early SV40 mutants." Cell 23.1 (1981): 175-182.
Ecker, Joseph R., and Ronald W. Davis. "Inhibition of gene expression in plant cells by expression of antisense RNA." Proceedings of the National Academy of Sciences 83.15 (1986): 5372-5376.
Brüggemann, Marianne, et al. "Comparison of the effector functions of human immunoglobulins using a matched set of chimeric antibodies." Journal of Experimental Medicine 166.5 (1987): 1351-1361.
Reidhaar-Olson, John F., and Robert T. Sauer. "Combinatorial cassette mutagenesis as a probe of the informational content of protein sequences." Science 241.4861 (1988): 53-58.
Pearson, William R., and David J. Lipman. "Improved tools for biological sequence comparison." Proceedings of the National Academy of Sciences 85.8 (1988): 2444-2448.

Chari, Ravi VJ, et al. "Immunoconjugates containing novel maytansinoids: promising anticancer drugs." Cancer research 52.1 (1992): 127-131.
Patel, Ashvin K., and Paul N. Boyd. "An improved assay for antibody dependent cellular cytotoxicity based on time resolved fluorometry." Journal of immunological methods 184.1 (1995): 29-38.
Kazuo, Maruyama, and Sugano Sumio. "Oligo-capping: a simple method to replace the cap structure of eukaryotic mRNAs with oligoribonucleotides." Gene 138.1 (1994): 171-174.
Seishi, Kato, et al. "Construction of a human full-length cDNA bank." Gene 150.2 (1994): 243-250.
Roberge, Jacques Y., Xenia Beebe, and Samuel J. Danishefsky. "A strategy for a convergent synthesis of N-linked glycopeptides on a solid support." Science—New York Then Washington—(1995): 202-202.
Takahashi, Tomohiro, et al. "Human Fas ligand: gene structure, chromosomal location and species specificity." International immunology 6.10 (1994): 1567-1574.
Kinoshita, Y., and A. Yokota. "Absolute concentrations of metabolites in the human brain tumors using in vitro proton magnetic resonance spectroscopy." NMR in Biomedicine 10.1 (1997): 2-12.
Hendsch, Zachary S., and Bruce Tidor. "Do salt bridges stabilize proteins? A continuum electrostatic analysis." Protein Science 3.2 (1994): 211-226.
Edery, Isaac, et al. "An efficient strategy to isolate full-length cDNAs based on an mRNA cap retention procedure (CAPture)." Molecular and cellular biology 15.6 (1995): 3363-3371.
Clynes, Raphael, et al. "Fc receptors are required in passive and active immunity to melanoma." Proceedings of the National Academy of Sciences 95.2 (1998): 652-656.
Perrin, Charles L., and Jennifer B. Nielson. ""Strong" hydrogen bonds in chemistry and biology" Annual review of physical chemistry 48.1 (1997): 511-544.
Hoogenboom, Hennie R. "Designing and optimizing library selection strategies for generating high-affinity antibodies." Trends in biotechnology 15.2 (1997): 62-70.
Johnston, Mark. "Gene chips: array of hope for understanding gene regulation." Current Biology 8.5 (1998): R171-R174.
Bowtell, David DL. "Options available-from start to finish-for obtaining expression data by microarray." Nature genetics 21.1 Suppl (1999): 25-32.
Humphreys, David P., et al. "High-level periplasmic expression in *Escherichia coli* using a eukaryotic signal peptide importance of codon usage at the 5' end of the coding sequence." Protein expression and purification 20.2 (2000): 252-264.
Feng, Li, et al. "High-level expression and mutagenesis of recombinant human phosphatidylcholine transfer protein using a synthetic gene: evidence for a C-terminal membrane binding domain." Biochemistry 39.50 (2000): 15399-15409.
Narum, David L., et al. "Codon Optimization of Gene Fragments Encoding Plasmodium falciparum Merzoite Proteins Enhances DNA Vaccine Protein Expression and Immunogenicity in Mice." Infection and immunity 69.12 (2001): 7250-7253.
Wilkinson, Robert W., et al. "Antibody-dependent cell-mediated cytotoxicity: a flow cytometry-based assay using fluorophores." Journal of immunological methods 258.1 (2001 ): 183-191.
Outchkourov, Nikolay S., Willem J Stiekema, and Maarten A. Jongsma. "Optimization of the expression of equistatin in Pichia pastoris." Protein expression and purification 24.1 (2002): 18-24.
Ghatta, Srinivas, and D. Nimmagadda. "Calcitonin gene-related peptide: Understanding its role." Indian journal of pharmacology 36.5 (2004): 277.
Arulmani, Udayasankar, et al. "Calcitonin gene-related peptide and its role in migraine pathophysiology" European Journal of pharmacology 500.1 (2004): 315-330.
Bosshard, Hans Rudolf, Daniel N. Marti, and Ilian Jelesarov. "Protein stabilization by salt bridges: concepts, Experimental approaches and clarification of some misunderstandings." Journal of Molecular Recognition 17.1 (2004): 1-16.

(56) References Cited

OTHER PUBLICATIONS

Chi, Sulene L., and Salvatore V. Pizzo. "Angiostatin is directly cytotoxic to tumor cells at low extracellular pH: a mechanism dependent on cell surface-associated ATP synthase." Cancer research 66.2 (2006): 875-882.

Fonseca, Carmen, David Abraham, and Markella Ponticos. "Neuronal regulators and vascular dysfunction in Raynaud's phenomenon and systemic sclerosis." Current vascular pharmacology 7.1 (2009): 34-39.

Albini, Adriana, et al. "Angiostatin anti-angiogenesis requires IL-12: the innate immune system as a key target." Journal of translational medicine 7 .1 (2009): 5.

Donald, Jason E., Daniel W. Kulp, and William F. DeGrado. "Salt bridges: geometrically specific, designable nteractions." Proteins: Structure, Function, and Bioinformatics 79.3 (2011 ): 898-915.

ElMekawy, Ahmed, et al. Valorization of cereal based biorefinery byproducts: reality and expectations. Environmental science & technology 47.16 (2013): 9014-9027.

Akhtar, M. Kalim, Nicholas J. Turner, and Patrik R. Jones. "Carboxylic acid reductase is a versatile enzyme for the conversion of fatly acids into fuels and chemical commodities." Proceedings of the National Academy of Sciences 110.1 (2013): 87-92.

Mayers, Jared R., et al. "Elevation of circulating branched-chain amino acids is an early event in human pancreatic adenocarcinoma development." Nature medicine 20.10 (2014): 1193-1198.

Rothe, Achim, et al. "A phase 1 study of the bispecific anti-CD30/CD16A antibody construct AFM13 in patients with relapsed or refractory Hodgkin lymphoma." Blood 125.26 (2015): 4024-4031.

European Search Report; dated Jun. 19, 2018 for EP Application No. 16756238.8.

Schröter, Christian, et al. "A generic approach to engineer antibody pH-switches using combinatorial histidine scanning libraries and yeast display." MAbs. vol. 7. No. 1. Taylor & Francis, 2015.

Giver, Lori, et al. "Directed evolution of a thermostable esterase." Proceedings of the National Academy of Sciences 95.22 (1998): 12809-12813.

Parak, Fritz G. "Proteins in action: the physics of structural fluctuations and conformational changes." Current opinion in structural biology 13.5 (2003): 552-557.

Karplus, Martin, and John Kuriyan. "Molecular dynamics and protein function." Proceedings of the National Academy of Sciences of the United States of America 102.19 (2005): 6679-6685.

International Search Report and Written Opinion; dated Dec. 1, 2016 for PCT Application No. PCT/US2016/049715.

Singapore Search Report and Written Opinion; dated Aug. 1, 2018 for SG Application No. 11201705988U.

Palackal, Nisha, et al. "An evolutionary route to xylanase process fitness." Protein science 13.2 (2004): 494-503.

First Examination Report for corresponding Indian application No. 201727033470; dated Aug. 5, 2020 (6 pages).

Office Action for corresponding Canadian application No. 2,977,687; dated Oct. 16, 2021 (5 pages).

Second Office Action for corresponding Chinese application No. 201680012058.5; dated Nov. 3, 2021 (17 pages).

Sood, Norman E., et al. "Hydrogen Ion Buffers for Biological Research." Biochemistry 5.2 (1966): 467-477.

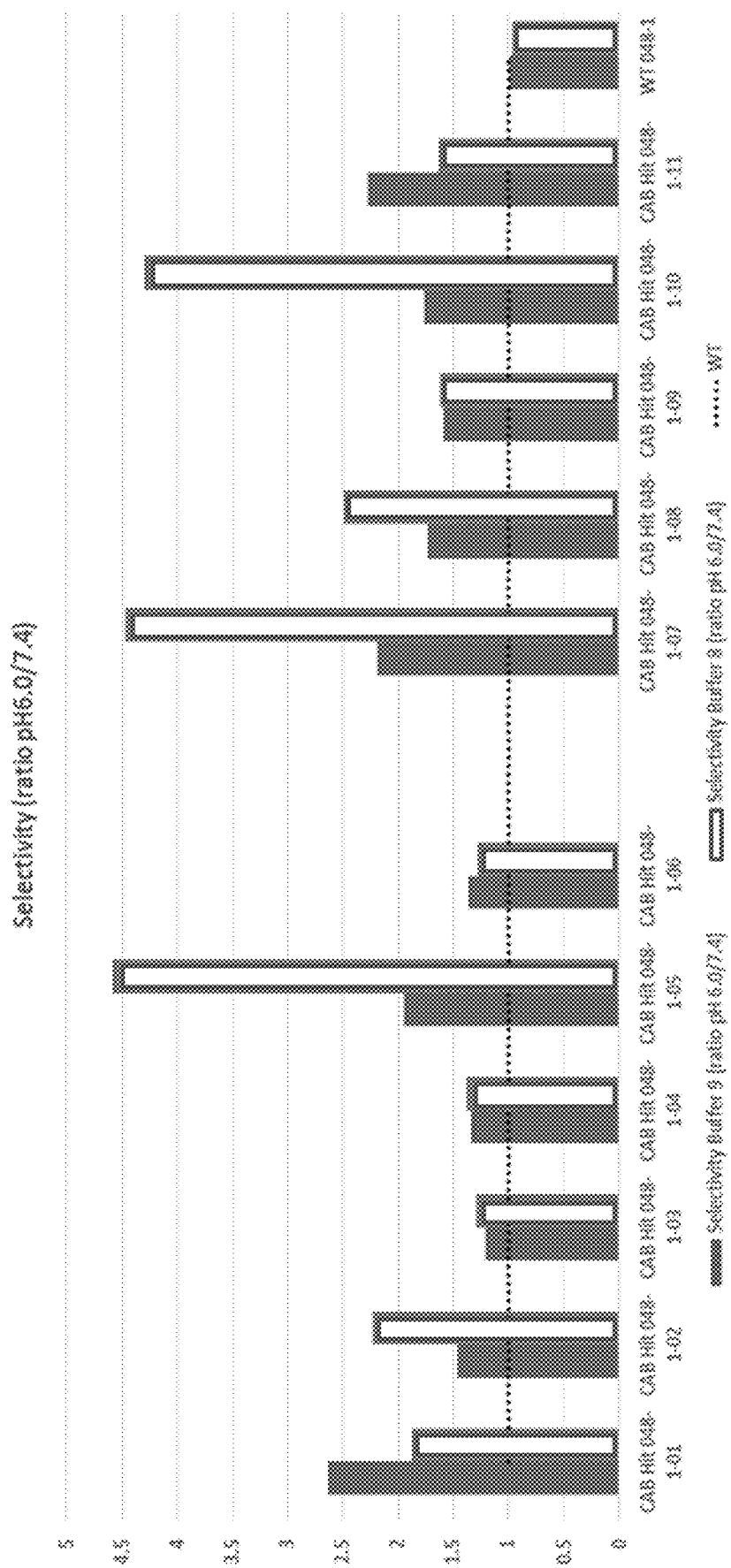

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial
<220> FEATURE:
<223> OTHER INFORMATION: Synthetic sequence
<220> FEATURE:
<221> NAME/KEY: Repeat
<222> LOCATION: (1)..(5)
<223> OTHER INFORMATION: This sequence may repeat multiple times

<400> SEQUENCE: 1

Gly Ser Gly Gly Ser
1               5

<210> SEQ ID NO 2
<211> LENGTH: 4
<212> TYPE: PRT
<213> ORGANISM: Artificial
<220> FEATURE:
<223> OTHER INFORMATION: Synthetic sequence
<220> FEATURE:
<221> NAME/KEY: Repeat
<222> LOCATION: (1)..(4)
<223> OTHER INFORMATION: This sequence may repeat multiple times

<400> SEQUENCE: 2

Gly Gly Gly Ser
```

1

<210> SEQ ID NO 3
<211> LENGTH: 4
<212> TYPE: PRT
<213> ORGANISM: Artificial
<220> FEATURE:
<223> OTHER INFORMATION: Synthetic sequence

<400> SEQUENCE: 3

Gly Gly Ser Gly
1

<210> SEQ ID NO 4
<211> LENGTH: 5
<212> TYPE: PRT
<213> ORGANISM: Artificial
<220> FEATURE:
<223> OTHER INFORMATION: Synthetic sequence

<400> SEQUENCE: 4

Gly Gly Ser Gly Gly
1               5

<210> SEQ ID NO 5
<211> LENGTH: 5
<212> TYPE: PRT
<213> ORGANISM: Artificial
<220> FEATURE:
<223> OTHER INFORMATION: Synthetic sequence

<400> SEQUENCE: 5

Gly Ser Gly Ser Gly
1               5

<210> SEQ ID NO 6
<211> LENGTH: 5
<212> TYPE: PRT
<213> ORGANISM: Artificial
<220> FEATURE:
<223> OTHER INFORMATION: Synthetic sequence

<400> SEQUENCE: 6

Gly Ser Gly Gly Gly
1               5

<210> SEQ ID NO 7
<211> LENGTH: 5
<212> TYPE: PRT
<213> ORGANISM: Artificial
<220> FEATURE:
<223> OTHER INFORMATION: Synthetic sequence

<400> SEQUENCE: 7

Gly Gly Gly Ser Gly
1               5

<210> SEQ ID NO 8
<211> LENGTH: 5
<212> TYPE: PRT
<213> ORGANISM: Artificial
<220> FEATURE:
<223> OTHER INFORMATION: Synthetic sequence

<400> SEQUENCE: 8

Gly Ser Ser Ser Gly
1               5

```
<210> SEQ ID NO 9
<211> LENGTH: 3
<212> TYPE: DNA
<213> ORGANISM: Artificial
<220> FEATURE:
<223> OTHER INFORMATION: synthetic sequence
<220> FEATURE:
<221> NAME/KEY: variation
<222> LOCATION: (1)..(1)
<223> OTHER INFORMATION: This position may be A, T, C, G
<220> FEATURE:
<221> NAME/KEY: misc_feature
<222> LOCATION: (1)..(3)
<223> OTHER INFORMATION: This sequence is repeated 10 times
<220> FEATURE:
<221> NAME/KEY: variation
<222> LOCATION: (2)..(2)
<223> OTHER INFORMATION: This position may be A, T, C, G
<220> FEATURE:
<221> NAME/KEY: variation
<222> LOCATION: (3)..(3)
<223> OTHER INFORMATION: This position may be G or T

<400> SEQUENCE: 9 nnk                                                                     3

<210> SEQ ID NO 10
<211> LENGTH: 3
<212> TYPE: DNA
<213> ORGANISM: artificial
<220> FEATURE:
<223> OTHER INFORMATION: Synthetic sequence
<220> FEATURE:
<221> NAME/KEY: misc_feature
<222> LOCATION: (1)..(3)
<223> OTHER INFORMATION: This sequence is repeated 10 times
<220> FEATURE:
<221> NAME/KEY: variation
<222> LOCATION: (1)..(1)
<223> OTHER INFORMATION: This position may be A, T, C, G
<220> FEATURE:
<221> NAME/KEY: variation
<222> LOCATION: (2)..(2)
<223> OTHER INFORMATION: This position may be A, T, C, G
<220> FEATURE:
<221> NAME/KEY: variation
<222> LOCATION: (3)..(3)
<223> OTHER INFORMATION: This position may be A, or C

<400> SEQUENCE: 10 nnm                                                                     3
```

CONDITIONALLY ACTIVE BIOLOGICAL PROTEINS

CROSS-REFERENCE TO RELATED APPLICATION

This application is a continuation of U.S. patent application Ser. No. 15/546,883, filed on Jul. 27, 2017, currently pending, which, in turn, is a 35 U.S.C. 371 continuation of International application no. PCT/US2016/019242, filed on Feb. 24, 2016, now expired, which, in turn claims the benefit of U.S. provisional application No. 62/249,907 filed on Nov. 2, 2015, and U.S. provisional application No. 62/120,312 filed on Feb. 24, 2015. The disclosures of all of these prior applications are hereby incorporated by reference herein in their entirety.

FIELD OF THE DISCLOSURE

This disclosure relates to the field of protein evolution and activity. Specifically, this disclosure relates to a method of generating conditionally active biologic proteins from wild type proteins, in particular therapeutic proteins, and which are reversibly or irreversibly inactivated at the wild type normal physiological conditions. For example, evolved proteins are virtually inactive at body temperature, but are active at lower temperatures.

BACKGROUND OF THE DISCLOSURE

There is a considerable body of literature describing the potential for evolving proteins for a variety of characteristics, especially enzymes for example, to be stabilized for operation at different conditions. For example, enzymes have been evolved to be stabilized at higher temperatures, with varying activity. In situations where there is an activity improvement at the high temperature, a substantial portion of the improvement can be attributed to the higher kinetic activity commonly described by the Q10 rule where it is estimated that in the case of an enzyme the turnover doubles for every increase of 10 degrees Celsius. In addition, there exist examples of natural mutations that destabilize proteins at their normal operating conditions, such as wild-type temperature activity of the molecule. For temperature mutants, these mutants can be active at the lower temperature, but typically are active at a reduced level compared to the wild type molecules (also typically described by a reduction in activity guided by the Q10 or similar rules).

It is desirable to generate useful molecules that are conditionally activated, for example virtually inactive at wild-type conditions but are active at other than wild-type conditions at a level that is equal or better than at wild-type conditions, or that are activated or inactivated in certain microenvironments, or that are activated or inactivated over time. Besides temperature, other conditions for which the proteins can be evolved or optimized include pH, osmotic pressure, osmolality, oxidative stress and electrolyte concentration. Other desirable properties that can be optimized during evolution include chemical resistance, and proteolytic resistance.

Many strategies for evolving or engineering molecules have been published. However, engineering or evolving a protein to be inactive or virtually inactive (less than 10% activity and especially 1% activity) at its wild type operating condition, while maintaining activity equivalent or better than its wild type condition at new conditions, requires that the destabilizing mutation(s) co-exist with activity increasing mutations that do not counter the destabilizing effect. It is expected that destabilization would reduce the protein's activity greater than the effects predicted by standard rules such as Q10, therefore the ability to evolve proteins that work efficiently at lower temperature, for example, while being inactivated under their normal operating condition, creates an unexpected new class of proteins we refer to as conditionally active biologic proteins.

Throughout this application, various publications are referenced by author and date. The disclosures of these publications in their entireties are hereby incorporated by reference into this application in order to more fully describe the state of the art as known to those skilled therein as of the date of the disclosure described and claimed herein.

SUMMARY OF THE DISCLOSURE

The disclosure provides a method of preparing a conditionally active biologic protein, the method comprising: selecting a wild-type biologic protein; evolving the DNA which encodes the wild-type biologic protein using one or more evolutionary techniques to create a mutant DNA; expressing the mutant DNA to obtain a mutant protein; subjecting the mutant protein and the wild-type protein to an assay under a normal physiological condition and the assay under an aberrant condition; and selecting the conditionally active biologic protein from those mutant proteins which exhibit both (a) a decrease in activity in the assay at the normal physiological condition compared to the wild-type protein, and (b) an increase in activity in the assay under the aberrant condition compared to the wild-type protein. In various aspects, the normal physiological condition is selected from one or more of temperature, pH, osmotic pressure, osmolality, oxidative stress and electrolyte concentration. In a particular aspect, the normal physiological condition is temperature; wherein the conditionally active biologic protein is virtually inactive at the normal physiological temperature, but is active at an aberrant temperature less than the normal physiological temperature. In other aspects, the conditionally active biologic protein is reversibly or irreversibly inactivated at the wild type normal physiological conditions. In one specific aspect, the protein is reversibly inactivated at the wild type normal physiological conditions. Alternatively, conditionally active biologic proteins are selected from those proteins which exhibit changes in activity, reversibly or irreversibly, in two or more different physiological conditions.

In one embodiment, the wild-type biologic protein is an enzyme, in certain aspects, the wild-type biologic protein is selected from the group consisting of tissue plasminogen activator, streptokinase, urokinase, renin, and hyaluronidase.

In another embodiment, the wild-type biologic protein is selected from calcitonin gene-related peptide (CGRP), substance P (SP), neuropeptide Y (NPY), vasoactive intestinal peptide (VTP), vasopressin, and angiostatin.

In another embodiment, the biologic protein is an antibody.

In another embodiment, the disclosure provides a method of preparing a conditionally active biological response modifier, the method comprising: selecting an inflammatory response mediator; identifying a wild-type antibody to the mediator; evolving the wild-type antibody; screening differentially for mutants that exhibit decreased binding to the mediator relative to the wild-type antibody at a first condition, and exhibit increased binding affinity to the mediator at a second condition to identify up-mutants; and recombining the heavy chains and the light chains of the up-mutants to create recombined up-mutants; and screening the recombined up-mutants for mutants that exhibit decreased binding to the mediator relative to the wild-type antibody at the first condition, and show increased binding affinity to the mediator at the second condition to identify the conditionally active biological response modifier. In one aspect, the inflammatory response mediator is selected from IL-6, IL-6 receptor, TNF-alpha, IL-23 and IL-12. In another aspect, the first and second conditions are selected from conditions of pH, osmotic pressure, osmolality, oxidative stress and electrolyte concentration.

In another embodiment, the disclosure provides a pharmaceutical composition comprising a conditionally active biologic protein, and a pharmaceutically acceptable carrier.

BRIEF DESCRIPTION OF THE DRAWING

FIG. 1 is a plot representing the conditionally active antibodies selected in Example 9 and their selectivity in pH 6.0 over pH 7.4.

STATEMENT REGARDING SEQUENCE LISTING

The sequence information content included in the text format of the sequence listing submitted herewith is the same as the sequence information content included in the pdf format of the sequence listing submitted herewith.

Definitions

In order to facilitate understanding of the examples provided herein, certain frequently occurring methods and/or terms will be defined herein.

As used herein in connection with a measured quantity, the term "about" refers to the normal variation in that measured quantity that would be expected by the skilled artisan making the measurement and exercising a level of care commensurate with the objective of the measurement and the precision of the measuring equipment used. Unless otherwise indicated, "about" refers to a variation of +/−10% of the value provided.

The term "activity" as used herein refers to any function that a protein can perform, including catalyzing reactions and binding to a partner. For enzymes, the activity may be an enzymatic activity of the enzyme. For antibodies, the activity may be a binding activity (i.e., binding affinity) between an antibody and its antigen(s). For receptors or ligands, the activity may be binding affinity between a receptor and its ligand.

The term "agent" is used herein to denote a chemical compound, a mixture of chemical compounds, an array of spatially localized compounds (e.g., a VLSIPS peptide array, polynucleotide array, and/or combinatorial small molecule array), biological macromolecule, a bacteriophage peptide display library, a bacteriophage antibody (e.g., scFv) display library, a polysome peptide display library, or an extract made from biological materials such as bacteria, plants, fungi, or animal (particular mammalian) cells or tissues. Agents are evaluated for potential enzyme activity by inclusion in screening assays described herein below. Agents are evaluated for potential activity as conditionally active biologic therapeutic enzymes by inclusion in screening assays described herein below.

An "ambiguous base requirement" in a restriction site refers to a nucleotide base requirement that is not specified to the fullest extent, i.e. that is not a specific base (such as, in a non-limiting exemplification, a specific base selected from A, C, G, and T), but rather may be any one of at least two or more bases. Commonly accepted abbreviations that are used in the art as well as herein to represent ambiguity in bases include the following: R=G or A; Y=C or T; M=A or C; K=G or T; S=G or C; W=A or T; H=A or C or T; B=G or T or C; V=G or C or A; D=G or A or T; N=A or C or G or T.

The term "amino acid" as used herein refers to any organic compound that contains an amino group (—$NH_2$) and a carboxyl group (—COOH); preferably either as free groups or alternatively after condensation as part of peptide bonds. The "twenty naturally encoded polypeptide-forming alpha-amino acids" are understood in the art and refer to: alanine (ala or A), arginine (arg or R), asparagine (asn or N), aspartic acid (asp or D), cysteine (cys or C), gluatamic acid (glu or E), glutamine (gin or Q), glycine (gly or G), histidine (his or H), isoleucine (ile or I), leucine (leu or L), lysine (lys or K), methionine (met or M), phenylalanine (phe or F), proline (pro or P), serine (ser or S), threonine (thr or T), tryptophan (tip or W), tyrosine (tyr or Y), and valine (val or V).

The term "amplification" means that the number of copies of a polynucleotide is increased.

A molecule that has a "chimeric property" is a molecule that is: 1) in part homologous and in part heterologous to a first reference molecule; while 2) at the same time being in part homologous and in part heterologous to a second reference molecule; without 3) precluding the possibility of being at the same time in part homologous and in part heterologous to still one or more additional reference molecules. In a non-limiting embodiment, a chimeric molecule may be prepared by assembling a reassortment of partial molecular sequences. In a non-limiting aspect, a chimeric polynucleotide molecule may be prepared by synthesizing the chimeric polynucleotide using plurality of molecular templates, such that the resultant, chimeric polynucleotide has properties of a plurality of templates.

The term "cognate" as used herein refers to a gene sequence that is evolutionarily and functionally related between species. For example, but not limitation, in the human genome the human CD4 gene is the cognate gene to the mouse 3d4 gene, since the sequences and structures of these two genes indicate that they are highly homologous and both genes encode a protein which functions in signaling T cell activation through MHC class II-restricted antigen recognition.

A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith (Smith and Waterman, 1981, "Comparison of biosequences", *Adv Appl Math,* 2:482-489; Smith and Waterman, 1981, "Overlapping genes and information theory", J Theor Biol, 91:379-380; Smith and Waterman, *J Mol Biol*, "Identification of common molecular subsequences", 1981, 147:195-197; Smith et al., 1981, "Comparative biosequence metrics", *J Mol Evol,* 18:38-46), by the homology alignment algorithm of Needleman (Needleman and Wunsch, 1970, "A general method applicable to the search for similarities in the amino acid sequence of two proteins" *J Mol Biol,* 48(3):443-453), by the search of similarity method of Pearson (Pearson and Lipman, 1988, "Improved tools for biological sequence comparison", *Proc Nat Acad Sci USA,* 85:2444-2448), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "conditionally active biologic protein" refers to a variant, or mutant, of a wild-type protein which is more or less active than the parent wild-type protein under one or more normal physiological conditions. This conditionally active protein also exhibits activity in selected regions of the body and/or exhibits increased or decreased activity under aberrant, or permissive, physiological conditions. Normal physiological conditions are those of temperature, pH, osmotic pressure, osmolality, oxidative stress and electrolyte concentration which would be considered within a normal range at the site of administration, or at the tissue or organ at the site of action, to a subject. An aberrant condition is that which deviates from the normally acceptable range for that condition. In one aspect, the conditionally active biologic protein is virtually inactive at wild-type conditions but is active at other than wild-type conditions at a level that is equal or better than at wild-type conditions. For example, in one aspect, an evolved conditionally active biologic protein is virtually inactive at body temperature, but is active at lower temperatures. In another aspect, the conditionally active biologic protein is reversibly or irreversibly inactivated at the wild type conditions. In a further aspect, the wild-type protein is a therapeutic protein. In another aspect, the conditionally active biologic protein is used as a drug, or therapeutic agent. In yet another aspect, the protein is more or less active in highly oxygenated blood, such as, for example, after passage through the lung or in the lower pH environments found in the kidney.

"Conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference "TATAC" and is complementary to a reference sequence "GTATA."

The term "degrading effective" amount refers to the amount of enzyme which is required to process at least 50% of the substrate, as compared to substrate not contacted with the enzyme.

As used herein, the term "defined sequence framework" refers to a set of defined sequences that are selected on a non-random basis, generally on the basis of experimental data or structural data; for example, a defined sequence framework may comprise a set of amino acid sequences that are predicted to form a .beta.-sheet structure or may comprise a leucine zipper heptad repeat motif, a zinc-finger domain, among other variations. A "defined sequence kernal" is a set of sequences which encompass a limited scope of variability. Whereas (1) a completely random 10-mer sequence of the 20 conventional amino acids can be any of $(20)^{10}$ sequences, and (2) a pseudorandom 10-mer sequence of the 20 conventional amino acids can be any of $(20)^{10}$ sequences but will exhibit a bias for certain residues at certain positions and/or overall, (3) a defined sequence kernal is a subset of sequences if each residue position was allowed to be any of the allowable 20 conventional amino acids (and/or allowable unconventional amino/imino acids). A defined sequence kernal generally comprises variant and invariant residue positions and/or comprises variant residue positions which can comprise a residue selected from a defined subset of amino acid residues, and the like, either segmentally or over the entire length of the individual selected library member sequence. Defined sequence kernels can refer to either amino acid sequences or polynucleotide sequences. Of illustration and not limitation, the sequences $(NNK)_{10}$, SEQ ID NO:9, and $(NNM)_{10}$, SEQ ID NO:10, wherein N represents A, T, G, or C; K represents G or T; and M represents A or C, are defined sequence kernels.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 microgram of plasmid or DNA fragment is used with about 2 units of enzyme in about 20 microliters of buffer solution. For the purpose of isolating DNA fragments for plasmid construction, typically 5 to 50 micrograms of DNA are digested with 20 to 250 units of enzyme in a larger volume. Appropriate buffers and substrate amounts for particular restriction enzymes are specified by the manufacturer. Incubation times of about 1 hour at 37 degrees C. are ordinarily used, but may vary in accordance with the supplier's instructions. After digestion the reaction is electrophoresed directly on a gel to isolate the desired fragment.

"Directional ligation" refers to a ligation in which a 5' end and a 3' end of a polynucleotide are different enough to specify a preferred ligation orientation. For example, an otherwise untreated and undigested PCR product that has two blunt ends will typically not have a preferred ligation orientation when ligated into a cloning vector digested to produce blunt ends in its multiple cloning site; thus, directional ligation will typically not be displayed under these circumstances. In contrast, directional ligation will typically be displayed when a digested PCR product having a 5' EcoR I-treated end and a 3' BamH I is ligated into a cloning vector that has a multiple cloning site digested with EcoR I and BamH I.

The term "DNA shuffling" is used herein to indicate recombination between substantially homologous but non-identical sequences, in some embodiments DNA shuffling may involve crossover via non-homologous recombination, such as via cer/lox and/or flp/frt systems and the like. DNA shuffling can be random or non-random.

The term "drug" or "drug molecule" refers to a therapeutic agent including a substance having a beneficial effect on a human or animal body when it is administered to the human or animal body. Preferably, the therapeutic agent includes a substance that can treat, cure or relieve one or more symptoms, illnesses, or abnormal conditions in a human or animal body or enhance the wellness of a human or animal body.

An "effective amount" is an amount of a conditionally active biologic protein or fragment which is effective to treat or prevent a condition in a living organism to whom it is administered over some period of time, e.g., provides a therapeutic effect during a desired dosing interval.

As used herein, the term "electrolyte" is used to define a mineral in the blood or other body fluids that carries a charge. For example, in one aspect, the normal physiological condition and aberrant condition can be conditions of "electrolyte concentration". In one aspect, the electrolyte concentration to be tested is selected from one or more of ionized calcium, sodium, potassium, magnesium, chloride, bicarbonate, and phosphate concentration. For example, in one aspect, normal range of serum calcium is 8.5 to 10.2 mg/dL. In this aspect, aberrant serum calcium concentration may be selected from either above or below the normal range, m another example, in one aspect, normal range of serum chloride is 96-106 milliequivalents per liter (mEq/L). In this aspect, aberrant serum chloride concentration may be selected from either above or below the normal range, in another example, in one aspect, a normal range of serum magnesium is from 1.7-2.2 mg/dL. In this aspect, an aberrant serum magnesium concentration may be selected from either above or below the normal range, in another example, in one aspect, a normal range of serum phosphorus is from 2.4 to 4.1 mg/dL. In this aspect, aberrant serum phosphorus concentration may be selected from either above or below the normal range. In another example, in one aspect, a normal range of serum, or blood, sodium is from 135 to 145 mEq/L. In this aspect, aberrant serum, or blood, sodium concentration may be selected from either above or below the normal range. In another example, in one aspect, a normal range of serum, or blood, potassium is from 3.7 to 5.2 mEq/L. In this aspect, aberrant serum, or blood, potassium concentration may be selected from either above or below the normal range. In a further aspect, a normal range of serum bicarbonate is from 20 to 29 mEq/L. In this aspect, aberrant serum, or blood, bicarbonate concentration may be selected from either above or below the normal range. In a different aspect, bicarbonate levels can be used to indicate normal levels of acidity (pH), in the blood. The term "electrolyte concentration" may also be used to define the condition of a particular electrolyte in a tissue or body fluid other than blood or plasma. In this case, the normal physiological condition is considered to be the clinically normal range for that tissue or fluid. In this aspect, aberrant tissue or fluid electrolyte concentration may be selected from either above or below the normal range.

As used in this disclosure, the term "epitope" refers to an antigenic determinant on an antigen, such as an enzyme polypeptide, to which the paratope of an antibody, such as an enzyme-specific antibody, binds. Antigenic determinants usually consist of chemically active surface groupings of molecules, such as amino acids or sugar side chains, and can have specific three-dimensional structural characteristics, as well as specific charge characteristics. As used herein "epitope" refers to that portion of an antigen or other macromolecule capable of forming a binding interaction that interacts with the variable region binding body of an antibody. Typically, such binding interaction is manifested as an intermolecular contact with one or more amino acid residues of a CDR.

As used herein, an "enzyme" is a protein with specific catalytic properties. Factors such as, for example, substrate concentration, pH, temperature and presence or absence of inhibitors can affect the rate of catalysis. Typically, for a wild type enzyme, Q10 (the temperature coefficient) describes the increase in reaction rate with a 10 degree C. rise in temperature. For wild type enzymes, the Q10=2 to 3; in other words, the rate of reaction doubles or triples with every 10 degree increase in temperature. At high temperatures, proteins denature. At pH values slightly different from an enzymes optimum value, small changes occur in the charges of the enzyme and perhaps the substrate molecule. The change in ionization can affect the binding of the substrate molecule. At extreme pH levels, the enzyme will produce denaturation, where the active site is distorted, and the substrate molecule will no longer fit.

As used herein, the term "evolution", or "evolving", refers to using one or more methods of mutagenesis to generate a novel polynucleotide encoding a novel polypeptide, which novel polypeptide is itself an improved biological molecule &/or contributes to the generation of another improved biological molecule. In a particular non-limiting aspect, the present disclosure relates to evolution of conditionally active biologic proteins from a parent wild type protein. In one aspect, for example, evolution relates to a method of performing both non-stochastic polynucleotide chimerization and non-stochastic site-directed point mutagenesis disclosed in U.S. patent application publication 2009/0130718. More particularly, the present disclosure provides methods for evolution of conditionally active biologic enzymes which exhibit reduced activity at normal physiological conditions compared to a wild-type enzyme parent molecule, but enhanced activity under one or more aberrant conditions compared to the wild-type enzyme.

The terms "fragment", "derivative" and "analog" when referring to a reference polypeptide comprise a polypeptide which retains at least one biological function or activity that is at least essentially same as that of the reference polypeptide. Furthermore, the terms "fragment", "derivative" or "analog" are exemplified by a "pro-form" molecule, such as a low activity proprotein that can be modified by cleavage to produce a mature enzyme with significantly higher activity.

A method is provided herein for producing from a template polypeptide a set of progeny polypeptides in which a "full range of single amino acid substitutions" is represented at each amino acid position. As used herein, "full range of single amino acid substitutions" is in reference to the 20 naturally encoded polypeptide-forming alpha-amino acids, as described herein.

The term "gene" means the segment of DNA involved in producing a polypeptide chain; it includes regions preceding and following the coding region (leader and trailer) as well as intervening sequences (nitrons) between individual coding segments (exons).

"Genetic instability", as used herein, refers to the natural tendency of highly repetitive sequences to be lost through a process of reductive events generally involving sequence simplification through the loss of repeated sequences. Deletions tend to involve the loss of one copy of a repeat and everything between the repeats.

The term "heterologous" means that one single-stranded nucleic acid sequence is unable to hybridize to another single-stranded nucleic acid sequence or its complement. Thus areas of heterology means that areas of polynucleotides or polynucleotides have areas or regions within their sequence which are unable to hybridize to another nucleic acid or polynucleotide. Such regions or areas are for example areas of mutations.

The term "homologous" or "homeologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentrations as discussed later. Preferably the region of identity is greater than about 5 bp, more preferably the region of identity is greater than 10 bp.

The benefits of this disclosure extend to "industrial applications" (or industrial processes), which term is used to include applications in commercial industry proper (or simply industry) as well as non-commercial industrial applications (e.g. biomedical research at a non-profit institution). Relevant applications include those in areas of diagnosis, medicine, agriculture, manufacturing, and academia.

The term "identical" or "identity" means that two nucleic acid sequences have the same sequence or a complementary sequence. Thus, "areas of identity" means that regions or areas of a polynucleotide or the overall polynucleotide are identical or complementary to areas of another polynucleotide.

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

The term "isolated nucleic acid" is used to define a nucleic acid, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

As used herein "ligand" refers to a molecule, such as a random peptide or variable segment sequence that is recognized by a particular receptor. As one of skill in the art will recognize, a molecule (or macromolecular complex) can be both a receptor and a ligand. In general, the binding partner having a smaller molecular weight is referred to as the ligand and the binding partner having a greater molecular weight is referred to as a receptor.

"Ligation" refers to the process of forming phosphodiester bonds between two double stranded nucleic acid fragments (Sambrook et al., (1982). Molecular Cloning: A Laboratory Manual. Cold Spring Harbour Laboratory, Cold Spring Harbor, N.Y., p. 146; Sambrook et al., Molecular Cloning: a laboratory manual, $2^{nd}$ Ed., Cold Spring Harbor Laboratory Press, 1989). Unless otherwise provided, ligation may be accomplished using known buffers and conditions with 10 units of T4 DNA ligase ("ligase") per 0.5 micrograms of approximately equimolar amounts of the DNA fragments to be ligated.

As used herein, "linker" or "spacer" refers to a molecule or group of molecules that connects two molecules, such as a DNA binding protein and a random peptide, and serves to place the two molecules in a preferred configuration, e.g., so that the random peptide can bind to a receptor with minimal steric hindrance from the DNA binding protein.

As used herein "microenvironment" means any portion or region of a tissue or body that has constant or temporal, physical or chemical differences from other regions of the tissue or regions of the body.

As used herein, a "molecular property to be evolved" includes reference to molecules comprised of a polynucleotide sequence, molecules comprised of a polypeptide sequence, and molecules comprised in part of a polynucleotide sequence and in part of a polypeptide sequence. Particularly relevant—but by no means limiting-examples of molecular properties to be evolved include protein activities at specified conditions, such as related to temperature; salinity; osmotic pressure; pH; oxidative stress, and concentration of glycerol, DMSO, detergent, &/or any other molecular species with which contact is made in a reaction environment. Additional particularly relevant—but by no means limiting—examples of molecular properties to be evolved include stabilities—e.g. the amount of a residual molecular property that is present after a specified exposure time to a specified environment, such as may be encountered during storage.

The term "mutations" means changes in the sequence of a wild-type nucleic acid sequence or changes in the sequence of a peptide. Such mutations may be point mutations such as transitions or transversions. The mutations may be deletions, insertions or duplications.

As used herein, the degenerate "N,N,G/T" nucleotide sequence represents 32 possible triplets, where "N" can be A, C, G or T.

The term "naturally-occurring" as used herein as applied to the object refers to the fact that an object can be found in nature. For example, a polypeptide or polynucleotide sequence that is present in an organism (including viruses) that can be isolated from a source in nature and which has not been intentionally modified by man in the laboratory is naturally occurring. Generally, the term naturally occurring refers to an object as present in a non-pathological (undiseased) individual, such as would be typical for the species.

As used herein, "normal physiological conditions", or "wild type operating conditions", are those conditions of temperature, pH, osmotic pressure, osmolality, oxidative stress and electrolyte concentration which would be considered within a normal range at the site of administration, or the site of action, in a subject.

As used herein, a "nucleic acid molecule" is comprised of at least one base or one base pair, depending on whether it is single-stranded or double-stranded, respectively. Furthermore, a nucleic acid molecule may belong exclusively or chimerically to any group of nucleotide-containing molecules, as exemplified by, but not limited to, the following groups of nucleic acid molecules: RNA, DNA, genomic nucleic acids, non-genomic nucleic acids, naturally occurring and not naturally occurring nucleic acids, and synthetic nucleic acids. This includes, by way of non-limiting example, nucleic acids associated with any organelle, such as the mitochondria, ribosomal RNA, and nucleic acid molecules comprised chimerically of one or more components that are not naturally occurring along with naturally occurring components.

Additionally, a "nucleic acid molecule" may contain in part one or more non-nucleotide-based components as exemplified by, but not limited to, amino acids and sugars. Thus, by way of example, but not limitation, a ribozyme that is in part nucleotide-based and in part protein-based is considered a "nucleic acid molecule".

In addition, by way of example, but not limitation, a nucleic acid molecule that is labeled with a detectable moiety, such as a radioactive or alternatively a nonradioactive label, is likewise considered a "nucleic acid molecule".

The terms "nucleic acid sequence coding for" or a "DNA coding sequence of or a "nucleotide sequence encoding" a particular enzyme—as well as other synonymous terms—refer to a DNA sequence which is transcribed and translated into an enzyme when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease 51) as well as protein binding domains (consensus sequences) responsible for the binding of RNA polymerase.

The terms "nucleic acid encoding an enzyme (protein)" or "DNA encoding an enzyme (protein)" or "polynucleotide encoding an enzyme (protein)" and other synonymous terms encompasses a polynucleotide which includes only coding sequence for the enzyme as well as a polynucleotide which includes additional coding and/or non-coding sequence.

In one preferred embodiment, a "specific nucleic acid molecule species" is defined by its chemical structure, as exemplified by, but not limited to, its primary sequence. In another preferred embodiment, a specific "nucleic acid molecule species" is defined by a function of the nucleic acid species or by a function of a product derived from the nucleic acid species. Thus, by way of non-limiting example, a "specific nucleic acid molecule species" may be defined by one or more activities or properties attributable to it, including activities or properties attributable to its expressed product.

The instant definition of "assembling a working nucleic acid sample into a nucleic acid library" includes the process of incorporating a nucleic acid sample into a vector-based collection, such as by ligation into a vector and transformation of a host. A description of relevant vectors, hosts, and other reagents as well as specific non-limiting examples thereof are provided hereinafter. The instant definition of "assembling a working nucleic acid sample into a nucleic acid library" also includes the process of incorporating a nucleic acid sample into a non-vector-based collection, such as by ligation to adaptors. Preferably the adaptors can anneal to PCR primers to facilitate amplification by PCR.

Accordingly, in a non-limiting embodiment, a "nucleic acid library" is comprised of a vector-based collection of one or more nucleic acid molecules. In another preferred embodiment a "nucleic acid library" is comprised of a non-vector-based collection of nucleic acid molecules. In yet another preferred embodiment a "nucleic acid library" is comprised of a combined collection of nucleic acid molecules that is in part vector-based and in part non-vector-based. Preferably, the collection of molecules comprising a library is searchable and separable according to individual nucleic acid molecule species.

The present disclosure provides a "nucleic acid construct" or alternatively a "nucleotide construct" or alternatively a "DNA construct". The term "construct" is used herein to describe a molecule, such as a polynucleotide (e.g., an enzyme polynucleotide) which may optionally be chemically bonded to one or more additional molecular moieties, such as a vector, or parts of a vector. In a specific—but by no means limiting-aspect, a nucleotide construct is exemplified by DNA expression constructs suitable for the transformation of a host cell.

An "oligonucleotide" (or synonymously an "oligo") refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated. To achieve polymerase-based amplification (such as with PCR), a "32-fold degenerate oligonucleotide that is comprised of, in series, at least a first homologous sequence, a degenerate N,N,G/T sequence, and a second homologous sequence" is mentioned. As used in this context, "homologous" is in reference to homology between the oligo and the parental polynucleotide that is subjected to the polymerase-based amplification.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

As used herein the term "parental polynucleotide set" is a set comprised of one or more distinct polynucleotide species. Usually this term is used in reference to a progeny polynucleotide set which is preferably obtained by mutagenization of the parental set, in which case the terms "parental", "starting" and "template" are used interchangeably.

The term "patient", or "subject", refers to an animal, for example a mammal, such as a human, who is the object of treatment. The subject, or patient, may be either male or female.

As used herein the term "physiological conditions" refers to temperature, pH, osmotic pressure, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50-200 mM NaCl or KCl, pH 6.5-8.5, 20-45 degrees C. and 0.001-10 mM divalent cation (e.g., $Mg^{++}$, $Ca^{++}$); preferably about 150 mM NaCl or KCl, pH 7.2-7.6, 5 mM divalent cation, and often include 0.01-1.0 percent nonspecific protein (e.g., BSA). A non-ionic detergent (Tween, NP-40, Triton X-100) can often be present, usually at about 0.001 to 2%, typically 0.05-0.2% (v/v). Particular aqueous conditions may be selected by the practitioner according to conventional methods. For general guidance, the following buffered aqueous conditions may be applicable: 10-250 mM NaCl, 5-50 mM Tris HCl, pH 5-8, with optional addition of divalent cation(s) and/or metal chelators and/or non-ionic detergents and/or membrane fractions and/or anti-foam agents and/or scintillants. Normal physiological conditions refer to conditions of temperature, pH, osmotic pressure, osmolality, oxidative stress and electrolyte concentration in vivo in a patient or subject at the site of administration, or the site of action, which would be considered within the normal range in a patient.

Standard convention (5' to 3') is used herein to describe the sequence of double stranded polynucleotides.

The term "population" as used herein means a collection of components such as polynucleotides, portions or polynucleotides or proteins. A "mixed population" means a collection of components which belong to the same family of nucleic acids or proteins (i.e., are related) but which differ in their sequence (i.e., are not identical) and hence in their biological activity.

A molecule having a "pro-form" refers to a molecule that undergoes any combination of one or more covalent and noncovalent chemical modifications (e.g. glycosylation, proteolytic cleavage, dimerization or oligomerization, temperature-induced or pH-induced conformational change, association with a co-factor, etc.) en route to attain a more mature molecular form having a property difference (e.g. an increase in activity) in comparison with the reference pro-form molecule. When two or more chemical modifications (e.g. two proteolytic cleavages, or a proteolytic cleavage and a deglycosylation) can be distinguished en route to the production of a mature molecule, the reference precursor molecule may be termed a "pre-pro-form" molecule.

As used herein, the term "protein" refers to a polymer in which the monomers are amino acids and are joined together through peptide or disulfide bonds. "Protein" refers to a full-length naturally-occurring amino acid chain or a fragment thereof, such as a selected region of the polypeptide that is of interest in a binding interaction, or a synthetic amino acid chain, or a combination thereof. Fragment thereof thus refers to an amino acid sequence that is a portion of a full-length protein, between about 8 and about 500 amino acids in length, preferably about 8 to about 300 amino acids, more preferably about 8 to about 200 amino acids, and even more preferably about 10 to about 50 or 100 amino acids in length. Additionally, amino acids other than naturally-occurring amino acids, for example β-alanine, phenyl glycine and homoarginine, may be included in the proteins. Commonly-encountered amino acids which are not gene-encoded may also be used in the present invention. All of the amino acids used in the present invention may be either the D- or L-optical isomer. The D-isomers are preferred for use in a specific context, further described below. In addition, other peptidomimetics are also useful, e.g. in linker sequences of polypeptides of the present invention (see Spatola, 1983, in Chemistry and Biochemistry of Amino Acids. Peptides and Proteins, Weinstein, ed., Marcel Dekker, New York, p. 267). In general, the term "protein" is not intended to convey any significant difference from the term "polypeptide" other than to include structures which comprise two or several polypeptide chains held together by covalent or non-covalent bonds.

As used herein, the term "pseudorandom" refers to a set of sequences that have limited variability, such that, for example, the degree of residue variability at another position, but any pseudorandom position is allowed some degree of residue variation, however circumscribed.

"Quasi-repeated units", as used herein, refers to the repeats to be re-assorted and are by definition not identical. Indeed the method is proposed not only for practically identical encoding units produced by mutagenesis of the identical starting sequence, but also the reassortment of similar or related sequences which may diverge significantly in some regions. Nevertheless, if the sequences contain sufficient homologies to be reasserted by this approach, they can be referred to as "quasi-repeated" units.

As used herein "random peptide library" refers to a set of polynucleotide sequences that encodes a set of random peptides, and to the set of random peptides encoded by those polynucleotide sequences, as well as the fusion proteins that contain those random peptides.

As used herein, "random peptide sequence" refers to an amino acid sequence composed of two or more amino acid monomers and constructed by a stochastic or random process. A random peptide can include framework or scaffolding motifs, which may comprise invariant sequences.

As used herein, "receptor" refers to a molecule that has an affinity for a given ligand. Receptors can be naturally occurring or synthetic molecules. Receptors can be employed in an unaltered state or as aggregates with other species. Receptors can be attached, covalently or non-covalently, to a binding member, either directly or via a specific binding substance. Examples of receptors include, but are not limited to, antibodies, including monoclonal antibodies and antisera reactive with specific antigenic determinants (such as on viruses, cells, or other materials), cell membrane receptors, complex carbohydrates and glycoproteins, enzymes, and hormone receptors.

"Recombinant" enzymes refer to enzymes produced by recombinant DNA techniques, i.e., produced from cells transformed by an exogenous DNA construct encoding the desired enzyme. "Synthetic" enzymes are those prepared by chemical synthesis.

The term "related polynucleotides" means that regions or areas of the polynucleotides are identical and regions or areas of the polynucleotides are heterologous.

"Reductive reassortment", as used herein, refers to the increase in molecular diversity that is accrued through deletion (and/or insertion) events that are mediated by repeated sequences.

The following terms are used to describe the sequence relationships between two or more polynucleotides: "reference sequence," "comparison window," "sequence identity," "percentage of sequence identity," and "substantial identity."

A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides and (2) may further comprise a sequence that is divergent between the two polynucleotides, sequence comparisons between two (or more) polynucleotides are performed by comparing sequences of the two polynucleotides over a "comparison window" to identify and compare local regions of sequence similarity.

"Repetitive Index (RI)", as used herein, is the average number of copies of the quasi-repeated units contained in the cloning vector.

The term "restriction site" refers to a recognition sequence that is necessary for the manifestation of the action of a restriction enzyme, and includes a site of catalytic cleavage. It is appreciated that a site of cleavage may or may not be contained within a portion of a restriction site that comprises a low ambiguity sequence (i.e. a sequence containing the principal determinant of the frequency of occurrence of the restriction site). Thus, in many cases, relevant restriction sites contain only a low ambiguity sequence with an internal cleavage site (e.g. G/AATTC in the EcoR I site) or an immediately adjacent cleavage site (e.g./CCWGG in the EcoR II site), in other cases, relevant restriction enzymes [e.g. the Eco57 I site or CTGAAG(16/14)] contain a low ambiguity sequence (e.g. the CTGAAG sequence in the Eco57 I site) with an external cleavage site (e.g. in the N.sub.16 portion of the Eco57 I site). When an enzyme (e.g. a restriction enzyme) is said to "cleave" a polynucleotide, it is understood to mean that the restriction enzyme catalyzes or facilitates a cleavage of a polynucleotide.

In a non-limiting aspect, a "selectable polynucleotide" is comprised of a 5' terminal region (or end region), an intermediate region (i.e. an internal or central region), and a 3 'terminal region (or end region). As used in this aspect, a 5' terminal region is a region that is located towards a 5' polynucleotide terminus (or a 5' polynucleotide end); thus it is either partially or entirely in a 5' half of a polynucleotide. Likewise, a 3' terminal region is a region that is located towards a 3' polynucleotide terminus (or a 3' polynucleotide end); thus it is either partially or entirely in a 3' half of a polynucleotide. As used in this non-limiting exemplification, there may be sequence overlap between any two regions or even among all three regions.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. This "substantial identity", as used herein, denotes a characteristic of a polynucleotide sequence, wherein the polynucleotide comprises a sequence having at least 80 percent sequence identity, preferably at least 85 percent identity, often 90 to 95 percent sequence identity, and most commonly at least 99 percent sequence identity as compared to a reference sequence of a comparison window of at least 25-50 nucleotides, wherein the percentage of sequence identity is calculated by comparing the reference sequence to the polynucleotide sequence which may include deletions or additions which total 20 percent or less of the reference sequence over the window of comparison.

As known in the art "similarity" between two enzymes is determined by comparing the amino acid sequence and its conserved amino acid substitutes of one enzyme to the sequence of a second enzyme. Similarity may be determined by procedures which are well-known in the art, for example, a BLAST program (Basic Local Alignment Search Tool at the National Center for Biological Information).

The members of a pair of molecules (e.g., an antibody-antigen pair or a nucleic acid pair) are said to "specifically bind" to each other if they bind to each other with greater affinity than to other, non-specific molecules. For example, an antibody raised against an antigen to which it binds more efficiently than to a non-specific protein can be described as specifically binding to the antigen. (Similarly, a nucleic acid probe can be described as specifically binding to a nucleic acid target if it forms a specific duplex with the target by base pairing interactions (see above).)

"Specific hybridization" is defined herein as the formation of hybrids between a first polynucleotide and a second polynucleotide (e.g., a polynucleotide having a distinct but substantially identical sequence to the first polynucleotide), wherein substantially unrelated polynucleotide sequences do not form hybrids in the mixture.

The term "specific polynucleotide" means a polynucleotide having certain end points and having a certain nucleic acid sequence. Two polynucleotides wherein one polynucleotide has the identical sequence as a portion of the second polynucleotide but different ends comprises two different specific polynucleotides.

"Stringent hybridization conditions" means hybridization will occur only if there is at least 90% identity, preferably at least 95% identity and most preferably at least 97% identity between the sequences. See Sambrook et al., Molecular Cloning: a laboratory manual, $2^{nd}$ Ed., Cold Spring Harbor Laboratory Press, 1989.

Also included in the disclosure are polypeptides having sequences that are "substantially identical" to the sequence of an enzyme polypeptide. A "substantially identical" amino acid sequence is a sequence that differs from a reference sequence only by conservative amino acid substitutions, for example, substitutions of one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid, or glutamine for asparagine).

Additionally a "substantially identical" amino acid sequence is a sequence that differs from a reference sequence or by one or more non-conservative substitutions, deletions, or insertions, particularly when such a substitution occurs at a site that is not the active site of the molecule, and provided that the polypeptide essentially retains its behavioural properties. For example, one or more amino acids can be deleted from an enzyme polypeptide, resulting in modification of the structure of the polypeptide, without significantly altering its biological activity. For example, amino- or carboxyl-terminal amino acids that are not required for enzyme biological activity can be removed. Such modifications can result in the development of smaller active enzyme polypeptides.

The present disclosure provides a "substantially pure enzyme". The term "substantially pure enzyme" is used herein to describe a molecule, such as a polypeptide (e.g., an enzyme polypeptide, or a fragment thereof) that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. The purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

As used herein, "substantially pure" means an object species is the predominant species present (i.e., on a molar basis it is more abundant than any other individual macromolecular species in the composition), and preferably substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

The term "treating" includes: (1) preventing or delaying the appearance of clinical symptoms of the state, disorder or condition developing in an animal that may be afflicted with or predisposed to the state, disorder or condition but does not yet experience or display clinical or subclinical symptoms of the state, disorder or condition; (2) inhibiting the state, disorder or condition (i.e., arresting, reducing or delaying the development of the disease, or a relapse thereof in case of maintenance treatment, of at least one clinical or subclinical symptom thereof); and/or (3) relieving the condition (i.e., causing regression of the state, disorder or condition or at least one of its clinical or subclinical symptoms). The benefit to a patient to be treated is either statistically significant or at least perceptible to the patient or to the physician.

As used herein, the term "variable segment" refers to a portion of a nascent peptide which comprises a random, pseudorandom, or defined kernal sequence. A "variable segment" refers to a portion of a nascent peptide which comprises a random pseudorandom, or defined kernal sequence. A variable segment can comprise both variant and invariant residue positions, and the degree of residue variation at a variant residue position may be limited: both options are selected at the discretion of the practitioner. Typically, variable segments are about 5 to 20 amino acid residues in length (e.g., 8 to 10), although variable segments may be longer and may comprise antibody portions or receptor proteins, such as an antibody fragment, a nucleic acid binding protein, a receptor protein, and the like.

The term "variant" refers to polynucleotides or polypeptides of the disclosure modified at one or more base pairs, codons, introns, exons, or amino acid residues (respectively) of a wild-type protein parent molecule. Variants can be produced by any number of means including methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, saturation mutagenesis and any combination thereof. Techniques for producing variant proteins having reduced activity compared to the wild-type protein at a normal physiological condition of e.g., one or more conditions of temperature, pH, osmotic pressure, osmolality, oxidative stress and electrolyte concentration; and enhanced activity at an aberrant condition, are disclosed herein. Variants may additionally be selected for the properties of enhanced chemical resistance, and proteolytic resistance, compared to the wild-type protein.

As used herein, the term "wild-type" means that the polynucleotide does not comprise any mutations. A "wild type protein", "wild-type protein", "wild-type biologic protein", or "wild type biologic protein", refers to a protein which can be isolated from nature that will be active at a level of activity found in nature and will comprise the amino acid sequence found in nature. The terms "parent molecule" and "target protein" also refer to the wild-type protein.

The term "working", as in "working sample", for example, is simply a sample with which one is working. Likewise, a "working molecule", for example is a molecule with which one is working.

The term "conditionally active antibody" refers to a variant, or mutant, of a wild-type antibody which is more active or less active than the parent wild-type antibody under one or more normal physiological conditions. This conditionally active antibody may exhibit activity in selected regions of the body and/or may exhibit increased activity or decreased activity under aberrant, or permissive, physiological conditions. In one aspect, the conditionally active antibody is virtually inactive at normal physiological conditions but is active at other than normal physiological conditions at a level that is better than at normal physiological conditions. For example, in one aspect, an evolved conditionally active antibody may be virtually inactive at body temperature, but is active at lower temperatures. In another aspect, the conditionally active antibody may be reversibly or irreversibly inactivated at the normal physiological conditions. In a further aspect, the wild-type antibody is a therapeutic antibody. In another aspect, the conditionally active antibody is used as a drug, or therapeutic agent. In yet another aspect, the antibody is more or less active in highly oxygenated blood, such as, for example, after passage through the lung or in the lower pH environments found in the kidney.

The term "antibody-dependent cell-mediated cytotoxicity" or "ADCC" refers to a form of cytotoxicity in which secreted immunoglobulin bound onto Fc receptors (FcRs) present on certain cytotoxic cells (e.g., Natural Killer (NK) cells, neutrophils, and macrophages) that enables these cytotoxic effector cells to bind specifically to an antigen-bearing target cell and subsequently kill the target cell with cytotoxins. Ligand specific high-affinity IgG antibodies directed to the surface of target cells stimulate the cytotoxic cells and are required for such killing. Lysis of the target cell is extracellular, requires direct cell-to-cell contact, and does not involve a complement.

The ability of any particular antibody to mediate lysis of the target cell by ADCC can be assayed. To assess ADCC activity, an antibody of interest is added to target cells displaying the target ligand in combination with immune effector cells, which may be activated by the antigen antibody complexes resulting in cytolysis of the target cell. Cytolysis is generally detected by the release of a label (e.g., radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Bruggemann et al, 1987, *J Exp Med*, vol. 166, page 1351; Wilkinson et al, 2001, *J Immunol Methods*, vol. 258, page 183; Patel et al, 1995 *J Immunol Methods*, vol. 184, page 29. Alternatively, or additionally, ADCC activity of the antibody of interest may be assessed in vivo, e.g., in an animal model, such as that disclosed in Clynes et al, 1998, *PNAS USA*, vol. 95, p. 652.

The terms "cancer" and "cancerous" refer to or describe the physiological condition in mammals that is typically characterized by unregulated cell growth/proliferation. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The term "multispecific antibody" as used herein is an antibody having binding specificities for at least two different epitopes. Exemplary multispecific antibodies may bind both a BBB-R and a brain antigen. Multispecific antibodies can be prepared as full-length antibodies or antibody fragments (e.g. F(ab')$_2$ bispecific antibodies). Engineered antibodies with two, three or more (e.g. four) functional antigen binding sites are also, contemplated (see, e.g., US 2002/0004587 A1). Multispecific antibodies can be prepared as full length antibodies or antibody fragments.

The term "full length antibody" refers to an antibody which comprises an antigen-binding variable region (VH or VL) as well as a light chain constant domain (CL) and heavy chain constant domains, CH1, CH2 and CH3. The constant domains may be native sequence constant domains (e.g. human native sequence constant domains) or amino acid sequence variants thereof.

Depending on the amino acid sequence of the constant domain of their heavy chains, full length antibodies can be assigned to different "classes". There are five major classes of full length antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called alpha, delta, epsilon, gamma, and mu, respectively.

The term "library" as used herein refers to a collection of proteins in a single pool. The library of the invention is preferably generated using DNA recombinant technology. For example, a collection of cDNAs or any other protein coding DNAs may be inserted in an expression vector to generate a protein library. The expression vector may be selected from plasmids, cosmids, artificial chromosomes, and viral expression vectors. A collection of cDNAs or protein coding DNAs may also be inserted into a phage genome to generate a bacteriophage display library of wild-type proteins. The collection of cDNAs may be produced from a selected cell population or a tissue sample, such as by the methods disclosed by Sambrook et al. (Molecular Cloning, Cold Spring Harbor Laboratory Press, 1989). cDNA collections from selected cell types are also commercially available from vendors such as Stratagene®. The library of wild-type proteins as used herein is not a collection of biological samples.

The term "recombinant antibody", as used herein, refers to an antibody (e.g. a chimeric, humanized, or human antibody or antigen-binding fragment thereof) that is expressed by a recombinant host cell comprising a nucleic acid encoding the antibody. Examples of "host cells" for producing recombinant antibodies include: (1) mammalian cells, for example, Chinese Hamster Ovary (CHO), COS, myeloma cells (including Y0 and NS0 cells), baby hamster kidney (BHK), Hela and Vero cells; (2) insect cells, for example, sf9, sf21 and Tn5; (3) plant cells, for example plants belonging to the genus *Nicotiana* (e.g. *Nicotiana tabacum*); (4) yeast cells, for example, those belonging to the genus *Saccharomyces* (e.g. *Saccharomyces cerevisiae*) or the genus *Aspergillus* (e.g. *Aspergillus niger*); (5) bacterial cells, for example *Escherichia. coli* cells or *Bacillus subtilis* cells, etc.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

DETAILED DESCRIPTION

The present disclosure is directed to methods of engineering or evolving proteins to generate new molecules that are reversibly or irreversibly inactivated at the wild type condition, but active at non-normal conditions at the same or equivalent level as the wild-type condition. These new proteins are referred to as conditionally active biologic proteins herein. These conditionally active biologic proteins and methods of producing these proteins have been described in US 2012/0164127. Conditionally active biologic proteins are particularly valuable for development of novel therapeutics that are active for short or limited periods of time within the host. This is particularly valuable where extended operation of the protein at the given dose would be harmful to the host, but where limited activity is required to perform the desired therapy. Examples of beneficial applications include topical or systemic treatments at high dose, as well as localized treatments in high concentration. Inactivation under the physiological condition can be determined by a combination of the dosing and the rate of inactivation of the protein. This condition based inactivation is especially important for enzyme therapeutics where catalytic activity cause substantial negative effects in a relatively short period of time.

The present disclosure is also directed to methods of engineering or evolving proteins to generate new molecules that are different from wild type molecules in that they are reversibly or irreversibly activated or inactivated over time, or activated or inactivated only when they are in certain microenvironments in the body, including in specific organs in the body (such as the bladder or kidney). In some embodiments, the conditionally active biologic proteins are antibodies against one or more target proteins as described herein.

Target Wild-Type Proteins

Any therapeutic protein can serve as a target protein, or wild-type protein, for production of a conditionally active biologic protein. In one aspect, the target protein is a wild-type enzyme. Currently used therapeutic enzymes include urokinase and streptokinase, used in the treatment of blood clots; and hyaluronidase, used as an adjuvant to improve the absorption and dispersion of other drugs, in one aspect, the wild-type protein selected for generation of a conditionally active biologic protein can be a currently used therapeutic enzyme, in order to avoid or minimize deleterious side effects associated with the wild-type protein or enzyme. Alternatively, an enzyme not in current usage as a therapeutic can be selected for generation of a conditionally active biologic protein. Certain non-limiting examples will be discussed in further detail below.

Therapeutic proteins are those which can be used in medicine either alone or in conjunction with other therapies to treat various diseases or medical conditions. The conditionally active biologic proteins of the disclosure could be appropriate for use in one or more indications including the treatment of circulatory disorders, arthritis, multiple sclerosis, autoimmune disorders, cancer, dermatologic conditions and use in various diagnostic formats. Depending on the protein and indication, the conditionally active biologic enzyme protein could be administered in parenteral, topical or oral formulations as discussed below.

Circulatory Disorders—Thrombosis and Thrombolytic Therapy.

A thrombus (blood clot) is defined as a solid mass derived from blood constituents that form in the circulatory system. The thrombus is formed by a series of events involving blood coagulation factors, platelets, red blood cells, and interactions with the vessel wall. A platelet is an intravascular aggregation of platelets, fibrin and entrapped blood cells which can cause vascular obstruction. By obstructing or blocking blood flow, the thrombus deprives downstream tissue of oxygen supply. Fragments (emboli) of the thrombus may break away and obstruct smaller vessels. Arterial thrombus formation is precipitated by any of a variety of factors including an underlying stenosis-atherosclerosis, a low flow state-cardiac function, hypercoaguability as in cancer or a coagulation factor deficiency, or a foreign body such as a stent or catheter. A thrombus leading to arterial ischemia can result in limb or tissue injury, acute myocardial infarction (AMI), stroke, amputation, or bowel infarction. Major causes of morbidity and mortality are the formation of arterial thrombi (coronary arterial thrombi and cerebral arterial thrombi) and pulmonary thrombi. Venous thrombus formation can occur due to endothelial injury such as trauma, stasis due to e.g. immobility, or hypercoagulability, but atherosclerosis is not a factor. Treatment strategies include mechanical thrombectomy, pharmacomechanical thrombectomy and thrombolysis. Thrombotic therapy is used to minimize formation and aid in removal of thrombi.

Thrombotic therapy includes the use of antiplatelet agents which inhibit platelet activation, anticoagulant therapies, and/or thrombolytic therapy to degrade blood clots. Examples of antiplatelets include aspirin, dipyridamole, and ticlopidine. Examples of anticoagulants include heparin, warfarin, hirudin, and activated human protein C. Examples of thrombolytics include tissue plasminogen activator (tPA)/tPA variants, urokinase and streptokinase. The thrombolytics display a catalytic mode of action.

Thrombolytic therapy in acute myocardial infarction is well established. Use of thrombolytic agents has become standard emergency treatment. Although effective, these products achieve complete reperfusion in only about 50% of patients and side effects include risk of hemorrhage (in particular intracranial bleeding) as well as hypertension. The degradation of blood clots from a damaged or diseased vessel is termed "fibrinolysis" or the "fibrinolytic process". Fibrinolysis is a proteolytic process, by a plasminogen activator which activates the protein plasminogen, thereby forming plasmin Plasmin proteolytically degrades the fibrin strands of the blood clot to dissolve the clot. Fibrin specific plasminogen activators include tissue plasminogen activators or variants. Non-specific plasminogen activators can include streptokinase and urokinase.

Certain commonly used thrombolytic therapies utilize one of several available tissue plasminogen activator (tPA) variants. For example, tPA based product variants which have been previously approved for use are Alteplase (rt-PA), Reteplase (r-PA) and Tenecteplase (TNK). Approved uses for tPA variants include, for example, acute myocardial infarction for the improvement of ventricular function following AMI, the reduction of incidence of congestive heart failure, and reduction of mortality associated with AMI, management of ischemic stroke in adults for improving neurological recovery and reducing incidence of disability, management of acute massive pulmonary embolism in adults for the lysis of acute pulmonary emboli, and for the lysis of pulmonary emboli accompanied by unstable hemodynamics.

Another commonly used thrombolytic therapy utilizes urokinase. Urokinase is a standard lytic agent used in the management of peripheral vascular disease.

Streptokinase is a protein secreted by several species of streptococci that can bind and activate human plasminogen. Complexes of streptokinase with human plasminogen can hydrolytically activate other unbound plasminogen by activating through bond cleavage to produce plasmin. The usual activation of plasminogen is through the proteolysis of the Arg561-Val562 bond. The amino group of Val562 then forms a salt-bridge with Asp740, which causes a conformational change to produce the active protease plasmin. Plasmin is produced in the blood to break down fibrin, the major constituent of blood clots.

Streptokinase is used as an effective clot-dissolving medication in some cases of myocardial infarction (heart attack), pulmonary embolism (lung blood clots), and deep venous thrombosis (leg blood clots). Streptokinase belongs to a group of medications called fibrinolytics. Streptokinase is given as soon as possible after the onset of a heart attack to dissolve clots in the arteries of the heart wall and reduce damage to the heart muscle. Streptokinase is a bacterial product, so the body has the ability to build up immunity against the protein. Therefore, it is recommended that this product should not be given again after four days from the first administration, as it may not be as effective and cause an allergic reaction. For this reason it is usually given only after a first heart attack, and further thrombotic events are typically treated with tissue plasminogen activator (TPA). Streptokinase is also sometimes used to prevent post-operative adhesions.

Side effects of streptokinase include bleeding (major and minor), hypotension, and respiratory depression as well as possible allergic reaction. In addition, anticoagulants, agents that alter platelet function (e.g. aspirin, other NSAIDs, dipyridamole) may increase risk of bleeding.

Administration of the thrombolytics is generally by infusion or by bolus intravenous dose; or by a mechanical infusion system. Adverse effects can include serious intracranial, gastrointestinal, retroperitoneal, or pericardial bleeding. If bleeding occurs the administration must be discontinued immediately.

In certain embodiments of the disclosure, tPA, streptokinase or urokinase is selected as the target, or wild-type protein.

In one embodiment, the methods of the disclosure are used to select for a conditionally active recombinant or synthetic streptokinase variant with high activity at aberrant temperature conditions below normal physiological conditions; and substantial deactivation or inactivation at normal physiological conditions (e.g. 37 degrees C.). In one aspect, the aberrant temperature condition is room temperature, e.g. 20-25 degrees C. In another aspect, the disclosure provides a method of treating a stroke or heart attack, the method comprising administering a high dose of the conditionally active streptokinase variant to stroke or heart attack victims in order to clear clots, yet allow for rapid inactivation of the streptokinase variant to avoid excessive bleeding.

Circulatory Disorders—Renin/Angiotensin

The renin-angiotensin system is a hormone system that regulates blood pressure and water (fluid) balance. The kidneys secrete renin when the blood volume is low. Renin is an enzyme which hydrolyzes angiotensinogen secreted from the liver into the peptide angiotensin I. Angiotensin I is further cleaved in the lungs by endothelial-bound angiotensin converting enzyme (ACE) into angiotensin II, the most vasoactive peptide. Angiotensin II causes the blood vessels to constrict, resulting in increased blood pressure. However, angiotensin π also stimulates the secretion of the hormone aldosterone from the adrenal cortex. Aldosterone causes the tubules of the kidneys to increase the resorption of sodium and water. This increases the volume of fluid in the body, which also increases blood pressure. An overactive renin-angiotensin system leads to vasoconstriction and retention of sodium and water. These effects lead to hypertension. There are many drugs which interrupt different steps in this system to lower blood pressure. These drugs are one of the main ways to control high blood pressure (hypertension), heart failure, kidney failure, and harmful effects of diabetes.

Hypovolemic shock is an emergency condition in which severe blood and/or fluid loss makes the heart unable to adequately perfuse the body's cells with oxygenated blood. Blood loss can be from trauma, injuries and internal bleeding. The amount of circulating blood may drop due to excessive fluid loss from burns, diarrhea, excessive perspiration or vomiting. Symptoms of hypovolemic shock include anxiety, cool clammy skin, confusion, rapid breathing, or unconsciousness. Examination shows signs of shock including low blood pressure, low body temperature, and rapid pulse, which may be weak or thready. Treatment includes intravenous fluids; blood or blood products; treatment for shock; and medication such as dopamine, dobutamine, epinephrine and norepinephrine to increase blood pressure and cardiac output.

In one embodiment, the disclosure provides a method of selecting for a conditionally active recombinant renin variant to be reversibly deactivated at normal physiological temperature, but reactivated at the aberrant lower temperatures in a patient with hypovolemic shock. The conditionally active protein can be used to treat hypovolemic shock to help increase the volume of fluid in the body, and increase blood pressure.

Circulatory Disorders—Reynaud's Phenomenon

Reynaud's phenomenon (RP) is a vasospastic disorder causing discoloration of the fingers, toes and occasionally other extremities. Emotional stress and cold are classic triggers of the phenomenon. When exposed to cold temperatures, the extremities lose heat. The blood supply to fingers and toes is normally slowed to preserve the body's core temperature. Blood flow is reduced by the narrowing of small arteries under the skin of the extremities. Stress causes similar reaction to cold in the body. Li Reynaud's, the normal response is exaggerated. The condition can cause pain, discoloration, and sensations of cold and numbness. The phenomenon is the result of vasospasms that decrease the blood supply to the respective regions, in Reynaud's disease (Primary Raynaud's phenomenon), the disease is idiopathic. Li Raynaud's syndrome (Secondary Reynaud's), the phenomenon is caused by some other instigating factor. Measurement of hand-temperature gradients is one tool to distinguish between the primary and secondary forms. The primary form can progress to the secondary form, and in extreme cases, the secondary form can progress to necrosis or gangrene of the fingertips.

Raynaud's phenomenon is an exaggeration of responses to cold or emotional stress. Primary RP is essentially mediated by microvascular vasospasm. Hyperactivation of the sympathetic system causes extreme vasoconstriction of the peripheral blood vessels, leading to hypoxia. Chronic, recurrent cases can result in atrophy of the skin, subcutaneous tissue, and muscle. It can also rarely result in ulceration and ischemic gangrene.

Traditional treatment options for Reynaud's phenomenon include prescription medication that dilates blood vessels and promotes circulation. These include calcium channel blockers, such as nifedipine or diltiazem; alpha blockers, which counteract the actions of norepinephrine, a hormone that constricts blood vessels, such as prazosin or doxazosin; and vasodilators, to relax blood vessels, such as nitroglycerin cream, or the angiotensin II inhibitor losartan, sildenafil, or prostaglandins. Fluoxetine, a selective serotonin reuptake inhibitor and other antidepressant medications may reduce the frequency and severity of episodes due to psychological stressors. These drugs may cause side effects such as headache, flushing and ankle edema. A drug may also lose effectiveness over time.

The regulation of cutaneous vasoconstriction and vasodilation involves altered sympathetic nerve activity and a number of neuronal regulators, including adrenergic and non-adrenergic, as well as REDOX signaling and other signaling such as the RhoA/ROCK pathway. Vasoconstriction of vascular smooth muscle cells (vSMC) in the skin is thought to be activated by norepinephrine mediated by alpha1 and alpha2 adrenoreceptors. Alpha2C-ARs translocate from the trans Golgi to the cell surface of the vSMC where they respond to stimulation and signaling of these responses involves the RhoA/Rhokinase (ROCK) signaling pathway. Cold stimulation in cutaneous arteries results in the immediate generation of reactive oxygen species (ROS) in the vSMC mitochondria. ROS are involved in the REDOX signaling through the RhoA/ROCK pathway. RhoA is a GTP-binding protein whose role is the regulation of actin-myosin dependent processes such as migration and cell contraction in vSMC. Non-adrenergic neuropeptides with known function in vasculature with possible involvement in RP include calcitonin gene-related peptide (CGRP), Substance P (SP), Neuropeptide Y (NPY), and vasoactive intestinal peptide (VIP). Fonseca et al., 2009, "Neuronal regulators and vascular dysfunction in Raynaud's phenomenon and systemic sclerosis", *Curr. Vascul. Pharmacol.* 7:34-39.

New therapies for RP include alpha-2c adrenergic receptor blockers, protein tyrosine kinase inhibitors, Rho-kinase inhibitors and calcitonin gene related peptide.

Calcitonin gene related peptide (CGRP) is a member of the calcitonin family of peptides and exists in two forms; alpha-CGRP and beta-CGRP. Alpha-CGRP is a 37-amino acid peptide formed from alternative splicing of the calcitonin/CGRP gene. CGRP is one of the most abundant peptides produced in peripheral and central neurons. It is a potent peptide vasodilator and can function in the transmission of pain. Migraine is a common neurological disorder that is associated with an increase in CGRP levels. CGRP dilates intracranial blood vessels and transmits vascular nociception. CGRP receptor antagonists have been tested as treatments for migraines. Arulmani et al., 2004, "Calcitonin gene-related peptide and it role in migraine pathophysiology", *Eur. J. Pharmacol.* 500(1-3): 315-330. At least three receptor subtypes have been identified and CGRP acts through G protein-coupled receptors whose presence and changes in function modulate the peptide's effect in various tissues. CGRP's signal transduction through the receptors is dependent on two accessory proteins: receptor activity modifying protein 1 (RAMP1) and receptor component protein (RCP). Ghatta 2004, Calcitonin gene-related peptide: understanding its role. *Indian J. Pharmacol.* 36(5): 277-283. One study of the effects of intravenous infusion of three vasodilators: endothelium-dependent vasodilator adenosine triphosphate (ATP), endothelium-independent vasodilator prostacyclin (epoprostenol; PGI2), and CGRP, to patients with Reynaud's phenomenon, and a similar number of age and sex matched controls, using laser Doppler flowmetry (LDF) showed CGRP induced flushing of the face and hands by a rise in skin blood flow in the Reynaud's patients, whereas in controls CGRP caused flushing only in the face. PGI2 caused similar rises in blood flow in hands and face of both groups. ATP did not cause any significant changes in blood flow in hands or face of the patients, but increased blood flow to the face of controls. Shawket et al., 1989, "Selective suprasensitivity to calcitonin-gene-related peptide in the hands in Reynaud's phenomenon". *The Lancet*, 334(8676):1354-1357. In one aspect, the wild-type protein target molecule is CGRP.

In one embodiment, the disclosure provides methods of selecting for conditionally active recombinant protein variants of proteins associated with Reynaud's syndrome to be reversibly deactivated at normal physiological temperature, but reactivated at the aberrant lower temperatures in digits. The conditionally active proteins can be used to treat Reynaud's phenomenon, to prevent or reduce loss of digit function due to low circulation.

Circulatory Disorders—Vasopressin

Arginine vasopressin (AVP, vasopressin, antidiuretic hormone (ADH)) is a peptide hormone found in most mammals that controls reabsorption of molecules in the tubules of the kidney by affecting tissue permeability. One of the most important roles of vasopressin is to regulate water retention in the body. In high concentrations it raises blood pressure by introducing moderate vasoconstriction. Vasopressin has three effects which result in increased urine osmolality (increased concentration) and decreased water excretion. First, vasopressin causes an increase in the permeability of water of the collecting duct cells in the kidney allowing water resorption and excretion of a smaller volume of concentrated urine (antidiuresis). This occurs through insertion of aquaporin-2 water channels into the apical membrane of the collecting duct cells. Secondly, vasopressin causes an increase in the permeability of the inner medullary portion of the collecting duct to urea, allowing increased reabsorption urea into the medullary interstitium. Thirdly, vasopressin causes stimulation of sodium and chloride reabsorption in the thick ascending limb of the loop of Heme by increasing the activity of the $Na^+$—$K^+$-$2Cl''$-cotransporter. NaCl reabsorption drives the process of countercurrent multiplication, which furnishes the osmotic gradient for aquaporin mediated water reabsorption in the medullary collecting ducts.

The hypertonic interstitial fluid surrounding the collecting ducts of the kidney provides a high osmotic pressure for the removal of water. Transmembrane channels made of proteins called aquaporins are inserted in the plasma membrane greatly increasing its permeability to water. When open, an aquaporin channel allows 3 billion molecules of water to pass through each second. Insertion of aquaporin-2 channels requires signaling by vasopressin. Vasopressin binds to receptors (called V2 receptors) on the basolateral surface of the cells of the collecting ducts. Binding of the hormone triggers a rising level of cAMP within the cell. This "second messenger" initiates a chain of events culminating in the insertion of aquaporin-2 channels in the apical surface of the collecting duct cells. The aquaporins allow water to move out of the nephron, increasing the amount of water re-absorbed from the forming urine back into the bloodstream.

The main stimulus for the release of vasopressin from the pituitary gland is increased osmolality of the blood plasma. Anything that dehydrates the body, such as perspiring heavily increases the osmotic pressure of the blood and turns on the vasopressin to V2 receptor to aquaporin-2 pathway. As a result, as little as 0.5 liters/day of urine may remain of the original 180 liters/day of nephric filtrate. The concentration of salts in urine can be as high as four times that of the blood. If the blood should become too dilute, as would occur from drinking a large amount of water, vasopressin secretion is inhibited and the aquaporin-2 channels are taken back into the cell by endocytosis. The result is that a large volume of watery urine is formed with a salt concentration as little as one-fourth of that of the blood.

Decreased vasopressin release or decreased renal sensitivity to AVP leads to diabetes insipidus, a condition featuring hypernatremia (increased blood sodium concentration), polyuria (excess urine production), and polydipsia (thirst).

High levels of AVP secretion (syndrome of inappropriate antidiuretic hormone, SIADH) and resultant hyponatremia (low blood sodium levels) occurs in brain diseases and conditions of the lungs (Small cell lung carcinoma). In the perioperative period, the effects of surgical stress and some commonly used medications (e.g., opiates, syntocinon, antiemetics) lead to a similar state of excess vasopressin secretion. This may cause mild hyponatremia for several days.

Vasopressin agonists are used therapeutically in various conditions, and its long-acting synthetic analogue desmopressin is used in conditions featuring low vasopressin secretion, as well as for control of bleeding (in some forms of von Willebrand disease) and in extreme cases of bedwetting by children. Terlipressin and related analogues are used as vasoconstrictors in certain conditions. Vasopressin infusion has been used as a second line of management in septic shock patients not responding to high dose of inotropes (e.g., dopamine or norepinephrine). A vasopressin receptor antagonist is an agent that interferes with action at the vasopressin receptors. They can be used in the treatment of hyponatremia.

In one embodiment, the disclosure provides methods to select for conditionally active biologic recombinant or synthetic protein variants of proteins involved in the vasopressin response to be reversibly deactivated at normal physiological osmotic pressure, but reactivated at aberrant osmotic pressure in the blood. In another embodiment, variants of proteins involved in the vasopressin response are activated under hyponatremic conditions, but inactivated at normal serum sodium concentrations. In one aspect, hyponatremic conditions are those where serum sodium <135 mEq/L.

Cancer—Angiostatin

Angiostatin is a naturally occurring protein in several animal species. It acts as an endogenous angiogenesis inhibitor (i.e., it blocks the growth of new blood vessels). Angiostatin is able to suppress tumor cell growth and metastasis through inhibition of endothelial cell proliferation and migration. Angiostatin is a 38 kD fragment of plasmin (which is itself a fragment of plasminogen). Angiostatin comprises the kringles 1 to 3 of plasminogen. Angiostatin is produced, for example, by autolytic cleavage of plasminogen, involving extracellular disulfide bond reduction by phosphoglycerate kinase. Angiostatin can also be cleaved from plasminogen by different matrix metalloproteinases (MMPs) including MMP2, MMP 12 and MMP9, and serine proteases (neutrophil elastase, prostate-specific antigen (PSA)). In vivo angiostatin inhibits tumor growth and keeps experimental metastasis in a dormant state. Angiostatin is elevated in animals with primary tumors and other inflammatory and degenerative diseases.

Angiostatin is known to bind many proteins including angiomotin and endothelial cell surface ATO synthase, but also integrins, annexin II, C-met receptor, NG2-proteoglycans, tissue-plasminogen activator, chondroitin sulfate glycoproteins, and CD26. One study shows that IL-12, a TH1 cytokine with potent antiangiogenic activity, is a mediator of angiostatin's activity. Albin"., *J. Translational Medicine*. Jan. 4, 2009, 7:5. Angiostatin binds and inhibits ATP synthase on the endothelial cell surface. ATP synthase also occurs on the surface of a variety of cancer cells. Tumor cell surface ATP synthase was found to be more active at low extracellular pH; a hallmark of tumor microenvironment. Angiostatin was found to affect tumor cell surface ATP synthase activity at acidic extracellular pH (pHe). At low extracellular pH, angiostatin was directly anti-tumorigenic. At low pH, angiostatin and anti-beta-subunit antibody induce intracellular acidification of A549 cancer cells, as well as a direct toxicity that is absent in tumor cells with low levels of extracellular ATP synthase. It was hypothesized that the mechanism of tumor cytotoxicity is dependent on intracellular pH deregulation due to inhibition of cell surface ATP synthase. Chi and Pizzo, "Angiostatin is directly cytotoxic to tumor cells at low extracellular pH: a mechanism dependent on cell surface-associated ATP synthase", *Cancer Res.*, 2006, 66(2): 875-82.

In one embodiment, the disclosure provides a method for identification of conditionally active angiostatin variant which is less active than wild-type angiostatin at normal physiological blood pH, but exhibits enhanced activity at low pH. Low pH is defined as being less than normal physiological pH. In one aspect, low pH is less than about pH 7.2. In a particular aspect, low pH is about pH 6.7.

In one aspect, the conditionally active angiostatin variant can be formulated and utilized as an anticancer agent.

Enhancement of Tissue Permeability—Hyaluronidase

Hyaluronidases are a family of enzymes that degrade hyaluronic acid. By catalyzing the degradation of hyaluronic acid, a major constituent of the interstitial barrier, hyaluronidase lowers the viscosity of hyaluronic acid, thereby increasing tissue permeability. It is used in medicine in conjunction with drugs to speed their dispersion and delivery. The most common application is in ophthalmic surgery, used in combination with local anesthetics. Animal derived hyaluronidase include Hydase™ (PrimaPharm Inc.; Akorn me), Vitrase (ISTA Pharmaceuticals) and Amphadase (Amphastar Pharmaceuticals). Human Recombinant Hyaluronidase is currently approved as an adjuvant to increase absorption of other drugs; hypodermocyclis (subcutaneous infusion of fluids); adjunct in subcutaneous urography to improve resorption of radioopaque agents. (Hylenex; Halozyme Therapeutics, Inc.; Baxter Healthcare Corp.) In one embodiment, hyaluronidase can serve as a wild-type protein (parent molecule) for preparation of a conditionally active biologic protein. Hyaluronidases may play a role in cancer metastasis and perhaps angiogenesis; therefore overexposure to these enzymes could be deleterious, in one aspect, a conditionally active biologic hyaluronidase protein would become irreversibly or reversibly inactivated at normal physiological temperature, but would be active at a level equal to or exceeding that of the wild-type hyaluronidase at certain temperature ranges below that of normal physiological temperature.

Autoimmune Diseases—Conditionally Active Biological Response Modifiers

Rheumatoid arthritis is an autoimmune disease characterized by aberrant immune mechanisms that lead to joint inflammation and swelling with progressive destruction of the joints. RA can also affect the skin, connective tissue and organs in the body. Traditional treatment includes non-steroidal anti-inflammatory drugs (NSAIDS), COX-2 inhibitors, and disease-modifying anti-rheumatic drugs (DMARDS) such as methotrexate. None of the traditional treatment regimes is ideal, especially for long term use.

Biological response modifiers, which target inflammatory mediators, offer a relatively new approach to the treatment of rheumatoid arthritis and other autoimmune diseases. Such biological response modifiers include antibodies, or active portions thereof, against various inflammatory mediators such as IL-6, IL-6 receptor, TNF-alpha, IL-23 and IL-12.

Some of the first biological response modifiers were medications targeting tumor necrosis factor alpha (TNF-a), a pro-inflammatory cytokine involved in the pathogenesis of RA. Several anti-TNF-alpha medications are currently marketed for the treatment of RA. For example, Enbrel® (etanercept, Amgen) is a TNF-alpha blocker. Etanercept is a dimeric fusion protein consisting of the extracellular ligand-binding portion of the human 75 kilodalton (p75) tumor necrosis factor receptor (TNFR) linked to the Fc portion of human IgG1. The Fc component of etanercept contains the CH2 domain, the CH3 domain and hinge region, but not the CH1 domain of IgG1. Etanercept is produced in a Chinese hamster ovary (CHO) mammalian cell expression system. It consists of 934 amino acids and an apparent molecular weight of about 150 kilodaltons. Enbrel® is used to treat rheumatoid arthritis, psoriatic arthritis, ankylosing spondylitis and plaque psoriasis. Serious side effects of Enbrel® include infections including tuberculosis, fungal infection, bacterial or viral infection due to opportunistic pathogens. Sepsis can also occur. Lymphoma or other malignancies have also been reported.

Remicade® (infliximab) is a chimeric anti-TNF-alpha IgGkI monoclonal antibody composed of human constant and murine variable regions. Remicade is administered by intravenous injection and is used to treat rheumatoid arthritis, psoriasis, Crohn's disease, ulcerative colitis, and ankylosing spondylitis. Side effects of Remicade include serious infection or sepsis, and rarely certain T-cell lymphomas. Other side effects include hepatotoxicity, certain severe hematologic events, hypersensitivity reactions and certain severe neurological events.

Other biological response modifiers include humanized anti-interleukin-6 (IL-6) receptor antibodies. IL-6 is a cytokine that contributes to inflammation, swelling and joint damage in RA. One humanized anti-IL-6 receptor antibody, Actemra (tocilizumab, Roche), is approved by the FDA and European Commission to treat adult patients with rheumatoid arthritis. Actemra is also approved in Japan for treatment of RA and juvenile idiopathic arthritis (sJIA). Phase III studies showed that treatment with Actemra as a monotherapy, or a combination with MTX or other DMARDs, reduced signs and symptoms of RA compared with other therapies. Actemra is a humanized anti-human IL-6 receptor monoclonal antibody that competitively blocks the binding of IL-6 to its receptor. Thus, it inhibits the proliferative effects of IL-6, which lead to synovial thickening and pannus formation in RA. Serious side effects of Actemra, include serious infections and hypersensitivity reactions including a few cases of anaphylaxis. Other side effects include upper respiratory tract infection, headache, nasopharyngitis, hypertension and increased ALT.

Another common autoimmune disease is psoriasis. An overactive immune system can lead to high levels of IL-12 and IL-23, two cytokine proteins that have been found in psoriatic skin plaques. IL-12 and IL-23 are involved in inflammatory and immune responses such as natural killer cell activation and CD4+ T-cell differentiation and activation.

One treatment for moderate or severe psoriasis involves subcutaneous injection of Stelara™ (ustekinumab, Centocor Ortho Biotech, Inc.) a humanized IgGIk monoclonal antibody against the p40 subunit of the IL-12 and IL-23 cytokines. Stelara has been shown to provide relief from certain symptoms associated with psoriatic plaques, such as plaque thickness, scaling and redness. The formulation for Stelara includes L-histidine and L-histidine monohydrochloride monohydrate, polysorbate 80, and sucrose in aqueous solution. Use of Stelara™ affects the immune system, and may increase chances of infection, including tuberculosis, and infections caused by bacteria, fungi or viruses; as well as increase the risk of certain types of cancer.

Side effects of the biological response modifiers are significant and are caused in part by high levels following injection into patients renders patients susceptible to serious infection or death. This is a major side effect associated with this important class of drugs. One challenge is avoiding the high initial level of activity from the dose of antibody required to provide a long treatment effect following injection.

In one embodiment, the disclosure provides a method to prepare a conditionally active biological response mediator, or fragment thereof, that avoids the high level of activity from the dose of antibody required to provide a long treatment effect following injection. The method of the disclosure can be used to design antibodies to inflammatory mediators such as IL-6, IL-6 receptor, TNF-alpha, IL-23 and IL-12 that are inactive at dosing conditions such as room temperature, but slowly refold (reversibly or irreversibly) at body temperature. These antibodies or fragments thereof would be inactive upon initial injection, but would refold or reactivate over a period of hours to days when exposed to blood following injection. This could allow higher dosing, and a longer half-life (or periods between dosing) with reduced side effects.

In one aspect, the disclosure provides a method for preparation of a conditionally active antibody to an inflammatory mediator, or fragment thereof, that is inactive at dosing conditions such as room temperature, but slowly refold (reversibly or irreversibly) at body temperature. The method comprises the following steps: selecting an inflammatory mediator, screening to identify an antibody to the inflammatory mediator via hybridoma, humanizing the anti-inflammatory mediator antibody, evolving the anti-inflammatory mediator antibody and screening differentially for binding at two or more conditions, for example, two or more temperature conditions such as at room temperature and at 37° C. or higher, selecting for mutations that are inactive at a first condition, relative to wild type, but show increased activity (e.g. binding) relative to the wild type antibody activity (binding) at a second condition. The up-mutants identified in the heavy and light changes are then recombined within the heavy and light chains, as well as through combinatorial association of the heavy and light chains. Screening of these recombined heavy and light chains is repeated at the two conditions, for example, room temperature and at 37° C. or higher. In addition, the recombined antibodies or fragments can be screened for activity and stability under storage and physiological conditions.

Alternatively, the wild-type antibody to the inflammatory mediator is a known antibody or variant or active fragment thereof.

In one aspect, the first and second conditions are selected from conditions of pH, osmotic pressure, osmolality, oxidative stress and electrolyte concentration. In another aspect, the inflammatory mediator is selected from IL-6, IL-6 receptor, TNF-alpha, IL-23 and IL-12.

In another aspect, the disclosure provides a method for preparation of a conditionally active antibody to IL-6, or fragment thereof, that is inactive at dosing conditions such as room temperature, but slowly refold (reversibly or irreversibly) at body temperature. The method comprises the following steps. Screening a fully human library for an antibody to IL-6. Evolving the IL-6 antibody and screening differentially for molecules at room temperature and at 37° C. or higher; selecting for mutations that are inactive at room temperature, relative to wild type, but show increased activity (e.g. binding) relative to the wild type antibody activity (binding). The up-mutants identified in the heavy and light changes are then recombined within the heavy and light chains, as well as through combinatorial association of the heavy and light chains. Screening of these recombined heavy and light chains is repeated at room temperature and the higher temperature. In addition, the recombined antibodies or fragments are tested for activity and stability under storage and physiological conditions.

The conditionally active anti-IL-6 antibodies thus identified and produced can be used in a method to treat an autoimmune disease, such as rheumatoid arthritis or psoriasis, by administration of an effective amount to a patient in need thereof, with a reduction in the severity of side effects compared to administration of a traditional biological response modifier anti-IL-6 antibody. One advantage of this method is that it allows for smoothing or leveling of the drug quantity over the period of treatment relative to the current high level of biological response modifier drug followed by half-life clearance over weeks or months.

Selection of a Wild-Type Protein from a Library

The wild-type protein may be selected from a wild-type protein library, such as a bacteriophage display library. In such embodiments, a large number of candidates for the wild-type protein are expressed in a bacteriophage library, particularly by a surface display technique. The candidates from the library are screened for a suitable wild-type protein. A typical bacteriophage library may contain bacteriophages expressing the candidates in a bacterial host. In one embodiment, the bacteriophage library may include a plurality of bacteriophages.

To construct a bacteriophage library, typically filamentous bacteriophages, such as the filamentous coliphage M13 are genetically modified by inserting oligonucleotides encoding the candidates to a coding sequence of one of the bacteriophage coat proteins. The coat proteins of the bacteriophage particles are consequently expressed with the candidates such that the candidates are displayed on the surface of bacteriophage particles. The displayed candidates may then be screened for the suitable wild-type protein.

One common technique for screening for a suitable wild-type protein is by immobilizing a bacteriophage particle with a desired candidate on a support. The support may be a plastic plate coated with a "bait" that can bind with the desirable candidates. Non-binding bacteriophage particles may be washed away from the plate. Bacteriophage particles binding to the plate (with desirable candidates) are eluted by washing and the eluted bacteriophage particles are amplified in bacteria. The sequence(s) encoding the candidates in the selected bacteriophage particles may then be determined by sequencing. The relationship between the candidate and bait may be, for example, a ligand-receptor or antigen-antibody relationship.

Another common technique of screening for a suitable wild-type protein is by use of an enzymatic assay of individual bacteriophage clones for a desired enzymatic activity exhibited by the candidates. Depending on the specific enzymatic activity, a person skilled in the art can design an appropriate assay to screen for candidates with the desired level of enzymatic activity.

In some embodiments, the bacteriophage library is provided as an array, such that each bacteriophage clone occupies a specific location on the array. Such an array can be provided on a solid support, for example, a membrane, an agar plate or a microtiter plate, in which case each bacteriophage clone of the library is attached or adhered thereto in a specific predetermined position on the solid support. In the case of agar plates, such plates preferably include bacterial growth media so as to support bacterial growth. When the array is provided on a membrane, for example, a nitrocellulose or a nylon membrane, a bacterial culture is applied onto the membrane and the membrane is soaked with nutrient growth media. In addition, the bacteriophage clones can also be provided on beads, in which case a single bacteriophage clone can be adhered to a single bead. Alternatively the bacteriophage clones can each be provided on an end of an optic fiber, in which case the fiber is used to optically communicate ultraviolet radiation from a light source.

A typical bacteriophage library may contain from $10^6$ to $10^{10}$ recombinant bacteriophages, each of which is distinguished by a coat protein (e.g. gp3 or gp8 in the case of phage M13) bearing a different candidate. The bacterial hosts for the bacteriophage library may be selected from bacterial genera including, for example, *Salmonella, Staphylococcus, Streptococcus, Shigella, Listeria, Campy icbacter, Klebsiella, Yersinia, Pseudomonas* and *Escherichia*.

The oligonucleotides encoding the candidates may be a collection of cDNAs that encode wild-type proteins. Methods are known for synthesizing cDNAs from a biological sample whereby a suitable wild-type protein may be expressed. Any genetic information that manifests physiological activity through transcripts may be harvested as cDNAs. When producing cDNAs, it is essential to synthesize full-length cDNAs. There are several methods that may be used to synthesize full-length cDNAs. For example, suitable methods include a method utilizing a Cap binding protein of yeast or Hela cells for labeling the 5' Cap site (I. Edery et al., "An Efficient Strategy To Isolate Full-length cDNAs Based on a mRNA Cap Retention Procedure (CAPture)", *Mol. Cell. Biol.*, vol. 15, pages 3363-3371, 1995); and a method where phosphates of incomplete cDNAs without 5' Cap are removed by using alkaline phosphatase and then the whole cDNAs are treated with a de-capping enzyme of a tobacco mosaic virus so that only the full-length cDNAs have phosphates (K. Maruyama et al., "Oligocapping: a simple method to replace the cap structure of eukaryotic mRNAs with oligoribonucleotides", Gene, vol. 138, pages 171-174, 1995 and S. Kato et al., "Construction of a human full-length cDNA bank", *Gene*, vol. 150, pages 243-250, 1995).

The library of candidates for the wild-type protein may also be produced using recombinant antibodies derived from a complete antibody repertoire of an organism. The genetic information representing the repertoire is assembled into large collections of full antibodies that can be screened for a suitable wild-type antibody with the desired antigen binding activity and/or one or more other functional characteristics. In some embodiments, B-cells from an animal immunized with an antigen, such as human, mouse, or rabbit B-cells are isolated. mRNAs from the isolated B-cells are collected (converted to cDNA) and sequenced. The most frequent cDNA fragments encoding a light chain and the most frequent cDNA fragments encoding a heavy chain are assembled into antibodies. In one embodiment, the 100 most frequent cDNA fragments encoding a light chain and the 100 most frequent cDNA fragments encoding a heavy chain are assembled to produce antibodies. In another embodiment, the most frequent cDNA fragments only encode the variable regions of the heavy chain and the variable regions of the light chain, thus the assembled antibodies contain only the variable regions but not the constant regions.

In some embodiments, including those from the mRNA isolated from B-cells, cDNA fragments encoding the variable regions of an IgG heavy chain are assembled with the most frequent IgK or IgK variable regions of the light chain. The assembled antibodies contain a heavy chain variable region from IgG and a light chain variable region from IgK or IgK.

The cDNAs encoding the assembled antibodies are then cloned and expressed, preferably in a plate-based format. The binding activity of the expressed antibodies may be assayed with a bead-based ELISA assay and a suitable wild-type antibody may be selected based on the ELISA assay. The cDNAs encoding the assembled antibodies may also expressed in a bacteriophage display library, which may then be screened for one or more desirable wild-type antibodies by any one of the techniques disclosed herein.

In embodiments where the wild-type protein is an antibody, the wild-type antibody preferably has particular characteristics that make it easier to evolve into a conditionally active antibody. In certain embodiments, the wild-type antibody may have similar binding activity and/or characteristics under both the normal physiological condition and an aberrant condition. In such embodiments, the wild-type antibody is selected based on having the most similar binding activity and/or the most similar combination of one or more characteristics under both the normal physiological condition and the aberrant condition. For example, if the normal physiological condition and aberrant condition are pH 7.4 and pH 6.0 respectively, the wild-type antibody that has the most similar binding activity at pH 7.4 and 6.0, may be selected over an antibody having a less similar binding activity at pH 7.4 and 6.0.

After the wild-type protein is selected, the DNA encoding the wild-type protein is evolved using a suitable mutagenesis technique to produce mutant DNAs, which may then be expressed to produce mutant proteins for screening to identify a conditionally active biologic protein. In some embodiments, the evolution may be minimal, e.g. only a small number of mutations are introduced to a wild-type protein in order to produce a mutant protein with the desired conditional activity. For example, less than 20 changes, possibly less than 18 changes introduced by CPE at each site may be sufficient to produce a suitable conditionally active biologic protein. For CPS, a combination of less than 6 up-mutations, or less than 5 up-mutations, or less than 4 up-mutations, or less than 3 up-mutations, or less than 2 up-mutations in the wild-type protein may be sufficient to produce a desirable conditionally active biologic protein.

In some embodiments, the evolving and expressing steps may be unnecessary when the library of wild-type proteins (e.g. the bacteriophage library and/or a recombinant antibody library) is sufficiently large. Such a large library may contain a wild-type protein with the conditionally active characteristics (with both a low activity in an assay under the normal physiological condition and a high activity in an assay under the aberrant condition). In these embodiments, the wild-type proteins in the library are subjected to the selecting step to discover a conditionally active biologic protein that is less active in the assay under the normal physiologic condition than the same protein in the assay under the aberrant condition. In one embodiment, the wild-type proteins in the library are individually subjected to an assay under a normal physiological condition and to an assay under an aberrant condition, together with the reference protein. The conditionally active biologic protein that is selected from the library is one which exhibits a lower activity under the normal physiological condition in comparison with the activity of the same protein under the aberrant condition. In this embodiment, because the library is sufficiently large and a wild-type protein with the conditionally active characteristics exists in the library already, no evolution of the wild-type proteins is necessary in order to discover a conditionally active biologic protein In some embodiments, the selecting step may use a reference protein for comparison. The reference protein may not be conditionally active in that it has a similar or the same activity under both the normal physiological condition and the aberrant condition. The reference protein is the same type of protein as the wild-type proteins in the library, e.g., the same type of enzyme, antibody or functional peptide. The reference protein may also be the same type of tissue plasminogen activator, streptokinase, urokinase, renin, hyaluronidase, calcitonin gene-related peptide (CGRP), substance P (SP), neuropeptide Y (NPY), vasoactive intestinal peptide (VTP), vasopressin or angiostatin. For instance, when the library contains a large number of wild-type antibodies against an antigen, the reference protein is an antibody against the same antigen with the same or similar activity for binding to the antigen at both the normal physiological condition and the aberrant condition.

Therefore, in one embodiment, the wild-type proteins in the library are individually subjected to an assay under a normal physiological condition and to an assay under an aberrant condition, together with the reference protein. The conditionally active biologic protein is selected from the library which exhibits both (a) a decreased activity under the normal physiological condition in comparison with the reference protein, and (b) an increased activity under the aberrant condition in comparison with the reference protein.

Methods of Generating Conditionally Active Biologic Proteins

One or more mutagenesis techniques are employed to evolve the DNA which encodes the wild-type protein to create a library of mutant DNA; the mutant DNA is expressed to create a library of mutant proteins; and the library is subjected to a screening assay under a normal physiological condition and under one or more aberrant conditions. Conditionally active biologic proteins are selected from those proteins which exhibit both (a) a decrease in activity in the assay at the normal physiological condition compared to the wild-type protein, and (b) an increase in activity in the assay under the aberrant condition compared to the wild-type protein. Alternatively, conditionally active biologic proteins are selected from those proteins which exhibit changes in activity, reversibly or irreversibly, in two or more different physiological conditions. In some embodiments, the wild-type protein is an antibody.

In some embodiments, the protein to be evolved may be a fragment of a wild-type protein or a fragment of a wild-type antibody. In some other embodiments, the protein to be evolved may be a protein selected by a mutagenesis process where the protein is selected for having a desired property such as a high binding affinity, a high expression level or humanization. The selected protein, which in this case is not a wild-type protein, may be used as the protein to be evolved in the method disclosed herein. In such embodiments, the method of the present invention comprises: selecting a protein from wild-type protein, a fragment of a wild-type protein and a mutated protein, evolving the DNA encoding the selected protein to produce mutant DNAs, expressing the mutant DNAs to produce mutant proteins, screening the mutant proteins to produce a conditionally active biologic protein which exhibits both: (a) a decrease in activity in an assay at the normal physiological condition compared to the selected protein, and (b) an increase in activity in the assay under the aberrant condition as compared to the selected protein.

Generation of Evolved Molecules from a Parent Molecule

Conditionally active biologic proteins can be generated through a process of mutagenesis and screening for individual mutations for a reduction in activity at the wild-type condition with activity at non wild-type conditions remaining the same or better than the activity at the wild-type condition.

The disclosure provides for a method for generating a nucleic acid variant encoding a polypeptide having enzyme activity, wherein the variant has an altered biological activity from that which naturally occurs, the method comprising (a) modifying the nucleic acid by (i) substituting one or more nucleotides for a different nucleotide, wherein the nucleotide comprises a natural or non-natural nucleotide; (ii) deleting one or more nucleotides, (iii) adding one or more nucleotides, or (iv) any combination thereof. In one aspect, the non-natural nucleotide comprises inosine. In another aspect, the method further comprises assaying the polypeptides encoded by the modified nucleic acids for altered enzyme activity, thereby identifying the modified nucleic acid(s) encoding a polypeptide having altered enzyme activity. In one aspect, the modifications of step (a) are made by PCR, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis, ligase chain reaction, in vitro mutagenesis, ligase chain reaction, oligonucleotide synthesis, any DNA-generating technique and any combination thereof. In another aspect, the method further comprises at least one repetition of the modification step (a).

The disclosure further provides a method for making a polynucleotide from two or more nucleic acids, the method comprising: (a) identifying regions of identity and regions of diversity between two or more nucleic acids, wherein at least one of the nucleic acids comprises a nucleic acid of the disclosure; (b) providing a set of oligonucleotides which correspond in sequence to at least two of the two or more nucleic acids; and, (c) extending the oligonucleotides with a polymerase, thereby making the polynucleotide.

Any technique of mutagenesis can be employed in various embodiments of the disclosure. Stochastic or random mutagenesis is exemplified by a situation in which a parent molecule is mutated (modified or changed) to yield a set of progeny molecules having mutation(s) that are not predetermined. Thus, in an in vitro stochastic mutagenesis reaction, for example, there is not a particular predetermined product whose production is intended; rather there is an uncertainty—hence randomness—regarding the exact nature of the mutations achieved, and thus also regarding the products generated. Stochastic mutagenesis is manifested in processes such as error-prone PCR and stochastic shuffling, where the mutation(s) achieved are random or not predetermined. The variant forms can be generated by error-prone transcription, such as an error-prone PCR or use of a polymerase which lacks proof-reading activity (see, Liao (1990) *Gene* 88: 107-111), of the first variant form, or, by replication of the first form in a mutator strain (mutator host cells are discussed in further detail below, and are generally well known). A mutator strain can include any mutants in any organism impaired in the functions of mismatch repair. These include mutant gene products of mutS, mutT, mutH, mutL, ovrD, dcm, vsr, umuC, umuD, sbcB, recJ, etc. The impairment is achieved by genetic mutation, allelic replacement, selective inhibition by an added reagent such as a small compound or an expressed antisense RNA, or other techniques. Impairment can be of the genes noted, or of homologous genes in any organism.

Current mutagenesis methods in widespread use for creating alternative proteins from a starting molecule are oligonucleotide-directed mutagenesis technologies, error-prone polymerase chain reactions (error-prone PCR) and cassette mutagenesis, in which the specific region to be optimized is replaced with a synthetically mutagenized oligonucleotide. In these cases, a number of mutant sites are generated around certain sites in the original sequence.

In oligonucleotide-directed mutagenesis, a short sequence is replaced with a synthetically mutagenized oligonucleotide. In oligonucleotide-directed mutagenesis, a short sequence of the polynucleotide is removed from the polynucleotide using restriction enzyme digestion and is replaced with a synthetic polynucleotide in which various bases have been altered from the original sequence. The polynucleotide sequence can also be altered by chemical mutagenesis. Chemical mutagens include, for example, sodium bisulfite, nitrous acid, hydroxylamine, hydrazine or formic acid. Other agents which are analogues of nucleotide precursors include nitrosoguanidine, 5-bromouracil, 2-aminopurine, or acridine. Generally, these agents are added to the PCR reaction in place of the nucleotide precursor thereby mutating the sequence. Intercalating agents such as proflavine, acriflavine, quinacrine and the like can also be used. Random mutagenesis of the polynucleotide sequence can also be achieved by irradiation with X-rays or ultraviolet light. Generally, plasmid polynucleotides so mutagenized are introduced into *E. coli* and propagated as a pool or library of hybrid plasmids.

Error-prone PCR uses low-fidelity polymerization conditions to introduce a low level of point mutations randomly over a long sequence. In a mixture of fragments of unknown sequence, error-prone PCR can be used to mutagenize the mixture.

In cassette mutagenesis, a sequence block of a single template is typically replaced by a (partially) randomized sequence. Reidhaar-Olson J F and Sauer R T: Combinatorial cassette mutagenesis as a probe of the informational content of protein sequences. *Science* 241(4861):53-57, 1988.

Alternatively, any technique of non-stochastic or non-random mutagenesis can be employed in various embodiments of the disclosure. Non-stochastic mutagenesis is exemplified by a situation in which a parent molecule is mutated (modified or changed) to yield a progeny molecule having one or more predetermined mutations. It is appreciated that the presence of background products in some quantity is a reality in many reactions where molecular processing occurs, and the presence of these background products does not detract from the non-stochastic nature of a mutagenesis process having a predetermined product. Site-saturation mutagenesis and synthetic ligation reassembly, are examples of mutagenesis techniques where the exact chemical structure(s) of the intended product(s) are predetermined.

One method of site-saturation mutagenesis is disclosed in U.S. patent application publication 2009/0130718. This method provides a set of degenerate primers corresponding to codons of a template polynucleotide, and performs polymerase elongation to produce progeny polynucleotides, which contain sequences corresponding to the degenerate primers. The progeny polynucleotides can be expressed and screened for directed evolution. Specifically, this is a method for producing a set of progeny polynucleotides, comprising the steps of (a) providing copies of a template polynucleotide, each comprising a plurality of codons that encode a template polypeptide sequence; and (b) for each codon of the template polynucleotide, performing the steps of (1) providing a set of degenerate primers, where each primer comprises a degenerate codon corresponding to the codon of the template polynucleotide and at least one adjacent sequence that is homologous to a sequence adjacent to the codon of the template polynucleotide; (2) providing conditions allowing the primers to anneal to the copies of the template polynucleotides; and (3) performing a polymerase elongation reaction from the primers along the template; thereby producing progeny polynucleotides, each of which contains a sequence corresponding to the degenerate codon of the annealed primer; thereby producing a set of progeny polynucleotides.

Site-saturation mutagenesis relates to the directed evolution of nucleic acids and screening of clones containing the evolved nucleic acids for resultant activity(ies) of interest, such nucleic acid activity(ies) &/or specified protein, particularly enzyme, activity(ies) of interest.

Mutagenized molecules provided by this technique may have chimeric molecules and molecules with point mutations, including biological molecules that contain a carbohydrate, a lipid, a nucleic acid, &/or a protein component, and specific but non-limiting examples of these include antibiotics, antibodies, enzymes, and steroidal and non-steroidal hormones.

Site saturation mutagenesis relates generally to a method of: 1) preparing a progeny generation of molecule(s) (including a molecule that is comprised of a polynucleotide sequence, a molecule that is comprised of a polypeptide sequence, and a molecule that is comprised in part of a polynucleotide sequence and in part of a polypeptide sequence), that is mutagenized to achieve at least one point mutation, addition, deletion, &/or chimerization, from one or more ancestral or parental generation template(s); 2) screening the progeny generation molecule(s)—preferably using a high throughput method—for at least one property of interest (such as an improvement in an enzyme activity or an increase in stability or a novel chemotherapeutic effect); 3) optionally obtaining and/or cataloguing structural and/or and functional information regarding the parental &/or progeny generation molecules; and 4) optionally repeating any of steps 1) to 3).

In site saturation mutagenesis, there is generated (e.g. from a parent polynucleotide template)—in what is termed "codon site-saturation mutagenesis"—a progeny generation of polynucleotides, each having at least one set of up to three contiguous point mutations (i.e. different bases comprising a new codon), such that every codon (or every family of degenerate codons encoding the same amino acid) is represented at each codon position. Corresponding to, and encoded by, this progeny generation of polynucleotides, there is also generated a set of progeny polypeptides, each having at least one single amino acid point mutation. In a preferred aspect, there is generated, in what is termed "amino acid site-saturation mutagenesis," one such mutant polypeptide for each of the 19 naturally encoded polypeptide-forming alpha-amino acid substitutions at each and every amino acid position along the polypeptide. This yields for each and every amino acid position along the parental polypeptide, a total of 20 distinct progeny polypeptides including the original amino acid, or potentially more than 21 distinct progeny polypeptides if additional amino acids are used either instead of or in addition to the 20 naturally encoded amino acids.

Other mutagenesis techniques can also be employed which involve recombination and more specifically a method for preparing polynucleotides encoding a polypeptide by a method of in vivo re-assortment of polynucleotide sequences containing regions of partial homology, assembling the polynucleotides to form at least one polynucleotide and screening the polynucleotides for the production of polypeptide(s) having a useful property.

In another aspect, mutagenesis techniques exploit the natural property of cells to recombine molecules and/or to mediate reductive processes that reduce the complexity of sequences and extent of repeated or consecutive sequences possessing regions of homology.

Various mutagenesis techniques can be used alone or in combination to provide a method for generating hybrid polynucleotides encoding biologically active hybrid polypeptides with enhanced activities. In accomplishing these and other objects, there has been provided, in accordance with one aspect of the disclosure, a method for introducing polynucleotides into a suitable host cell and growing the host cell under conditions that produce a hybrid polynucleotide.

Chimeric genes have been made by joining 2 polynucleotide fragments using compatible sticky ends generated by restriction enzyme(s), where each fragment is derived from a separate progenitor (or parental) molecule. Another example is the mutagenesis of a single codon position (i.e. to achieve a codon substitution, addition, or deletion) in a parental polynucleotide to generate a single progeny polynucleotide encoding for a single site-mutagenized polypeptide.

Further, in vivo site specific recombination systems have been utilized to generate hybrids of genes, as well as random methods of in vivo recombination, and recombination between homologous but truncated genes on a plasmid. Mutagenesis has also been reported by overlapping extension and PCR.

Non-random methods have been used to achieve larger numbers of point mutations and/or chimerizations, for example comprehensive or exhaustive approaches have been used to generate all the molecular species within a particular grouping of mutations, for attributing functionality to specific structural groups in a template molecule (e.g. a specific single amino acid position or a sequence comprised of two or more amino acids positions), and for categorizing and comparing specific grouping of mutations.

Any of these or other methods of evolving can be employed in the present disclosure to generate a new population of molecules (library) from one or more parent molecules.

Once formed, the constructs may, or may not be size fractionated on an agarose gel according to published protocols, inserted into a cloning vector, and transfected into an appropriate host cell.

Expression of Evolved Molecules

Once a library of mutant molecules is generated, DNA can be expressed using routine molecular biology techniques. Thus, protein expression can be directed using various known methods.

For example, briefly, a wild type gene can be evolved using any variety of random or non-random methods such as those indicated herein. Mutant DNA molecules are then digested and ligated into vector DNA, such as plasmid DNA using standard molecular biology techniques. Vector DNA containing individual mutants is transformed into bacteria or other cells using standard protocols. This can be done in an individual well of a multi-well tray, such as a 96-well tray for high throughput expression and screening. The process is repeated for each mutant molecule.

Polynucleotides selected and isolated as described are introduced into a suitable host cell. A suitable host cell is any cell which is capable of promoting recombination and/or reductive reassortment. The selected polynucleotides are preferably already in a vector which includes appropriate control sequences. The host cell can be a higher eukaryotic cell, such as a mammalian cell, or a lower eukaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation (e.g. Ecker and Davis, 1986, Inhibition of gene expression in plant cells by expression of antisense RNA, *Proc. Natl. Acad. Sci. USA,* 83:5372-5376).

As representative examples of expression vectors which may be used, there may be mentioned viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus and yeast). Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present disclosure.

The DNA sequence in the expression vector is operatively linked to an appropriate expression control sequence(s) (promoter) to direct RNA synthesis. Particular named bacterial promoters include lad, lacZ, T3, T7, gpt, lambda PR, PL and trp. Eukaryotic promoters include CMV immediate early, HSV thymidine kinase, early and late SV40, LTRs from retrovirus, and mouse metallothionein-1. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using chloramphenicol transferase (CAT) vectors or other vectors with selectable markers. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

Therefore, in another aspect of the disclosure, novel polynucleotides can be generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of novel molecular species. Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

In one aspect, the host organism or cell comprises a gram negative bacterium, a gram positive bacterium or a eukaryotic organism. In another aspect of the disclosure, the gram negative bacterium comprises *Escherichia coli*, or *Pseudomonas fluorescens*. In another aspect of the disclosure, the gram positive bacterium comprise *Streptomyces diversa, Lactobacillus gasseri, Lactococcus lactis, Lactococcus cremoris,* or *Bacillus subtilis*. In another aspect of the disclosure, the eukaryotic organism comprises *Saccharomyces cerevisiae, Schizosaccharomyces pombe, Pichia pastoris, Kluyveromyces lactis, Hansenula plymorpha,* or *Aspergillus niger*. As representative examples of appropriate hosts, there may be mentioned: bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; and plant cells. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described in "SV40-transformed simian cells support the replication of early SV40 mutants" (Gluzman, 1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 splice, and polyadenylation sites may be used to provide the required non-transcribed genetic elements.

The cells are then propagated and "reductive reassortment" is effected. The rate of the reductive reassortment process may be stimulated by the introduction of DNA damage if desired, in vivo reassortment is focused on "inter-molecular" processes collectively referred to as "recombination" which in bacteria, is generally viewed as a "RecA-dependent" phenomenon. The disclosure can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process. The end result is a reassortment of the molecules into all possible combinations.

Host cells containing the polynucleotides of interest can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan.

Protein expression can be induced by a variety of known methods, and many genetic systems have been published for induction of protein expression. For example, with appropriate systems, the addition of an inducing agent will induce protein expression. Cells are then pelleted by centrifugation and the supernatant removed. Periplasmic protein can be enriched by incubating the cells with DNAse, RNAse, and lysozyme. After centrifugation, the supernatant, containing the new protein, is transferred to a new multi-well tray and stored prior to assay.

Cells are typically harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

The clones which are identified as having the desired activity may then be sequenced to identify the polynucleotide sequence encoding an enzyme having the enhanced activity.

The polypeptides that are identified from such libraries can be used for therapeutic, diagnostic, research and related purposes, and/or can be subjected to one or more additional cycles of shuffling and/or selection. The disclosure provides for a fragment of the conditionally active biologic protein which is at least 10 amino acids in length, and wherein the fragment has activity.

The disclosure provides for a codon-optimized polypeptide or a fragment thereof, having enzyme activity, wherein the codon usage is optimized for a particular organism or cell. Narum et al., "Codon optimization of gene fragments encoding *Plasmodium falciparum* merzoite proteins enhances DNA vaccine protein expression and immunogenicity in mice". *Infect. Immun.* 2001 December, 69(12): 7250-3 describes codon-optimization in the mouse system. Outchkourov et al., "Optimization of the expression of Equistatin in *Pichia pastoris*, protein expression and purification", *Protein Expr. Purif.* 2002 February; 24(1): 18-24 describes codon-optimization in the yeast system. Feng et al., "High level expression and mutagenesis of recombinant human phosphatidylcholine transfer protein using a synthetic gene: evidence for a C-terminal membrane binding domain" *Biochemistry* 2000 Dec. 19, 39(50): 15399-409 describes codon-optimization in *E. coli*. Humphreys et al., "High-level periplasmic expression in *Escherichia coli* using a eukaryotic signal peptide: importance of codon usage at the 5' end of the coding sequence", *Protein Expr. Purif.* 2000 Nov. 20(2):252-64 describes how codon usage affects secretion in *E. coli*.

The evolution of a conditionally active biologic protein can be aided by the availability of a convenient high throughput screening or selection process.

Once identified, polypeptides and peptides of the disclosure can be synthetic, or be recombinantly generated polypeptides. Peptides and proteins can be recombinantly expressed in vitro or in vivo. The peptides and polypeptides of the disclosure can be made and isolated using any method known in the art. Polypeptide and peptides of the disclosure can also be synthesized, whole or in part, using chemical methods well known in the art. See e.g., Caruthers (1980) "New chemical methods for synthesizing polynucleotides", *Nucleic Acids Res. Symp. Ser.* 215-223; Horn (1980), "Synthesis of oligonucleotides on cellulose. Part II: design and synthetic strategy to the synthesis of 22 oligodeoxynucleotides coding for Gastric Inhibitory Polypeptide (GIP)[1]", *Nucleic Acids Res. Symp. Ser.* 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) "A strategy for a convergent synthesis of N-linked glycopeptides on a solid support", *Science* 269: 202; Merrifield (1997) "Concept and early development of solid-phase peptide synthesis", *Methods Enzymol.* 289:3-13) and automated synthesis may be achieved, e.g., using the ABI 43 IA Peptide Synthesizer (Perkin Elmer) in accordance with the instructions provided by the manufacturer.

The peptides and polypeptides of the disclosure can also be glycosylated. The glycosylation can be added post-translationally, either chemically or by cellular biosynthetic mechanisms, wherein the latter incorporates the use of known glycosylation motifs, which can be native to the sequence or can be added as a peptide or added in the nucleic acid coding sequence. The glycosylation can be O-linked or N-linked.

The peptides and polypeptides of the disclosure, as defined above, include all "mimetic" and "peptidomimetic" forms. The terms "mimetic" and "peptidomimetic" refer to a synthetic chemical compound which has substantially the same structural and/or functional characteristics of the polypeptides of the disclosure. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the disclosure which are conservative variants, routine experimentation will determine whether a mimetic is within the scope of the disclosure, i.e., that its structure and/or function is not substantially altered.

Polypeptide mimetic compositions of the disclosure can contain any combination of non-natural structural components. In alternative aspect, mimetic compositions of the disclosure include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the disclosure can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., –C(.dbd.O)–CH.sub.2– for —C(.dbd.O)–NH—), aminomethylene (CH.sub.2-NH), ethylene, olefin (CH.dbd.CH), ether (CH.sub.2–O), thioether (CH.sub.2–S), tetrazole (CN.sub.4-), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, N. Y.).

A polypeptide of the disclosure can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3- pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; D- or L-p-methoxy-biphenylphenylalanine; D- or L-2-indole(alkyl) alanines; and, D- or L-alkylanines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R—N=C=N—R') such as, e.g., 1-cyclohexyl-3-(2-moφholinyl-(4-ethyl) carbodiimide or 1-ethyl-3(4-azonia-4, 4-dimetholpentyl) carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, preferably under alkaline conditions. Tyrosine residue mimetics can be generated by reacting tyrosyl with, e.g., aromatic diazonium compounds or tetranitromethane. N-acetylimidazole and tetranitromethane can be used to form 0-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A residue, e.g., an amino acid, of a polypeptide of the disclosure can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

The disclosure also provides methods for modifying the polypeptides of the disclosure by either natural processes, such as post-translational processing (e.g., phosphorylation, acylation, etc), or by chemical modification techniques. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, PEGylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd Ed., W. H. Freeman and Company, New York (1993); Posttranslational Covalent Modification of Proteins, B. C. Johnson, Ed., Academic Press, New York, pp. 1-12 (1983).

Solid-phase chemical peptide synthesis methods can also be used to synthesize the polypeptide or fragments of the disclosure. Such methods have been known in the art since the early 1960's (Merrifield, R. B., "Solid-phase synthesis. I. The synthesis of a tetrapeptide", *J. Am. Chem. Soc,* 85:2149-2154, 1963) (See also Stewart, J. M. and Young, J. D., Solid Phase Peptide Synthesis, 2nd Ed., Pierce Chemical Co., Rockford, 111, pp. 11-12)) and have recently been employed in commercially available laboratory peptide design and synthesis kits (Cambridge Research Biochemicals). Such commercially available laboratory kits have generally utilized the teachings of H. M. Geysen et al., "Use of peptide synthesis to probe viral antigens for epitopes to a resolution of a single amino acid," *Proc. Natl. Acad. Sci., USA,* 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431 A™ automated peptide synthesizer. Such equipment provides ready access to the peptides of the disclosure, either by direct synthesis or by synthesis of a series of fragments that can be coupled using other known techniques.

The synthetic polypeptide or fragment thereof can be recovered and purified by known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

The disclosure provides for a conditionally active protein variant preparation or formulation which comprises at least one of the protein variants, wherein the preparation is liquid or dry. The protein formulation optionally includes a buffer, cofactor, second or additional protein, or one or more excipients. In one aspect the formulation is utilized as a therapeutic conditionally active biologic protein which is active under aberrant or non-physiological conditions, but less active or inactive under normal physiological conditions of, e.g., temperature, pH, or osmotic pressure, oxidative stress or osmolality.

Standard purification techniques can be employed for either recombinant or synthetic conditionally active biologic proteins.

Screening of Mutants to Identify Reversible or Non-Reversible Mutants

Identifying desirable molecules is most directly accomplished by measuring protein activity at the permissive condition and the wild type condition. The mutants with the largest ratio of activity (permissive/wild type) can then be selected and permutations of the point mutations are generated by combining the individual mutations using standard methods. The combined permutation protein library is then screened for those proteins displaying the largest differential activity between the permissive and wild type condition.

Activity of supernatants can be screened using a variety of methods, for example using high throughput activity assays, such as fluorescence assays, to identify protein mutants that are sensitive at whatever characteristic one desires (temperature, pH, etc). For example, to screen for temporally sensitive mutants, the enzymatic or antibody activity of each individual mutant is determined at lower temperatures (such as 25 degrees Celsius), and at temperatures which the original protein functions (such as 37 degrees Celsius), using commercially available substrates. Reactions can initially be performed in a multi well assay format, such as a 96-well assay, and confirmed using a different format, such as a 14 ml tube format.

The disclosure further provides a screening assay for identifying a enzyme, the assay comprising: (a) providing a plurality of nucleic acids or polypeptides; (b) obtaining polypeptide candidates to be tested for enzyme activity from the plurality; (c) testing the candidates for enzyme activity; and (d) identifying those polypeptide candidates which exhibit elevated enzyme activity under aberrant or non-physiological conditions, and decreased enzyme activity compared to the wild-type enzyme protein under normal physiological conditions of, e.g., temperature, pH, oxidative stress, osmolality, electrolyte concentration or osmotic pressure.

In one aspect, the method further comprises modifying at least one of the nucleic acids or polypeptides prior to testing the candidates for conditional biologic activity, in another aspect, the testing of step (c) further comprises testing for improved expression of the polypeptide in a host cell or host organism, in a further aspect, the testing of step (c) further comprises testing for enzyme activity within a pH range from about pH 3 to about pH 12. In a further aspect, the testing of step (c) further comprises testing for enzyme activity within a pH range from about pH 5 to about pH 10. In a further aspect, the testing of step (c) further comprises testing for enzyme activity within a pH range from about pH 6 to about pH 8. In a further aspect, the testing of step (c) further comprises testing for enzyme activity at pH 6.7 and pH 7.5. In another aspect, the testing of step (c) further comprises testing for enzyme activity within a temperature range from about 4 degrees C. to about 55 degrees C. In another aspect, the testing of step (c) further comprises testing for enzyme activity within a temperature range from about 15 degrees C. to about 47 degrees C. In another aspect, the testing of step (c) further comprises testing for enzyme activity within a temperature range from about 20 degrees C. to about 40 degrees C. In another aspect, the testing of step (c) further comprises testing for enzyme activity at the temperatures of 25 degrees C. and 37 degrees C. In another aspect, the testing of step (c) further comprises testing for enzyme activity under normal osmotic pressure, and aberrant (positive or negative) osmotic pressure, In another aspect, the testing of step (c) further comprises testing for enzyme activity under normal electrolyte concentration, and aberrant (positive or negative) electrolyte concentration. The electrolyte concentration to be tested is selected from one of calcium, sodium, potassium, magnesium, chloride, bicarbonate and phosphate concentration, in another aspect, the testing of step (c) further comprises testing for enzyme activity which results in a stabilized reaction product.

In another aspect, the disclosure provides for a purified antibody that specifically binds to the polypeptide of the disclosure or a fragment thereof, having enzyme activity, In one aspect, the disclosure provides for a fragment of the antibody that specifically binds to a polypeptide having enzyme activity.

Antibodies and Antibody-Based Screening Methods

The disclosure provides isolated or recombinant antibodies that specifically bind to an enzyme of the disclosure. These antibodies can be used to isolate, identify or quantify the enzymes of the disclosure or related polypeptides. These antibodies can be used to isolate other polypeptides within the scope the disclosure or other related enzymes. The antibodies can be designed to bind to an active site of an enzyme. Thus, the disclosure provides methods of inhibiting enzymes using the antibodies of the disclosure.

The antibodies can be used in immunoprecipitation, staining, immunoaffinity columns, and the like. If desired, nucleic acid sequences encoding for specific antigens can be generated by immunization followed by isolation of polypeptide or nucleic acid, amplification or cloning and immobilization of polypeptide onto an array of the disclosure. Alternatively, the methods of the disclosure can be used to modify the structure of an antibody produced by a cell to be modified, e.g., an antibody's affinity can be increased or decreased. Furthermore, the ability to make or modify antibodies can be a phenotype engineered into a cell by the methods of the disclosure.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, N Y (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) "Continuous cultures of fused cells secreting antibody of predefined specificity", Nature 256: 495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals See, e.g., Hoogenboom (1997) "Designing and optimizing library selection strategies for generating high-affinity antibodies", *Trends Biotechnol.* 15:62-70; and Katz (1997) "Structural and mechanistic determinants of affinity and specificity of ligands discovered or engineered by phage display", *Annu. Rev. Biophys. Biomol. Struct.* 26:27-45.

Polypeptides or peptides can be used to generate antibodies which bind specifically to the polypeptides, e.g., the enzymes, of the disclosure. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the disclosure.

In immunoaffinity procedures, the antibody is attached to a solid support, such as a bead or other column matrix. The protein preparation is placed in contact with the antibody under conditions in which the antibody specifically binds to one of the polypeptides of the disclosure. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of the disclosure can be obtained by direct injection of the polypeptides into an animal or by administering the polypeptides to a non-human animal. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77-96).

Techniques described for the production of single chain antibodies (see, e.g., U.S. Pat. No. 4,946,778) can be adapted to produce single chain antibodies to the polypeptides of the disclosure. Alternatively, transgenic mice may be used to express humanized antibodies to these polypeptides or fragments thereof. Antibodies generated against the polypeptides of the disclosure may be used in screening for similar polypeptides (e.g., enzymes) from other organisms and samples. In such techniques, polypeptides from the organism are contacted with the antibody and those polypeptides which specifically bind the antibody are detected. Any of the procedures described above may be used to detect antibody binding.

Screening Methodologies and "On-Line" Monitoring Devices

In practicing the methods of the disclosure, a variety of apparatus and methodologies can be used to in conjunction with the polypeptides and nucleic acids of the disclosure, e.g., to screen polypeptides for enzyme activity, to screen compounds as potential modulators, e.g., activators or inhibitors, of an enzyme activity, for antibodies that bind to a polypeptide of the disclosure, for nucleic acids that hybridize to a nucleic acid of the disclosure, to screen for cells expressing a polypeptide of the disclosure and the like.

Arrays, or "Biochips"

Nucleic acids or polypeptides of the disclosure can be immobilized to or applied to an array. Arrays can be used to screen for or monitor libraries of compositions (e g, small molecules, antibodies, nucleic acids, etc.) for their ability to bind to or modulate the activity of a nucleic acid or a polypeptide of the disclosure. For example, in one aspect of the disclosure, a monitored parameter is transcript expression of an enzyme gene. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the disclosure. Polypeptide arrays" can also be used to simultaneously quantify a plurality of proteins. The present disclosure can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts.

In practicing the methods of the disclosure, any known array and/or method of making and using arrays can be incorporated in whole or in part, or variations thereof, as described, for example, in U.S. Pat. Nos. 6,277,628; 6,277, 489; 6,261,776; 6,258,606; 6,054,270; 6,048,695; 6,045, 996; 6,022,963; 6,013,440; 5,965,452; 5,959,098; 5,856, 174; 5,830,645; 5,770,456; 5,632,957; 5,556,752; 5,143, 854; 5,807,522; 5,800,992; 5,744,305; 5,700,637; 5,556, 752; 5,434,049; see also, e.g., WO 99/51773; WO 99/09217; WO 97/46313; WO 96/17958; see also, e.g., Johnston (1998) "Gene chips: Array of hope for understanding gene regulation", *Curr. Biol.* 8:R171-R174; Schummer (1997) "Inexpensive Handheld Device for the Construction of High-Density Nucleic Acid Arrays", *Biotechniques* 23:1087-1092; Kern (1997) "Direct hybridization of large-insert genomic clones on high-density gridded cDNA filter arrays", *Biotechniques* 23:120-124; Solinas-Toldo (1997) "Matrix-Based Comparative Genomic Hybridization:

Biochips to Screen for Genomic Imbalances", *Genes, Chromosomes & Cancer* 20:399-407; Bowtell (1999) "Options Available—From Start to Finish—for Obtaining Expression Data by Microarray", *Nature Genetics Supp.* 21:25-32. See also published U.S. patent applications Nos. 20010018642; 20010019827; 20010016322; 20010014449; 20010014448; 20010012537; 20010008765.

Capillary Arrays

Capillary arrays, such as the GIGAMATRIX™ Diversa Corporation, San Diego, Calif., can be used in the methods of the disclosure. Nucleic acids or polypeptides of the disclosure can be immobilized to or applied to an array, including capillary arrays. Arrays can be used to screen for or monitor libraries of compositions (e.g., small molecules, antibodies, nucleic acids, etc.) for their ability to bind to or modulate the activity of a nucleic acid or a polypeptide of the disclosure. Capillary arrays provide another system for holding and screening samples. For example, a sample screening apparatus can include a plurality of capillaries formed into an array of adjacent capillaries, wherein each capillary comprises at least one wall defining a lumen for retaining a sample. The apparatus can further include interstitial material disposed between adjacent capillaries in the array, and one or more reference indicia formed within of the interstitial material. A capillary for screening a sample, wherein the capillary is adapted for being bound in an array of capillaries, can include a first wall defining a lumen for retaining the sample, and a second wall formed of a filtering material, for filtering excitation energy provided to the lumen to excite the sample. A polypeptide or nucleic acid, e.g., a ligand, can be introduced into a first component into at least a portion of a capillary of a capillary array. Each capillary of the capillary array can comprise at least one wall defining a lumen for retaining the first component. An air bubble can be introduced into the capillary behind the first component. A second component can be introduced into the capillary, wherein the second component is separated from the first component by the air bubble. A sample of interest can be introduced as a first liquid labeled with a detectable particle into a capillary of a capillary array, wherein each capillary of the capillary array comprises at least one wall defining a lumen for retaining the first liquid and the detectable particle, and wherein the at least one wall is coated with a binding material for binding the detectable particle to the at least one wall. The method can further include removing the first liquid from the capillary tube, wherein the bound detectable particle is maintained within the capillary, and introducing a second liquid into the capillary tube. The capillary array can include a plurality of individual capillaries comprising at least one outer wall defining a lumen. The outer wall of the capillary can be one or more walls fused together. Similarly, the wall can define a lumen that is cylindrical, square, hexagonal or any other geometric shape so long as the walls form a lumen for retention of a liquid or sample. The capillaries of the capillary array can be held together in close proximity to form a planar structure. The capillaries can be bound together, by being fused (e.g., where the capillaries are made of glass), glued, bonded, or clamped side-by-side. The capillary array can be formed of any number of individual capillaries, for example, a range from 100 to 4,000,000 capillaries. A capillary array can form a micro titer plate having about 100,000 or more individual capillaries bound together.

In some embodiments, the activity of the conditionally active biologic protein of the invention is inhibited by a small molecule under a normal physiological condition but not or less inhibited by the same small molecule under an aberrant condition. For example, the activity of a conditionally active biologic protein may be inhibited by oxygen, glucose, or bicarbonate that is present at a certain concentration in human blood plasma but the activity of the same protein may be inhibited to a lesser extent or not at all in a tumor microenvironment since the concentration of the oxygen, glucose or bicarbonate may be lower in the tumor microenvironment than in the human blood plasma.

In some embodiments, the method of the invention can simultaneously improve the binding affinity and selectivity of a template polypeptide. For example, starting from a template antibody, the method can generate a conditionally active antibody that has both higher binding affinity to an antigen than the template antibody under the aberrant condition and higher ratio of the activity at the aberrant condition to the activity at the normal physiological condition than the template antibody. In one embodiment, these results are achieved by using Combinatorial Protein Synthesis (CPS) as described in U.S. Pat. No. 8,859,467. Specifically, CPS can be used to simultaneously incorporate mutations that improve both the conditional activity and the affinity to thereby simultaneously improve both affinity and selectivity of the selected conditionally active biologic proteins.

Assay Conditions

The normal physiological condition and the aberrant condition for the assays used in the screening step may be conducted using a condition selected from temperature, pH, osmotic pressure, osmolality, oxidative stress, electrolyte concentration, as well as combinations of two or more such conditions. For example, the normal physiological condition for temperature may be a normal human body temperature of 37.0° C., while the aberrant condition for temperature may be a temperature different from the temperature of 37.0° C., such as a temperature in tumor microenvironment which may be 1-2° C. higher than the normal physiological temperature. In another example, the normal physiological condition and the aberrant condition may also be a normal physiological pH in the range of 7.2-7.6 and an aberrant pH such as in the range of 6.2-6.8 presented in a tumor microenvironment.

The assays under both the normal physiological condition and the aberrant condition may be performed in an assay media. The assay media may be a solution, which may contain, for example, a buffer as well as other components. Common buffers that can be used in the assay media include citrate buffers such as sodium citrate, phosphate buffers, bicarbonate buffers such as the Krebs buffer, phosphate buffered saline (PBS) buffer, Hank's buffer, Tris buffer, HEPES buffer, etc. Other buffers known to a person skilled in the art to be suitable for the assays may be used. These buffers may be used to mimic a characteristic or component of the composition of a bodily fluid, of a human or animal such as blood plasma or lymphatic fluid.

The assay solutions useful in the methods of the invention may contain at least one component selected from inorganic compounds, ions and organic molecules, preferably ones that are commonly found in a bodily fluid of a mammal such as a human or animal. Examples of such components include nutritional components and metabolites, as well as any other components that may be found in a bodily fluid. The present invention contemplates that this component may or may not be part of the buffer system. For example, the assay solutions may be PBS buffer with added bicarbonate ion where bicarbonate is not part of PBS buffer. Alternatively, bicarbonate ion is part of the bicarbonate buffer.

The inorganic compounds or ions may be selected from one or more of boric acid, calcium chloride, calcium nitrate, di-ammonium phosphate, magnesium sulfate, mono-ammonium phosphate, mono-potassium phosphate, potassium chloride, potassium sulfate, copper sulfate, iron sulfate, manganese sulfate, zinc sulfate, magnesium sulfate, calcium nitrate, chelates of calcium, copper, iron, manganese and zinc, ammonium molybdate, ammonium sulphate, calcium carbonate, magnesium phosphate, potassium bicarbonate, potassium nitrate, hydrochloric acid, carbon dioxide, sulfuric acid, phosphoric acid, carbonic acid, uric acid, hydrogen chloride, urea, phosphorus ion, sulfuric ion, chloride ion, magnesium ion, sodium ion, potassium ion, ammonium ion, iron ion, zinc ion and copper ion.

Examples of normal physiological concentrations of some of the inorganic compounds include: uric acid in a concentration range of 2-7.0 mg/dL, calcium ion in a concentration range of 8.2-11.6 mg/dL, chloride ion in a concentration range of 355-381 mg/dL, iron ion in a concentration range of 0.028-0.210 mg/dL, potassium ion in a concentration range of 12.1-25.4 mg/dL, sodium ion in a concentration range of 300-330 mg/dL, carbonic acid in a concentration range of 15-30 mM, citrate ion at about 80 µM, histidine ion in the range of 0.05-2.6 mM, histamine in the range of 0.3-1 µM, HAPT ion (hydrogenated adenosine triphosphate) in the range of 1-20 µM, and HADP ion in the range of 1-20 µM.

In some embodiments, the ion present in the assay solutions for both the normal physiological condition and the aberrant condition is selected from hydroxide ion, halide ion (chloride, bromide, iodide), oxyhalide ion, sulfate ion, magnesium ion, calcium ion, bisulfate ion, carbonate ion, bicarbonate ion, sulfonate ion, oxyhalide ion, nitrate ion, nitrite ion, phosphate ion, hydrogen phosphate ion, dihydrogen phosphate ion, persulfate ion, monopersulfate ion, borate ion, ammonium ion, or organic ion, such as carboxylate ion, phenolate ion, sulfonate ion (organosulfate such as methyl sulfate), vanadate ion, tungstate ion, borate ion, organoboronate ion, citrate ion, oxalate ion, acetate ion, pentaborate ion, histidine ion, and phenolate ion.

The organic compounds present in the assay solutions for both the normal physiological condition and the aberrant condition may be selected from, for example, amino acids such as Histidine, Alanine, Isoleucine, Arginine, Leucine, Asparagine, Lysine, Aspartic acid, Methionine, Cysteine, Phenylalanine, Glutamic acid, Threonine, Glutamine, Tryptophan, Glycine, Valine, Pyrrolysine, Proline, Selenocysteine, Serine, Tyrosine and mixtures thereof.

Examples of a normal physiological concentration of some of the amino acids include: Alanine at 3.97±0.70 mg/dL, Arginine at 2.34±0.62 mg/dL, Glutamic acid at 3.41±1.39 mg/dL, Glutamine at 5.78±1.55 mg/dL, Glycine at 1.77±0.26 mg/dL, Histidine at 1.42±0.18 mg/dL, Isoleucine at 1.60±0.31 mg/dL, Leucine at 1.91±0.34 mg/dL, Lysine at 2.95±0.42 mg/dL, Methionine at 0.85±0.46 mg/dL, Phenylalanine at 1.38±0.32 mg/dL, Threonine at 2.02±6.45 mg/dL, Tryptophan at 1.08±0.21 mg/dL, Tyrosine at 1.48±0.37 mg/dL and Valine at 2.83±0.34 mg/dL.

The organic compounds present in the assay solutions for both the normal physiological condition and the aberrant condition may be selected from non-protein nitrogen-containing compounds such as creatine, creatinine, guanidino acetic acid, uric acid, allantoin, adenosine, urea, ammonia and choline. Examples of normal physiological concentrations of some of these compounds include: creatine at 1.07±0.76 mg/dL, creatinine at from 0.9 to 1.65 mg/dL, guanidino acetic acid at 0.26±0.24 mg/dL, uric acid at 4.0±2.9 mg/dL, allantoin at from 0.3 to 0.6 mg/dL, adenosine at 1.09±0.385 mg/dL, urea 27.1±4.5 mg/dL and choline at from 0.3 to 1.5 mg/dL.

The organic compounds present in the assay solutions for both the normal physiological condition and the aberrant condition may be selected from organic acids such as citric acid, α-ketoglutaric acid, succinic acid, malic acid, fumaric acid, acetoacetic acid, β-hydroxybutyric acid, lactic acid, pyruvic acid, α-ketonic acid, acetic acid, and volatile fatty acids. Examples of normal physiological concentrations of some of these organic acids include: citric acid at 2.5±1.9 mg/dL, α-ketoglutaric acid at 0.8 mg/dL, succinic acid at 0.5 mg/dL, malic acid at 0.46±0.24 mg/dL, acetoacetic acid at from 0.8 to 2.8 mg/dL, β-hydroxybutyric acid at 0.5±0.3 mg/dL, lactic acid at from 8 to 17 mg/dL, pyruvic acid at 1.0±0.77 mg/dL, α-ketonic acids at from 0.6 to 2.1 mg/dL, volatile fatty acids at 1.8 mg/dL.

The organic compounds present in the assay solutions for both the normal physiological condition and the aberrant condition may be selected from sugars (carbohydrates) such as glucose, pentose, hexose, xylose, ribose, mannose and galactose, as well as disaccharides including lactose, GlcNAcβ1-3Gal, Galα1-4Gal, Manα1-2Man, GalNAcβ1-3Gal and O-, N-, C-, or S-glycosides. Examples of normal physiological concentrations of some of these sugars include: glucose at 83±4 mg/dL, polysaccharides at 102±73 mg/dL (as hexose), glucosamine at 77±63 mg/dL, hexuronates at from 0.4 to 1.4 mg/dL (as glucuronic acid) and pentose at 2 0.55±0.37 mg/dL.

The organic compounds present in the assay solutions for both the normal physiological condition and the aberrant condition may be selected from fats or their derivatives such as cholesterol, lecithin, cephalin, sphingomyelin and bile acid. Examples of normal physiological concentrations of some of these compounds include: free cholesterol at from 40 to 70 mg/dL, lecithin at from 100 to 200 mg/dL, cephalin at from 0 to 30 mg/dL, sphingomyelin at from 10 to 30 mg/dL and bile acids at from 02. To 0.3 mg/dL (as cholic acid).

The organic compounds present in the assay solutions for both the normal physiological condition and the aberrant condition may be selected from proteins such as fibrinogen, antihaemophilic globulin, immune γ-globulin, immune euglobulins, isoagglutinins, β-pseudoglobulin, glycoproteins, lipoproteins and albumin. For example, the normal physiological concentration of mammal serum albumin is 3.5-5.0 g/dL. In one embodiment, the albumin is bovine serum albumin.

The organic compounds present in the assay solutions for both the normal physiological condition and the aberrant condition may be selected from vitamins such as Vitamin A, Carotene, Vitamin E, Ascorbic acid, Thiamine, Inositol, Folic acid, Biotin, Pantothenic acid, Riboflavin. Examples of normal physiological concentrations of some of these vitamins include: Vitamin A at from 0.019 to 0.036 mg/dL, Vitamin E at from 0.90 to 1.59 mg/dL, Inositol at from 0.42 to 0.76 mg/dL, Folic acid at from 0.00162 to 0.00195 mg/dL and biotin from 0.00095 to 0.00166 mg/dL.

The concentration of the inorganic compound, ion, or organic molecule in the assay solutions (for both assay under normal physiological condition and assay under an aberrant condition) may be within the normal range of physiological concentration of the inorganic compound, ion, or organic molecule in human or animal blood serum. However, the concentrations outside of the normal physiological range may also be used. For example, the normal range in human serum for magnesium ion is 1.7-2.2 mg/dL, and calcium is 8.5 to 10.2 mg/dL. The concentration for magnesium ion in the assay solutions may be from about 0.17 mg/dL to about 11 mg/dL. The concentration for calcium ion in the assay solutions may be from about 0.85 mg/dL to about 51 mg/dL. As a general rule, the concentration of the inorganic compound, ion, or organic molecule in the assay solutions may be as low as 5%, or 10%, or 20%, or 30%, or 40%, or 50%, or 60%, or 70%, or 80% of the normal physiological concentration of the inorganic compound, ion, or organic molecule in human serum, or as high as 1.5 times, or 2 times, or 3 times, or 4 times or 5 times, or 7 times or 9 times or 10 times or even 20 times the normal physiological concentration of the inorganic compound, ion, or organic molecule in human serum. Different components of the assay solutions may be used at different concentration levels relative to their respective normal physiological concentrations.

The assays under a normal physiological condition and an aberrant condition are used to measure the activity of the mutant proteins. During the assays both the mutant protein and its binding partner are present in the assay solutions. The relationship between the mutant protein and its binding partner may be, for example, antibody-antigen, ligand-receptor, enzyme-substrate, or hormone-receptor. In order for a mutant protein to manifest its activity, the mutant protein should be able to come into contact with and bind to its binding partner. The activity of the mutant protein on its binding partner is then manifested and measured after the binding between the mutant protein and its binding partner.

In some embodiments, the ions used in the assay may function in forming a bridge between the mutant protein being screened and its binding partner, particularly those including charged amino acid residues. The ion may thus be capable of binding to both the mutant protein and its binding partner through hydrogen bonds and/or ionic bonds. This may assist the binding between the mutant protein and its binding partner by allowing the ion to reach a site that may be hard to reach by a large molecule (mutant protein or its binding partner). In some cases, the ion in the assay solutions may increase the probability of the mutant protein and its binding partner binding to one another. Further, the ion may additionally or alternatively assist the binding between the mutant protein and its binding partner by binding to a larger molecule (mutant protein or its binding partner). This binding may alter the conformation of the large molecule and/or cause the larger molecule to remain in a particular conformation that facilitates binding with its binding partner.

It has been observed that the ions can assist the binding between the mutant protein and its binding partner, possibly by forming ionic bonds with the mutant protein and its binding partner. Thus, the screening may be much more efficient and more hits (candidate conditionally active biologic proteins) can be identified in comparison with the same assays without the ion. Suitable ions may be selected from magnesium ion, sulfate ion, bisulfate ion, carbonate ion, citrate ion, HAPT ion, HADP ion, bicarbonate ion, nitrate ion, nitrite ion, phosphate ion, hydrogen phosphate ion, dihydrogen phosphate ion, persulfate ion, monopersulfate ion, borate ion, lactate ion, citrate ion, histidine ion, histamine ion, and ammonium ion.

It has been found that the ions function to assist the binding between the mutant protein and its binding partner at a pH near a pKa of the ion. Such ions are preferably relatively small in relation to the size of the mutant proteins.

In one embodiment, when the aberrant condition is a pH that is different from the normal physiological pH under the normal physiological condition, the ions suitable for increasing the number of hits for candidate conditionally active biologic proteins may be selected from ions having a pKa that is close to the aberrant pH to be tested in the assay. For example, the pKa of the ion may be 1 pH unit away from the aberrant pH, 0.8 pH unit away from the aberrant pH, 0.6 pH unit away from the aberrant pH, 0.5 pH unit away from the aberrant pH, 0.4 pH unit away from the aberrant pH, 0.3 pH unit away from the aberrant pH, 0.2 pH unit away from the aberrant pH, or 0.1 pH unit away from the aberrant pH.

Exemplary pKa's of ions useful in the present invention, which pKa's may vary slightly at different temperatures, are as follows: ammonium ion having a pKa at about 9.24, dihydrogen phosphate having a pKa at about at 7.2, acetic acid having a pKa at about 4.76, histidine having a pKa at about 6.04, bicarbonate ion having a pKa at about 6.4, citrate having a pKa at 6.4, lactate ion having a pKa at about 3.86, histamine having a pKa at about 6.9, HATP having a pKa at 6.95 ($HATP^{3-} \Leftrightarrow ATP^{4-}+H^+$) and HADP having a pKa at 6.88 ($HADP^{3-} \Leftrightarrow ADP^{4-}+H^+$).

In one embodiment, the conditionally active biologic proteins are assayed and selected in the presence hydrogen sulfide. Hydrogen sulfide has a pKa of 7.05. In some embodiments, different concentrations of hydrogen sulfide may be used in the assays representing the normal and aberrant physiological conditions. Alternatively, the assay media for both the normal physiological condition and aberrant condition have approximately the same concentration of hydrogen sulfide and also some difference in the value of the particular condition, for example, the assay may be conducted at different pH's. The concentration of hydrogen sulfide to be used in the assay may be from 100 μm to about 100 mM. Preferably, the assay medium has a hydrogen sulfide concentration of from 1 to 10 mM, or from 1 to 5 mM, or from 1 to 3 mM. Assays conducted in the presence of hydrogen sulfide are known.

In certain embodiments, once the pH for the aberrant condition (i.e., aberrant pH) is known, the ion suitable for increasing the hits for candidate conditionally active biologic proteins may be selected from ions that have a pKa that is at or near the aberrant pH, for example, the candidate ions may gave a pKa about 1 pH unit away from the aberrant pH, 0.8 pH unit away from the aberrant pH, 0.6 pH unit away from the aberrant pH, 0.5 pH unit away from the aberrant pH, 0.4 pH unit away from the aberrant pH, 0.3 pH unit away from the aberrant pH, 0.2 pH unit away from the aberrant pH, or 0.1 pH unit away from the aberrant pH.

As stated above, the ion is most effective at assisting the binding between the mutant protein and its binding partner at a pH that is at or close to the pKa of the ion. For example, it has been found that in an assay solution with a pH 7.2-7.6, the bicarbonate ion (having pKa about 6.4) is not very effective in assisting the binding between the mutant protein and its binding partner. As the pH in the assay solution decreased to 6.7 and further to around 6.4, the bicarbonate ion became increasingly effective in assisting the binding between the mutant protein and its binding partner. As a result, more hits could be identified in the assay at pH 6.4 in comparison with assay at pH 7.2-7.6. Similarly, histidine is not very effective in assisting the binding between the mutant protein and its binding partner at pH 7.4. As the pH of the assay solution is decreased to 6.7 and further to around 6.0, histidine becomes increasingly effective in assisting the binding between the mutant protein and its binding partner also allowing more hits to be identified at pHs in a range of about 6.2-6.4, for example.

The present invention surprisingly found that, when the pHs of the assay solutions for the normal physiological condition (i.e., a normal physiological pH) and aberrant condition (i.e., an aberrant pH) are different, an ion with pKa in the range of from about the middle point of the normal physiological pH and the aberrant pH to about the aberrant pH can greatly assist the binding between the mutant protein being screened and its binding partner. As a result, the screening assay is much more efficient in founding more hits or candidate conditionally biologic proteins with high activity at the aberrant condition.

In some embodiments, the pKa may even be at least one pH unit away from the aberrant pH. When the aberrant pH is an acidic pH, the pKa of a suitable ion may be in the range of from (aberrant pH −1) to the middle point between the aberrant pH and the normal physiological pH. When the aberrant pH is a basic pH, the pKa of a suitable ion may be in the range of from (aberrant pH +1) to the middle point between the aberrant pH and the normal physiological pH. The ions may be selected from those described in this application. However, many more ions that have not been explicitly described in the application may also be used. It is understood that, once the aberrant pH and the normal physiological pH are selected for the screening assays, a person skilled in the art can use the guiding principles of the invention to select any ion with a suitable pKa for increasing the efficiency of screening in identifying more hits with high activity at the aberrant condition.

For example, when the aberrant pH is 8.4 and the normal physiological pH is 7.4 for an exemplary screening, any ion with a pKa in the range of about 7.9 (the middle point) to 9.4 (i.e., 8.4+1) may be used in the screening. Some ions with a pKa in this range include ions derived from tricine (pKa 8.05), hydrazine (pKa 8.1), bicine (pKa 8.26), N-(2-Hydroxyethyl)piperazine-N'-(4-butanesulfonic acid) (pKa 8.3), N-Tris[hydroxymethyl]methyl-3-aminopropanesulfonic acid (pKa 8.4), taurine (pKa 9.06). For another example, when the aberrant pH is 6 and the normal physiological pH is 7.4 for an exemplary screening, any ion with a pKa in the range of about 5 (i.e., 6−1) to 6.7 (the middle point) may be used in the screening. Some ions with a pKa in this range include ions derived from malate (pKa 5.13), pyridine (pKa 5.23), piperazine (pKa 5.33), cacodylate (pKa 6.27), succinate (pKa 5.64), 2-(N-morpholino)ethanesulfonic acid (pKa 6.10), citrate (pKa 6.4), histidine (pKa 6.04) and bis-tris (6.46). A person skilled in the art will be able to consult a vast number of chemical manuals and text books to identify the known chemical compounds that can be converted to ions with a pKa falling in the ranges, including both inorganic chemical compounds and organic chemical compounds. Among the chemical compounds with a suitable pKa, the ones with a smaller molecular weight may be preferred.

Consequently, the present invention unexpectedly found that production of conditionally active biologic proteins eventually identified not only depends on generating the right protein mutants from a wild-type protein, but also depend on using an ion with a suitable pKa in the assay solutions. The invention contemplates that in addition to generating a large library of mutant proteins (e.g., through CPE and CPS), efforts should also be made to find a suitable ion (with proper pKa) for use in the assay solutions, because the ion can facilitate efficiently selecting the mutants with high activity from the large library. It is further contemplated that, without the suitable ion, the screening is less efficient and the probability of finding the mutants with high activity is decreased. Consequently, it may require multiple rounds of screening to achieve the same number of mutants with high activity without the suitable ion.

The ion in the assay solutions may be formed in situ from a component of the assay solution or be directly included in the assay solution. For example, $CO_2$ from the air may dissolve in the assay solution to provide carbonate and bicarbonate ions. For another example, sodium dihydrogen phosphate may be added to the assay solution to provide dihydrogen phosphate ions.

The concentration of this component in the assay solutions (for both assay under normal physiological condition and assay under an aberrant condition) may be the same or substantially the same as the concentration of the same component that is typically found in a naturally-occurring bodily fluid of a mammal, such as a human. In other embodiments, the concentration of the component may be higher, especially when the component is an ion that can function to assist the binding between the mutant protein and its binding partner, because it has been observed that higher concentration of such ion can form ionic bonds with the mutant protein and its binding partner, practically facilitate the bindings and increase the probability of finding more hits or candidate conditionally active proteins.

In some embodiments, the concentration of the ion in the assay solution may positively correlate with the probability of finding more hits using the assay, particularly when concentrations in excess of normal physiological concentrations are employed. For example, human serum has a concentration of about 15-30 mM of bicarbonate ion. In one example, as the concentration of bicarbonate ion in the assay solution was increased from 3 mM to 10 mM, to 20 mM, to 30 mM, to 50 mM and to 100 mM, the number of hits in the assay also increased with each increase in bicarbonate concentration. In view of this, the assay solution may employ concentrations of bicarbonate ranging from about 3 mM to about 200 mM, or from about 5 mM to about 150 mM or from about 5 mM to about 100 mM, or from about 10 mM to about 100 mM or from about 20 mM to about 100 mM or from about 25 mM to about 100 mM or from about 30 mM to about 100 mM or from about 35 mM to about 100 mM or from about 40 mM to about 100 mM or from about 50 mM to about 100 mM.

In another embodiment, the concentration of citrate in the assay solution may be from about 30 μM to about 120 μM, or from about 40 μM to about 110 μM, or from about 50 μM to about 110 μM, or from about 60 μM to about 100 μM, or from about μM to about 90 μM, or about μM.

Conditionally active biologic proteins have been found to have a higher proportion of charged amino acid residues when compared to the wild-type protein from which they are derived. For example, there are three positively charged amino acid residues: lysine, arginine and histidine; and two negatively charged amino acid residues: aspartate and glutamate. These charged amino acids are over-represented in the selected conditionally active biologic proteins in comparison with the wild-type proteins from which the mutant proteins are evolved from and the conditionally active biologic proteins are selected from the mutant proteins. This may be related to the use of ion in the assay solutions because more charged amino acid residues can form more hydrogen bonds/ionic bonds with the ions.

In one embodiment, the normal physiological condition is a normal physiological pH in the range of 7.2-7.6 and the aberrant condition is an aberrant pH in the range of 6.2-6.8. The assay solution for the assay under the normal physiological condition has the normal physiological pH and 50 mM of bicarbonate ion. The assay solution for the assay under the aberrant condition has the aberrant pH and 50 mM of bicarbonate ion. Because the pKa of bicarbonate ion is at about 6.4, the bicarbonate ion can assist the binding between the mutant proteins and its binding partner at the aberrant pH of 6.2-6.8, such as pH 6.4, In yet another embodiment, the normal physiological condition is a normal physiological pH in the range of 7.2-7.6 and the aberrant condition is an aberrant pH in the range of 6.2-6.8. The assay solution for the assay under the normal physiological condition has the normal physiological pH and 80 µM of citrate ion. The assay solution for the assay under the aberrant condition has the aberrant pH and 80 µM of citrate ion. Because the citrate ion has a pKa of 6.4, the citrate ion can effectively assist the binding between the mutant proteins and the binding partner in the assay solution for aberrant condition with pH 6.2-6.8. Therefore more candidate conditionally active biologic proteins may be identified that have higher binding activity under condition of pH 6.4 and lower activity under condition of pH at 7.2-7.8. The other ions, including acetic acid, histidine, bicarbonate, HATP and HADP, function in a similar way to enable an assay solution containing the ion to effectively screening for mutant proteins with a higher binding activity at a pH around the pKa of the ion and a lower binding activity at a pH that is different from the pKa of the ion (e.g., normal physiological pH).

In yet another embodiment, the normal physiological condition is a normal physiological temperature at 37° C. and the aberrant condition is an aberrant temperature at 38-39° C. (temperature in some tumor microenvironments). The assay solution for the assay under the normal physiological condition has the normal physiological temperature and 70 mM of bicarbonate ion. The assay solution for the assay under the aberrant condition has the aberrant temperature and 70 mM of bicarbonate ion.

In yet another embodiment, the normal physiological condition is a particular concentration of an electrolyte in normal human serum and the aberrant condition is the concentration of the same electrolyte in a different, aberrant concentration which may be located at a different location in the animal or human or may result from a condition of the animal or human that alters the normal physiological concentration of an electrolyte in human serum.

The binding between a mutant protein and/or its binding partner can also be influenced in a number of other ways. Typically, this influence will be exerted by inclusion of one or more additional components in the assay media. These additional components may be designed to interact with either the mutant protein, the binding partner or both. In addition, these additional components may use combinations of two or more interactions as well as combinations of two or more types of interactions to influence the binding.

In one embodiment, the binding interaction of interest is between and antibody and an antigen. In this embodiment, one or more additional components may be included in the assay media to exert influence on the antibody, antigen or both. In this manner, the desired binding interaction may be enhanced.

On addition to the ions that can form ionic bonds with a mutant protein and/or its binding partner to assist the binding between the mutant protein and the binding partner, the present invention also includes other components that may be employed assist binding between a mutant protein and its binding partner. In one embodiment, molecules that can form hydrogen bonds with a mutant protein and/or its binding partner are employed. In another embodiment, molecules that are capable of hydrophobic interaction with a mutant protein and/or its binding partner may be used. In yet another embodiment, molecules that are capable of Van der Waals' interactions with a mutant protein and/or its binding partner are contemplated.

As used herein, the term "hydrogen bond" refers to a relatively weak, noncovalent interaction between a hydrogen covalently bonded to an electronegative atom, such as carbon, nitrogen, oxygen, sulfur, chlorine, or fluorine (hydrogen bond donor), with an unshared electron pair of an electron donor atom, such as nitrogen, oxygen, sulfur, chlorine, or fluorine (hydrogen bond acceptor).

Components capable of forming a hydrogen bond with a mutant protein and/or its binding partner include organic molecules as well as inorganic molecules with a polar bond. Mutant proteins and/or binding partners for mutant proteins typically contain amino acids that can form hydrogen bonds. Suitable amino acids have a side chain with a polar group that is capable of forming a hydrogen bond. Non-limiting examples of suitable amino acids include glutamine (Gln), glutamic acid (Glu), arginine (Arg) asparagines (Asn), aspartic acid (Asp), lysine (Lys), histidine (His), serine (Ser), threonine (Thr), tyrosine (Tyr), cysteine (Cys), methionine (Met), and tryptophan (Trp).

These amino acids can function as both hydrogen donors and hydrogen acceptors. For example, the oxygen atom in an —OH group such as may be found in Ser, Thr, and Tyr, the oxygen atom in a —C=O group such as may be found in Glu and Asp, the sulfur atom in an —SH group or —SC— such as may be found in Cys and Met, the nitrogen atom in a —$NH_3^+$ group such as may be found in Lys and Arg, and the nitrogen atom in an —NH— group such as may be found in Trp, His and Arg, may all function as a hydrogen acceptor. Also, groups in this list including a hydrogen atom (e.g. —OH, —SH, $NH_3^+$ and —NH—) may function as a hydrogen donor.

In some embodiments, the backbone of the mutant protein and/or its binding partner may also participate in forming one or more hydrogen bonds. For example, the backbone may have a repeating structure of —(C=O)—NH— such as in peptide bonds. The oxygen and nitrogen atoms in this structure may function as hydrogen acceptors, while the hydrogen atom may participate in the hydrogen bond.

The inorganic compounds that have at least one polar bond involving a hydrogen or oxygen atom that may be used for hydrogen bonding may include, for example, $H_2O$, $NH_3$, $H_2O_2$, hydrazine, carbonates, sulfates and phosphates. Organic compounds such as alcohols; phenols; thiols; aliphatic, amines, amides; epoxides, carboxylic acids; ketones, aldehydes, ethers, esters, organochlorides, and organofluorides. Compounds that can form hydrogen bonds are well known in in the chemical literature, such as those discussed in, for example, "The Nature of the Chemical Bond," by Linus Pauling, Cornell University Press, 1940, pages 284 to 334, the disclosure of which is hereby incorporated by reference in its entirety for its listing of compounds capable of hydrogen bonding interactions.

In some embodiments, the alcohols may include methanol, ethanol, propanol, isopropanol, butanol, pentanol, 1-hexanol, 2-octanol, 1-decanol, cyclohexanol, and the higher alcohols; diols such as ethylene glycol, propylene glycol, glycerol, diethylene glycol, and polyalkylene glycols. Suitable phenols include hydroquinone, resorcinol, catechol, phenol, o-, m-, and p-cresol, thymol, alpha and beta-naphthol, pyrogallol, guaiacol, and phloroglucinol. Suitable thiols include methanethiol, ethanethiol, 1-propanethiol, 2-propanethiol, butanethiol, tert-butyl mercaptan, pentanethiols, hexanethiol, thiophenol, dimercaptosuccinic acid, 2-mercaptoethanol, and 2-mercaptoindole. Suitable amines include methylamine, ethylamine, propylamine, isopropylamine, aniline, dimethylamine and methylethylamine, trimethylamine, aziridine, piperidine, N-methylpiperidine, benzidine, cyclohexyl amine, ethylene diamine, hexamethylene diamine, o-, m-, and p-toluidine and N-phenylpiperidine. Suitable amides include ethanamide, N,N-dimethylacetamide, N,N-dimethyl formamide, N,N-dimethyl methoxy acetamide and N-methyl-N-p-cyanoethyl formamide. The epoxides may include ethylene oxide, propylene oxide, tert-butyl hydroperoxide, styrene oxide, epoxide glycidol, cyclohexene oxide, di-tert-butyl peroxide, cumene hydroperoxide or ethylbenzene hydroperoxide, isobutylene oxide, and 1,2-epoxyoctane. The carboxylic acids may include terephthalic acid, isophthalic acid, phthalic acid, salicylic acid, benzoic acid, acetic acid, lauric acid, adipic acid, lactic acid, citric acid, acrylic acid, glycine, hexa-hydrobenzoic acid, o-, m-, and p-toluic acids, nicotinic acid, isonicotinic acid, and para-aminobenzoic acid. The ketones may include acetone, 3-propanone, butanone, pentanone, methylethyl ketone, diisobutyl ketone, ethyl butyl ketone, methyl isobutyl ketone, methyl tert-butyl ketone, cyclohexanone, acetone, methyl ethyl ketone, methyl propyl ketone, methyl butyl ketone, methyl amyl ketone, methyl hexyl ketone, diethyl ketone, ethyl butyl ketone, dipropyl ketone, diisobutyl ketone, diacetone alcohol, phorone, isophorone, cyclohexanone, methyl cyclohexanone, and acetophenone. The aldehydes may include formaldehyde, acetaldehyde, propionaldehyde, butyraldehyde, benzaldehyde, cinnamaldehyde, sobutyraldehyde, valeraldehyde, octaldehyde, benzaldehyde, cinnamaldehyde, cyclohexanone, salicylaldehyde, and furfural. The esters include ethyl acetate, methyl acetate, ethyl formate, butyl acetate, ethyl lactate, ethyl butyrate, propyl acetate, ethyl formate, propyl formate, butyl formate, amyl formate, methyl acetate, ethyl acetate, propyl acetate, butyl acetate, amyl acetate, methyl isoamyl acetate, methoxybutyl acetate, hexyl acetate, cyclohexyl acetate, benzyl acetate, methyl propionate, ethyl propionate, butyl propionate, amyl propionate, methyl butyrate, ethyl butyrate, butyl butyrate, amyl butyrate, methyl acetoacetate, and ethyl acetoacetate. Ethers that may be used in the present invention include dimethyl ether, methyl ethyl ether, diethyl ether, methyl propyl ether, and dimethoxyethane. The ethers may be cyclic, such as ethylene oxide, tetrahydrofuran, and dioxane.

The organochlorides include chloroform, pentachloroethane, dichloromethane, trichloromethane, carbon tetrachloride, tetrachloromethane, tetrachloroethane, pentachloroethane, trichloroethylene, tetrachloroethylene, and ethylene dichloride. The organofluorides may include fluoromethane, difluoromethane, trifluoromethane, trifluoroethane tetrafluoroethane, pentafluoroethane, difluoropropane, trifluoropropane, tetrafluoropropane, pentafluoropropane, hexafluoropropane, and heptafluoropropane, Hydrogen bonds may be divided by the strength of the bond: strong, moderate, or weak hydrogen bonds (Jeffrey, George A.; An introduction to hydrogen bonding, Oxford University Press, 1997). The strong hydrogen bonds have donor-acceptor distances of 2.2-2.5 Å and energies in the range of 14-40 kcal/mol. The moderate hydrogen bonds have donor-acceptor distances of 2.5-3.2 Å and energies in the range of 4-15 kcal/mol. The weak hydrogen bonds have donor-acceptor distances of 3.2-4.0 Å and energies in the range of <4 kcal/mol. Some examples of hydrogen bonds with energy levels are F—H . . . :F (38.6 kcal/mol), O—H . . . :N (6.9 kcal/mol), O—H . . . :O (5.0 kcal/mol), N—H . . . :N (3.1 kcal/mol) and N—H . . . :O (1.9 kcal/mol). See more in Perrin et al. "Strong" hydrogen bonds in chemistry and biology, *Annual Review of Physical Chemistry*, vol. 48, pages 511-544, 1997; Guthrie, "Short strong hydrogen bonds: can they explain enzymic catalysis?" *Chemistry & Biology* March 1996, 3:163-170.

In some embodiments, the components used in the present invention can form a strong hydrogen bond with the mutant protein and/or its binding partner. These components tend to have an atom with a strong electronegativity. The atoms known to have the strongest electronegativity are F>O>Cl>N, in this order. Thus, the present invention preferably uses an organic compound that includes fluorine, a hydroxyl group or a carbonyl group, in forming the hydrogen bond. In one embodiment, organofluorines may be used in the present invention for forming a strong hydrogen bond.

In another embodiment, components capable of a hydrophobic interaction with a mutant protein and/or its binding partner are employed. Such components include organic compounds with a hydrophobic group.

As used herein, the term "hydrophobic interaction" refers to reversible attractive interactions between a hydrophobic compound or a hydrophobic region of a compound and another hydrophobic compound or hydrophobic region of the other compound. This type of interaction has been described in "Hydrophobic Interactions," A. Ben-Nairn (1980), Plenum Press, New York, the disclosure of which is hereby incorporated by reference for its description of hydrophobic interactions.

Hydrophobic materials are repelled by water molecules because of their non-polar nature. When relatively nonpolar molecule or groups in aqueous solution associate with other nonpolar molecules rather than with water, it is termed a "hydrophobic interaction."

The mutant proteins and their binding partners typically include amino acids that are capable of hydrophobic interactions. These amino acids will typically be characterized by having at least one side chain with a nonpolar group that is capable of a hydrophobic interaction. Hydrophobic amino acids include, for example, alanine (Ala), isoleucine (Ile), leucine (Leu), phenylalanine (Phe), valine (Val), proline (Pro), glycine (Gly), to a lesser extent, methionine (Met), and tryptophan (Trp).

Components that are capable of hydrophobic interactions with a mutant protein and/or its binding partner include organic compounds that are hydrophobic molecules or molecules containing at least one hydrophobic moiety. In some embodiments, these hydrophobic components may be hydrocarbons selected from aromatic hydrocarbons, substituted aromatic hydrocarbons, polyaromatic hydrocarbons, aromatic or non-aromatic heterocycles, cycloalkanes alkanes, alkenes, and alkynes. Hydrophobic groups may include aromatic groups, alkyl, cycloalkyl, alkenyl and alkynyl groups. The terms, "alkyl," "alkenyl" and "alkynyl" as used herein refer to unsaturated aliphatic groups having one to thirty carbon atoms, including straight-chain alkenyl/alkynyl groups, branched-chain alkenyl/alkynyl groups, cycloalkenyl (alicyclic) groups, alkyl substituted cycloalkyl groups, and cycloalkyl substituted alkenyl/alkynyl groups. Such hydrocarbon moieties may also be substituted on one or more carbon atoms.

It may be understood that the strength of the hydrophobic interaction is based upon the available amount of "hydrophobes" that may interact one another. Thus, the hydrophobic interaction may be adjusted by, for example, increasing the amount of and/or "hydrophobic" nature of the hydrophobic moiety in the molecules involved in the hydrophonbic interaction. For instance, a hydrophobic moiety, which in its original form may include a hydrocarbon chain, may be modified to increase its hydrophobicity (ability to increase the strength of hydrophobic interaction involved by the moiety) by having a hydrophobic side chain attach to one of the carbons of its carbon backbone. In a preferred embodiment of the invention, this may include the attachment of various polycyclic compounds, including for instance various steroidal compounds and/or their derivatives such as sterol type compounds, more particularly cholesterol. In general, the side chains may be linear chains, aromatic, aliphatic, cyclic, polycyclic, or any various other types of hydrophobic side chains as contemplated by those skilled in the art.

The type of components that are capable of van der Waals interactions with a mutant protein and/or its binding partner are usually, but not always compounds with a polar moiety. As used herein, "van der Waals interactions" refer to attractions between atoms, moieties, molecules, and surfaces that are caused by dipole-dipole interactions and/or correlations in the fluctuating polarizations of nearby atoms, moieties, or molecules as a consequence of quantum dynamics.

The van der Waals interactions in the present invention are attractive forces between the mutant proteins or the binding partner and the component. The van der Waals interactions may arise from three sources. First, some molecules/moieties, although electrically neutral, may be permanent electric dipoles. Because of fixed distortion in the distribution of electron charge in the structure of some molecules/moieties, one side of a molecule/moiety is always somewhat positive and the opposite side somewhat negative. The tendency of such permanent dipoles to align with each other results in a net attractive force. This is interaction between two permanent dipoles (Keesom force).

Second, the presence of molecules that are permanent dipoles may temporarily distort the electron charge in other nearby polar or nonpolar molecules, thereby inducing further polarization. An additional attractive force results from the interaction of a permanent dipole with the neighboring induced dipole. This is an interaction between a permanent dipole and a corresponding induced dipole may be referred to as a Debye force. Third, even though no molecules involved are permanent dipoles (e.g., the organic liquid benzene), a force of attraction exists between molecules with two instantaneously induced dipoles in the molecules. This is interaction between two instantaneously induced dipoles may be referred to as a London dispersion force.

There are many amino acids in a mutant protein and/or the binding partner that are capable of van der Waals interactions. These amino acids may have polar side chains, including glutamine (Gln), asparagine (Asn), histidine (His), serine (Ser), threonine (Thr), tyrosine (Tyr), cysteine (Cys), methionine (Met), tryptophan (Trp). These amino acids may also have a side chain with a non-polar group, including alanine (Ala), isoleucine (Ile), leucine (Leu), phenylalanine (Phe), valine (Val), proline (Pro), glycine (Gly), The components that are capable of van der Waals interactions with a mutant protein and/or its binding partner include polar or non-polar inorganic compounds that are soluble in the assay solution. The assay solution is generally an aqueous solution and thus these polar or non-polar inorganic compounds are preferably soluble in water. Preferred materials for van der Waals interactions are those that are polar such that they are capable of dipole-dipole interactions. For example $AlF_3$ has polar Al—F bonds and is soluble in water (about 0.67 g/100 ml water at 20° C.). $HgCl_2$ has polar Hg—Cl bonds and is soluble in water at 7.4 g/100 ml at 20° C. $PrCl_2$ has polar Pr—Cl bonds and is soluble in water at about 1 g/100 ml at 20° C.

Suitable polar compounds that are capable of van der Waals interactions include alcohols, thiols, ketones, amines, amides, esters, ethers, and aldehydes. Suitable examples of these compounds have been described above in relation to hydrogen bonding. Suitable non-polar compounds that are capable of van der Waals interactions include aromatic hydrocarbons, substituted aromatic hydrocarbons, polyaromatic hydrocarbons, aromatic or non-aromatic heterocycles, cycloalkanes, alkanes, alkenes, alkynes.

The hydrogen bonding components, hydrophobic components and Van der Waals components can be employed to influence binding of a mutant protein and its binding partner in a number of ways. In one embodiment the hydrogen bonding, hydrophobic interaction and/or Van der Waals interaction may form a bridge between the mutant protein and its binding partner. Such a bridge may bring the mutant protein and binding partner into closer proximity to one another to facilitate binding and/or position the mutant protein and/or binding partner relative to one another in a way that facilitates binding.

In another embodiment, the hydrogen bonding and/or hydrophobic interaction may increase the probability of the mutant protein binding to its binding partner by, for example, by causing the proteins and binding partners to group or associate with one another in a manner which increases the binding probability. Thus, one or more of these interactions may be used alone or in combination to group the mutant proteins and binding partners closer together or to arrange the mutant proteins and binding partners in a manner that facilitates binding by, for example, causing the binding sites to be drawn closer together or causing the non-binding portions of the molecules to arrange further away from one another thereby allowing the binding sites to locate closer to one another.

In still another embodiment, the hydrogen bonding and/or hydrophobic interaction may influence the conformation of a mutant protein and/or its binding partner to provide a conformation that is more conducive to the binding of the mutant protein with its binding partner. Specifically, binding to or interacting with one or more of the amino acids of the mutant protein and/or binding partner may cause one or more conformational shifts in the mutant protein or binding partner that favors the mutant protein/binding partner binding reaction.

The present invention conducts two pairs of assays, one to seek a decrease in activity for a mutant protein in the assay at the normal physiological condition when compared to the protein from which the mutant protein was derived at said normal physiological condition, and a second assay to seek an increase in activity of the mutant protein in the assay under the aberrant condition when compared to the protein from which the mutant protein was derived at said aberrant condition. In some cases, the protein from which the mutant protein was derived will be a wild-type protein. In other cases, the protein from which the mutant protein was derived may itself be a mutant protein that has been prepared using one or more of the mutation techniques described elsewhere herein.

The condition used in the pairs of assays of the present invention may be selected from temperature, pH, osmotic pressure, osmolality, oxidative stress, electrolyte concentration and the concentration of any other component of the assay solution or media. Thus, a particular component of the assay media may be used at substantially the same concentration in both pairs of assays. In such case, the component is typically present for the purpose of simulating a particular environment in a human or animal such as serum, a tumor microenvironment, a muscle environment, a neural environment or any other environment which may be encountered at the point of administration, may be traversed by the administered treatment or may be encountered at the point of treatment. One important aspect of selecting one or more components that simulate these environments is that it may improve the results of the selection process carried out using the pairs of assays. For example, simulating a particular environment allows various effects of particular components of that environment on the mutant proteins to be evaluated in the selection process. Components of a particular environment may, for example, alter or bind with the mutant protein, inhibit the activity of the mutant protein, inactivate the mutant protein, etc.

In some embodiments, one or more components of the assay solutions are preferably small molecules, such as hydrogen sulfide, bicarbonate, histamine, lactic acid, and acetic acid. In one embodiment, the small molecule component is preferably present in the assay solution at a concentration of from about 100 μm to about 100 mM, or, more preferably from about 0.5 to about 50 mM, or from about 1 to about 10 mM.

The concentration of the component in the assay solutions may be the same or substantially the same as the concentration of the same component that is typically found in a naturally-occurring bodily fluid of a mammal, such as a human. This may be referred to as a normal physiological concentration of the component in the bodily fluid. In other embodiments, the concentration of a particular component in the assay solutions may be less than, or greater than the concentration of the same component that is typically found in a naturally-occurring bodily fluid of a mammal, such as a human.

In another embodiment, a component may be present at substantially different concentrations in each of the pairs of assays. In such case, the presence, absence or concentration of the component becomes the condition that is being assayed since it is the concentration of the component that is the condition that differentiates between the assay solutions for the assay under a normal physiological condition and the assay solution for the assay under an aberrant condition. Thus, the conditionally active biologic protein produced by this embodiment of the method of the present invention would be selected for an activity at least partially dependent on the concentration of the component.

In some embodiments, the component may be present in one pair of assay solutions but entirely absent from the other pair of assay solutions. For example, the concentration of lactic acid in the assay solution for the aberrant condition may be set to a level simulating a lactic acid concentration in the tumor microenvironment. Lactic acid may be absent from the pair of assay solutions for the normal physiological condition.

In one embodiment, the normal physiological condition is a first lactic acid concentration representative of a normal physiological condition and the aberrant condition is a second lactic acid concentration representative of an aberrant condition that exists in a particular location in the body.

In another example, glucose may be absent in the assay solution for the aberrant condition to simulate the absence of glucose that may be found in a tumor microenvironment, while glucose may be set to a level that simulates a blood plasma glucose concentration in the pair of assay solutions for the normal physiological condition. This feature may be used for preferential delivery of the conditionally active biologic protein to the location or environment without no or minimal activity in transit, and activation of the conditionally active biologic protein when it arrives at the environment where the concentration of the component in the assay solution for the aberrant condition is present.

For example, a tumor microenvironment typically has both a lower glucose concentration and a higher lactic acid concentration in comparison with human serum. The normal physiological concentration of glucose is in the range of about 2.5 mM to about 10 mM in serum. On the other hand, the glucose concentration is typically very low in the range of 0.05 mM to 0.5 mM in the tumor microenvironment. In one embodiment, the assay solution for the assay under the normal physiological condition has a glucose concentration in the range of about 2.5 mM to about 10 mM and the assay solution for the assay under the aberrant condition has a glucose concentration in the range of about 0.05 mM to about 0.5 mM. The conditionally active biologic protein thus produced has a higher activity in a low glucose environment than in a higher glucose environment. This conditionally active biologic protein will be functional in the tumor microenvironment but have a low activity in transit in the blood stream.

The normal physiological concentration of lactic acid in serum is in the range of about 1 mM to about 2 mM. On the other hand, lactic acid concentration is typically in the range of 10 mM to 20 mM in the tumor microenvironment. In one embodiment, the assay solution for the assay under the normal physiological condition has a lactic acid concentration in the range of about 1 mM to about 2 mM and the assay solution for the assay under the aberrant condition has a lactic acid concentration in the range of about 10 mM to about 20 mM. The conditionally active biologic protein thus produced has higher activity in a high lactic acid environment than in a lower lactic acid environment. This conditionally active biologic protein will thus be functional in the tumor microenvironment but have a low activity in transit in the blood stream.

Similarly, it is known that sore muscles have a higher (aberrant) concentration of lactic acid than normal. Thus, when seeking a mutant protein that will be active in a sore muscle environment, the pair of assays at the aberrant condition can be conducted in the presence of a higher concentration of lactic acid to simulate the sore muscle environment, while the pair of assays at the normal physiological condition can be conducted with a lower concentration of, or in the absence of, lactic acid. In this manner, the mutant protein can be selected for enhanced activity in a sore muscle environment with an increased lactic acid concentration. Such a conditionally active biologic protein may be useful as an anti-inflammatory agent, for example.

In another embodiment, two or more components may be used in both pairs of the assay solutions. In this type of assay, the conditionally active biologic protein may be selected using characteristics of both of the two types of assays described above. Alternatively, the selectivity of the conditionally active biologic protein can be increased using two or more components. For example, returning to the tumor microenvironment, the pair of assays at the aberrant condition can be conducted in assay media with both a high lactic acid concentration and a low glucose concentration while the corresponding pair of assays at the normal physiological condition can be conducted in an assay media with both a relatively lower lactic acid concentration and a relatively higher glucose concentration.

The present invention contemplates that each component selected from the inorganic compounds, ions, and organic molecules may be used alone or in combination to select a conditionally active biologic protein that is more active at one concentration of the component than at a different concentration of the same component.

Assays relying on different concentrations of one or more metabolites as the differentiating condition(s) between the normal environment and the aberrant environment may be particularly suitable for selecting a conditionally active biologic protein that is more active in the tumor microenvironment than in blood plasma, because the tumor microenvironment typically has a significant number of metabolites that have different concentrations in comparison with the concentrations of the same metabolites in blood plasma.

Kinoshita et al., "Absolute Concentrations of Metabolites in Human Brain Tumors Using In Vitro Proton Magnetic Resonance Spectroscopy," NMR IN BIOMEDICINE, vol. 10, pp. 2-12, 1997, compared the metabolites in a normal brain and brain tumors. This group discovered that N-acetyl aspartate has a concentration of 5000-6000 μM in normal brain but the concentration is only 300-400 μM in glioblastoma, 1500-2000 μM in astrocytoma, and 600-1500 μM in anaplastic astrocytoma. Further, inositol has a concentration of 1500-2000 μM in a normal brain but the concentration is 2500-4000 μM in glioblastoma, 2700-4500 μM in astrocytoma, and 3800-5800 μM in anaplastic astrocytoma. Phosphorylethanolamine has a concentration of 900-1200 μM in a normal brain but the concentration is 2000-2800 μM in glioblastoma, 1170-1370 μM in astrocytoma, and 1500-2500 μM in anaplastic astrocytoma. Glycine has a concentration of 600-1100 μM in a normal brain but the concentration is 4500-5500 μM in glioblastoma, 750-1100 μM in astrocytoma, and 1900-3500 μM in anaplastic astrocytoma. Alanine has a concentration of 700-1150 μM in a normal brain but the concentration is 2900-3600 μM in glioblastoma, 800-1200 μM in astrocytoma, and 300-700 μM in anaplastic astrocytoma. These metabolites may also have different concentration in blood, for example, N-acetyl aspartate has a concentration of about 85000 μM in blood; inositol has a concentration of about 21700 μM in blood; glycine has a concentration of about 220-400 μM in blood; alanine has a concentration of about 220-300 μM in blood.

Therefore, these metabolites, including at least N-acetyl aspartate, inositol, glycine and alanine, may be used at different concentrations in the assay solutions to select conditionally active biologic proteins that are active in brain tumors but not active in blood or normal brain tissue. For example, an assay solution with a concentration of 85000 μM of N-acetyl aspartate may be used for the pair of assays under a normal physiological condition and an assay solution with a concentration of 350 μM of N-acetyl aspartate may be used for the pair of assays under an aberrant condition to select conditionally active biologic proteins that are active in the tumor microenvironment of glioblastoma, but not active or at least less active in blood or normal brain tissue.

Mayers et al., "Elevated circulating branched chain amino acids are an early event in pancreatic adenocarcinoma development," Nature Medicine, vol. 20, pp. 1193-1198, 2014, studied the concentrations of a variety of different metabolites including branched chain amino acids in prediagnostic blood plasma of pancreatic patients. It was found that in pancreatic tumor patients, there are several metabolites that are present in the bloodstream at different concentrations relative to the concentrations of the same metabolites in the blood of a human without pancreatic cancer. Mayers et al. also found that pancreatic cancer patients have significantly elevated branched amino acids in their blood plasma, in comparison with normal subjects. The branched amino acids that are present at elevated concentrations include isoleucine, leucine and valine (Table 1 of Mayers). There are other metabolites shown in FIG. 1 of Mayers that are present at significantly different concentrations in the blood plasma of pancreatic cancer patients than in normal healthy humans. These metabolites include at least acetylglycine, glycine, phenylalanine, tyrosine, 2-aminoadipate, taurodeoxycholate/taurochenodeoxycholate, aconitate, isocitrate, lactate, a-glycerophosphate and urate. Thus, based on the findings that certain metabolites are present at different concentrations in the blood plasma of pancreatic cancer patients and normal healthy patients, it can be predicted that the tumor microenvironment of pancreatic cancer will also have different concentrations for these metabolites than would be present in the pancreatic microenvironment of a healthy patient.

Thus, in one embodiment, one or more of these metabolites may be used in the assay solution for the normal physiological condition in amounts that approximate the concentrations of these metabolites in the blood plasma in a healthy individual (i.e., normal physiological concentrations of the metabolites). For example, the known normal physiological concentrations in blood plasma of a healthy individual are about 1.60±0.31 mg/dL for isoleucine, about 1.91±0.34 mg/dL for leucine, and about 2.83±0.34 mg/dL for valine. The assay solution for the normal physiological condition may have normal physiological concentrations within these ranges of one or more of these branched amino acids. The assay solution for the aberrant condition may have the same branched amino acids at concentrations that are about 5 fold, or about 10 fold, or about 20 fold, or about 50 fold, or about 70 fold, or about 100 fold, or about 150 fold, or about 200 fold, or about 500 fold higher than the normal physiological concentrations in a healthy individual of the corresponding branched amino acids. This would reflect the fact that the pancreatic tumor microenvironment would be expected to have significantly elevated concentrations of these branched amino acids based on the findings of Mayers et. al. since the higher concentrations of these branched amino acids found in the blood plasma detected by Mayers et al. originate from the tumor microenvironment and are diluted in the blood stream. Similarly, the assay under the aberrant condition may reflect the concentrations of other metabolites in the blood of a pancreatic cancer patient even if the concentrations of particular metabolites are significantly lower in the cancer patient than in the normal individual. In this manner, the screening can simulate the actual environment and thereby ensure the highest activity mutants for that particular environment are selected.

In some other embodiments, the assay solution for the normal physiological condition may comprise one or more branched amino acids at concentrations simulating concentrations in the blood plasma of pancreatic cancer patients to simulate the actual blood plasma environment for these patients. In such embodiments, the assay solution for the aberrant condition may have the same branched amino acids at concentrations that are about 2 fold, or about 3 fold, or about 4 fold, or about 5 fold, or about 7 fold, or about 8 fold, or about 10 fold, or about 15 fold, or about 20 fold, or about 50 fold higher than the concentrations of the corresponding branched amino acids in the blood plasma of pancreatic cancer patients to reflect the fact that these higher concentrations are originating in the tumor microenvironment and the concentrations in the blood stream represent a dilution of the actual concentrations of the tumor microenvironment. Similarly, other metabolites may also have different concentrations in the assay solutions for the normal physiological condition and aberrant condition to reflect actual differences expected from the data collected for the blood stream. In some instances, a deficiency of a particular metabolite may be noted in the blood stream of a pancreatic patient in which case a concentration reflecting the measured concentration in the blood stream can be used in the assay for the normal physiological condition, and an even lower concentration can be used in the assay for the aberrant condition to account for the expectation that said metabolite is likely being consumed in the tumor microenvironment. The conditionally active biologic proteins thus selected using the assay solutions will be more active in the pancreatic cancer microenvironment than in the blood plasma of pancreatic cancer patients.

In some embodiments, the entire blood plasma of pancreatic cancer patients may be used in the present invention. For example, in one embodiment, a simulation of one or more components of the blood plasma of pancreatic cancer patient may be used in the assay solutions for one or both of assays under the normal physiological condition and the aberrant condition. In an exemplary embodiment, the assay solution for the normal physiological condition has a pH in the range of 7.2-7.6 and with 30 wt. % of blood plasma of a pancreatic cancer patient added and the assay solution for the aberrant condition has a pH in the range of 6.4-6.8 and with 30 wt. % of blood plasma of pancreatic cancer patient added. In this embodiment, the blood plasma of the pancreatic cancer patient is present to both (1) ensure that the conditionally active biologic protein is not activated in the blood at pH 7.2-7.6, and (2) also ensure that the conditionally active biologic protein can be activated by the pH 6.2-6.8 in the tumor microenvironment even in the presence of this composition of metabolites that is found in the blood of the pancreatic cancer patient. This will tailor the treatment for a pancreatic cancer patient.

In another exemplary embodiment, the assay solution for the normal physiological condition has a pH in the range of 7.2-7.6 and with 30 wt. % of blood plasma of pancreatic cancer patient added and the assay solution for the aberrant condition has a pH in the range of 6.4-6.8 and without any blood plasma of pancreatic cancer patient added.

The same component selected from the inorganic compounds, ions, and organic molecules may be used in each of the several types of assays discussed above. For example, in the case of lactic acid, the lactic acid may be used at substantially the same concentration in the pairs of assay solutions for both normal physiological condition and aberrant condition. The normal physiological condition and aberrant condition will then differ in one or more other aspects, such as temperature, pH, concentration of another component, etc. In a different embodiment, the lactic acid may be used as one of the differentiating factors between the normal physiological condition and aberrant condition to reflect the fact that the lactic acid has a higher concentration in an aberrant tumor microenvironment than in a normal physiological condition (a non-tumor microenvironment).

In some embodiments, the two or more components are added at substantially the same concentration to both assay solutions for normal physiological condition and aberrant condition. For example, both citrate and bovine serum albumin (BSA) are added to the assay solutions. The citrate concentration may be about 80 μM and the BSA concentration may be about 10-20% in both assay solutions. More specifically, the assay solution for the pair of assays under the normal physiological condition may have a pH in the range of 7.2-7.6, with citrate at a concentration of about 80 μM and BSA at a concentration about 10-20%. The assay solution for the pair of assays under the aberrant condition may have a pH in the range of 6.4-6.8, with citrate at a concentration of about 80 μM and BSA at a concentration about 10-20%.

In one embodiment, human serum may be added to both assay solutions for normal physiological condition and aberrant condition at substantially the same concentration. Because the human serum has a large number of inorganic compounds, ions, organic molecules (including proteins), the assay solutions will have multiple and large number of components selected from inorganic compounds, ions, organic molecules presented at substantially the same concentrations between the two assay solutions.

In some other embodiments, at least one of the two or more components is added to the assay solutions for normal physiological condition and aberrant condition at different concentrations. For example, both lactic acid and bovine serum albumin (BSA) are added to the assay solutions. The lactic acid concentration may be different between the assay solutions for the normal physiological condition and aberrant condition, while the BSA may have the same concentration in both assay solutions. The lactic acid may have a concentration in the range of from 30 to 50 mg/dL in the assay solution for the aberrant condition and concentration in the range of from 8-15 mg/dL in the assay solution for the normal physiological condition. On the other hand, the BSA has the same concentration in both assay solutions, such as about 10-20%. The conditionally active biologic protein thus selected from using these assay solutions is more active at high lactic acid concentration at 30-50 mg/dL than at low lactic acid concentration at 8-15 mg/dL in the presence of BSA.

In some embodiments, the assay solutions may be designed for selecting conditionally active biological proteins with an activity dependent on two or more conditions. In one exemplary embodiment, the conditionally active biologic protein may have activity dependent on both pH and lactic acid. The assay solutions for selecting such a conditionally active biologic protein may be an assay solution for the normal physiological condition with pH at 7.2-7.6, lactic acid at a concentration in the range of from 8 to 15 mg/dL. The assay solution for the aberrant condition may be with pH at 6.4-6.8, lactic acid at a concentration in the range of from 30 to 50 mg/dL. Optionally the assay solutions for both normal physiological condition and aberrant condition may also comprise an ion to assist the binding between the mutant protein and its binding partner, thus to increase the number of hits for candidate biologic active protein.

In yet another exemplary embodiment, the conditionally active biologic protein may have activity dependent on pH, glucose and lactic acid. The assay solutions for selecting such a conditionally active biologic protein may be an assay solution for the normal physiological condition with pH at 7.2-7.6, glucose at a concentration in the range of 2.5-10 mM, lactic acid at a concentration in the range of from 8 to 15 mg/dL. The assay solution for the aberrant condition may be with pH at 6.4-6.8, glucose at a concentration in the range of 0.05 to 0.5 mM, lactic acid at a concentration in the range of from 30 to 50 mg/dL. Optionally the assay solutions for both normal physiological condition and aberrant condition may also comprise an ion to assist the binding between the mutant proteins and their binding partner, thus to increase the number of candidate biological active protein binding to the binding partner at pH 6.4-6.8. The selected conditionally active biologic protein using such assay solutions is more active in an environment with pH 6.4-6.8, glucose concentration of 0.05 to 0.5 mM and lactic acid concentration of 30 to 50 mg/dL than in an environment with pH 7.2-7.6, glucose concentration of 2.5-10 mM and lactic acid concentration of 8 to 15 mg/dL.

The two or more components selected from inorganic compounds, ions, and organic molecules are for making an assay solution for the aberrant condition that simulates the environment at the location/site to which the selected conditionally active biologic protein will be delivered (i.e., targeted site). In some embodiments, at least three components presented in the environment at the targeted site may be added to the assay solution, or at least four components presented in the environment at the targeted site may be added to the assay solution, or at least five components presented in the environment at the targeted site may be added to the assay solution, or at least six components presented in the environment at the targeted site may be added to the assay solution.

In one embodiment, a fluid retrieved from the targeted site may be directly used as the assay solution for the assay under the aberrant condition. For example, synovial fluid may be retrieved from a subject, preferably from a subject with joint disease in need of treatment. The retrieved synovial fluid, optionally diluted, may be used as an assay solution in the pair of assays at the aberrant condition to select the conditionally active biologic protein. By using the retrieved synovial fluid, optionally diluted, as the assay solution for the assay under the aberrant condition, and an assay solution that simulates human blood plasma for the assay under the normal physiological condition, the conditionally active biologic protein (e.g., TNF-alpha) that is selected will be more active at the joint than at other locations or organs. For example, subjects with inflammatory joints (such as arthritis) may be treated with TNF-alpha. However, TNF-alpha typically has severe side effects of damaging other tissues and organs. A conditionally active TNF-alpha that is more active in the synovial fluid but not active or less active in blood will deliver the activity of TNF-alpha to the joints while reducing or potentially eliminating the side effects of the TNF-alpha on the rest of the body.

The development of conditionally active biologic protein that has an activity dependent on multiple conditions will result in improved selectivity of the conditionally active biologic protein to a target site in the body of a subject. Ideally, at other locations with only some of the conditions present the conditionally active biologic protein is not active or at least significantly less active. In one embodiment, the conditionally active biological protein that is active at pH 6.4-6.8, glucose concentration of 0.05 to 0.5 mM and lactic acid concentration of 30 to 50 mg/dL can be specifically delivered to a tumor microenvironment because these conditions are all present in the tumor microenvironment. Other tissues or organs may have one or two of these conditions present, thus not be sufficient to fully activate the conditionally active biologic protein in the other tissues or organs. For example, the exercised muscle may have a low pH in the range of 6.4-6.8. However, it may not have another assayed condition. Thus the conditionally active biologic protein is not active or at least less active in the exercised muscle.

In some embodiments, steps may be taken to confirm that the activity of the conditionally active biologic protein is truly dependent on the conditions used to select the conditionally active biologic protein. For example, the conditionally active biologic protein is selected to be dependent on three conditions: pH 6.4-6.8, glucose concentration of 0.05 to 0.5 mM and lactic acid concentration of 30 to 50 mg/dL. The selected conditionally active biologic protein may then be tested at each of the three conditions individually and in environments with pairs of the three conditions to confirm that the conditionally active biologic protein is not active or less active in these tests.

In some embodiments, certain components of serum may be purposely minimized or omitted from the assay media. For example, when screening antibodies, components of serum that bind with or adsorb antibodies can be minimized in or omitted from the assay media. Such bound antibodies may give false positives thereby including bound mutant antibodies that are not conditionally active but rather are merely bound to a component present in serum under a variety of different conditions. Thus, careful selection of assay components to minimize or omit components that can potentially bind with mutants in the assay can be used to reduce the number of non-functional mutants that may be inadvertently identified as positive for conditional activity due to binding to a component in the assay other than the desired binding partner. For example, in some embodiments where mutant proteins with a propensity to bond with components in human serum are being screened, BSA may be used in the assay solution in order to reduce or eliminate the possibility of false positives caused by mutant proteins bonding to components of human serum. Other similar replacements can also be made in particular cases to achieve the same goal.

Format of Screening

The screening step of the present invention may be any suitable method known to a person skilled in the art. Examples include ELISA, enzymatic activity assay, real tissue screening in vitro (organs, etc), tissue slides, whole animal, cell lines and use of 3D systems. For example, suitable cell-based assays are described in WO 2013/040445, tissue based assays are described in U.S. Pat. No. 7,993,271, whole animal based screening methods are described in US 2010/0263599, 3D system based screening methods are described in US 2011/0143960.

In some embodiments, the screening environment is the environment in the vicinity of a cell membrane such as inside, at or outside the cell membrane, or the environment in a joint. Some factors that may affect binding affinities when screening in a cell membrane environment include expression of receptors, internalization, antibody drug complex (ADC) potency, etc.

In some embodiments, the evolving step may produce mutant proteins that may simultaneously have other desired properties besides the conditionally active characteristics discussed above. Suitable other desired properties that may be evolved may include binding affinity, expression, humanization, etc. Therefore, the present invention may be employed to produce a conditionally active biologic protein that also has an improvement in at least one or more of these other desired properties.

In some embodiments, the present invention produces the conditionally active biologic protein. The selected conditionally active biologic protein may be further mutated using one of the mutagenesis techniques disclosed herein in, for example, a second evolving step, to improve another property of the selected conditionally active biologic protein such as binding affinity, expression, humanization, etc. After the second evolving step, the mutant proteins may be screened for both the conditional activity and the improved property.

In some embodiments, after evolving the wild-type protein to produce mutant proteins, a first conditionally active biologic protein is selected, which exhibits both: (a) a decrease in activity in an assay under the normal physiological condition compared to the wild-type protein, and (b) an increase in activity in the assay under an aberrant condition compared to the wild-type protein. The first conditionally active biologic protein may then be further subjected to one or more additional evolving, expressing and selecting steps to select at least a second conditionally active biologic protein that exhibits both: (a) a decrease in activity in an assay under the normal physiological condition compared to the wild-type protein, and (b) an increase in activity in the assay under an aberrant condition compared to the wild-type protein, as well as a larger ratio between the activity at the aberrant condition and the activity at the normal physiological condition, in comparison with the first conditionally active biologic protein and/or the wild-type.

In certain embodiments, the present invention is aimed at producing conditionally active biologic proteins with a large activity ratio of the activity at the aberrant condition and the activity at the normal physiological condition (e.g, a larger selectivity between the aberrant and normal physiologic conditions). The ratio, or selectivity, of the activity at the aberrant condition and the activity at the normal physiological condition may be at least about 2:1, or at least about 3:1, or at least about 4:1, or at least about 5:1, or at least about 6:1, or at least about 7:1, or at least about 8:1, or at least about 9:1, or at least about 10:1, or at least about 11:1, or at least about 12:1, or at least about 13:1, or at least about 14:1, or at least about 15:1, or at least about 16:1, or at least about 17:1, or at least about 18:1, or at least about 19:1, or at least about 20:1, or at least about 30:1, or at least about 40:1, or at least about 50:1, or at least about 60:1, or at least about 70:1, or at least about 80:1, or at least about 90:1, or at least about 100:1.

In one embodiment, conditionally active biologic protein is an antibody, which may have a ratio between the activity at the aberrant condition and the activity at the normal physiological condition of at least about 5:1, or at least about 6:1, or at least about 7:1, or at least about 8:1, or at least about 9:1, or at least about 10:1. In one embodiment, the conditionally active biologic protein is used to target a tumor site where the conditionally active biologic protein is active at the tumor site and significantly less active or inactive at a non-tumor site (normal physiological condition).

In one embodiment, the conditionally active biologic protein is an antibody that is intended to be conjugated with another agent such as those disclosed elsewhere herein. The conditionally active antibody may have a higher ratio of the activity at the aberrant condition and the activity at the normal physiological condition. For example, the conditionally active antibody that is to be conjugated with another agent may have a ratio of the activity at the aberrant condition to the activity at the normal physiological condition of at least about 10:1, or at least about 11:1, or at least about 12:1, or at least about 13:1, or at least about 14:1, or at least about 15:1, or at least about 16:1, or at least about 17:1, or at least about 18:1, or at least about 19:1, or at least about 20:1. This may be particularly important when the conjugated agent is, for example, toxic or radioactive, since such a conjugated agent is desirably concentrated at the disease or treatment site.

Engineering of Conditionally Active Antibodies

The conditionally active antibodies of the present invention may be engineered by one or more antibody engineering techniques described herein. Non-limiting examples of antibody engineering techniques include antibody conjugation, engineering of multispecific antibodies, and engineering of the Fc region of the antibodies.

Conjugating Conditionally Active Antibodies

The conditionally active antibodies provided by the present invention may be conjugated to a molecule. Because the conditionally active antibody preferentially acts in, for example, the brain, synovial fluid, a tumor microenvironment, or a stem cell niche, the conditionally active antibody may be conjugated to a molecule for the purpose of transporting the molecule to one of the brain, synovial fluid or a tumor microenvironment. In some embodiments, the conjugated molecule has some degree of toxicity, which toxicity may be reduced during transport through the body by conjugation to the conditionally active antibodies. As a result, the toxic agent may thus be influenced to preferentially act at the disease or treatment site.

The conjugation of the conditionally active antibody to a molecule such as a therapeutic or diagnostic agent, can be by covalent or non-covalent bonding. Covalent conjugation can either be direct or via a linker. In certain embodiments, direct conjugation is achieve by protein fusion (i.e., by genetic fusion of the two genes encoding the conditionally active antibody and neurological disorder drug and expression as a single protein). In certain embodiments, direct conjugation is by formation of a covalent bond between a reactive group on the conditionally active antibody and a corresponding group or acceptor on the molecule. In certain embodiments, direct conjugation is by modification (e.g., genetic modification) of one of the two molecules to be conjugated to include a reactive group (as non-limiting examples, a sulfhydryl group or a carboxyl group) that forms a covalent attachment to the other molecule to be conjugated under appropriate conditions. As one non-limiting example, a molecule (e.g., an amino acid) with a desired reactive group (e.g., a cysteine residue) may be introduced into the conditionally active antibody and a disulfide bond formed with a molecule such as a neurological drug. Methods for covalent conjugation of nucleic acids to proteins are known in the art (i.e., photocrosslinking, see, e.g., Zatsepin et al. *Russ. Chem. Rev.*, 74: 77-95 (2005)).

Non-covalent conjugation can be by any non-covalent attachment means, including hydrophobic bonds, ionic bonds, electrostatic interactions, and the like, as will be readily understood by one of ordinary skill in the art.

Conjugation may also be performed using a variety of linkers. For example, a conditionally active antibody and a neurological drug may be conjugated using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Peptide linkers, comprised of from one to twenty amino acids joined by peptide bonds, may also be used. In certain such embodiments, the amino acids are selected from the twenty naturally-occurring amino acids. In certain other such embodiments, one or more of the amino acids are selected from glycine, alanine, proline, asparagine, glutamine and lysine.

The linker may be a "cleavable linker" facilitating release of the neurological drug upon delivery to the treatment or disease site. For example, an acid-labile linker, peptidase-sensitive linker, photolabile linker, dimethyl linker or disulfide-containing linker (Chari et al., *Cancer Res.*, 52:127-131 (1992); U.S. Pat. No. 5,208,020) may be used. Some examples of cross-linker reagents for antibody conjugation include BMPS, EMCS, GMBS, HBVS, LC-SMCC, MBS, MPBH, SBAP, SIA, SLAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate).

The conjugated therapeutic agent may be toxic to the body, such as a radioactive particle, chemotherapy drug, or a cell toxin (i.e., cytotoxin). Using the conditionally active antibodies of the present invention to deliver the conjugated therapeutic agent to the disease site will significantly reduce the toxic effects of these therapeutic agents in areas of the body where their activity is undesirable. The technology for conjugating radioactive particles to antibodies is known in the art. Ibritumomab tiuxetan (Zevalin®) and tositumomab (Bexxar®) are examples of radioactive particle conjugated monoclonal antibodies. Both are antibodies against the CD20 antigen conjugated with a different radioactive particle. Similarly, the technology for conjugating chemotherapy drugs to antibodies is also known in the art. There are at least two marketed antibodies that are conjugated with a chemotherapy drug: brentuximab vedotin (Adcetris®) and ado-trastuzumab emtansine (Kadcyla™). The technology for conjugating a cell toxin to an antibody is also known in the art. For example, denileukin diftitox (Ontak®, a cancer drug) consists of an immune system protein known as interleukin-2 (IL-2) attached to a toxin from the germ that causes diphtheria.

It is contemplated that any kind of radioactive particles, chemotherapy drugs and cell toxins may be conjugated to the conditionally active antibody of the present invention in order to reduce the side effects of these agents during delivery of these agents to the treatment or disease site.

In some embodiments, the radioactive particles conjugated to the conditionally active antibodies comprise particles impregnated with one or more radioactive isotopes, and have sufficient radioactivity for locoregional ablation of cells. The particles may comprise glass, metal, resin, albumin, or polymer(s). Metals in the radioactive particles may be selected from iron, gadolinium, and calcium. Examples of the one or more radioactive isotopes in the radioactive particles are selected from Gallium-67 ($^{67}$Ga), Yttrium-90 ($^{90}$Y), Gallium-68 ($^{68}$Ga), Thallium-201 ($^{201}$Tl), Strontium-89 ($^{89}$Sr), Indium-III ($^{111}$In), Iodine-131 ($^{131}$I), Samarium-153 ($^{153}$Sm), Technetium-99m ($^{99m}$Tc), Rhenium-186 ($^{186}$Re), Rhenium-188 ($^{188}$Re), Copper-62 ($^{62}$Cu), and Copper-64 ($^{64}$Cu). Preferably the radioactive isotope(s) in the composition emit beta radiation, gamma radiation, and/or positrons.

In some embodiments, the chemotherapy drugs conjugated to the conditionally active antibodies are selected from anthracyclines, topoisomerase I and/or II inhibitors, spindle poison plant alkaloids, alkylating agents, anti-metabolites, ellipticine and harmine.

Anthracyclines (or anthracycline antibiotics) are derived from *Streptomyces* bacteria. These compounds are used to treat a wide range of cancers, including for example hepatocellular carcinoma, leukemias, lymphomas, and breast, uterine, ovarian, and lung cancers. Anthracyclines include, but are not limited to doxorubicin, daunorubicin, epirubicin, idarubicin, valrubicin, pirarubicin, zorubicin, aclarubicin, detorubicin, carminomycin, morpholinodoxorubicin, morpholinodaunorubicin, methoxymorpholinyldoxorubicin, and pharmaceutically acceptable salts thereof.

Topoisomerases are essential enzymes that maintain the topology of DNA. Inhibition of type I or type II topoisomerases interferes with both transcription and replication of DNA by upsetting proper DNA supercoiling. Some type I topoisomerase inhibitors include camptothecins derivatives Camptothecin derivatives refer to camptothecin analogs such as irinotecan, topotecan, hexatecan, silatecan, lurtotecan, karenitecin (BNP1350), gimatecan (ST1481), belotecan (CKD602), or their pharmaceutically acceptable salts. Examples of type II topoisomerase inhibitors include, but are not limited to, amsacrine, etoposide, etoposide phosphate and teniposide These are semisynthetic derivatives of epipodophyllotoxins, alkaloids naturally occurring in the root of American Mayapple (*Podophyllum peltatum*).

Spindle poison plant alkaloids are derived from plants and block cell division by preventing microtubule function, essential for cell division. These alkaloids include, but are not limited to, vinca alkaloids (like vinblastine, vincristine, vindesine, vinorelbine and vinpocetine) and taxanes. Taxanes include, but are not limited to, paclitaxel, docetaxel, larotaxel, cabazitaxel, ortataxel, tesetaxel, and their pharmaceutically acceptable salts.

Alkylating agents include, but are not limited to, mechlorethamine, cyclophosphamide, chlorambucil, ifosfamide and platinum compounds such as oxaliplatin, cisplatin or carboplatin.

An anti-metabolite is a chemical that inhibits the use of a metabolite, which is part of normal metabolism. The presence of anti-metabolites alters cell growth and cell division. Purine or pyrimidine analogues prevent the incorporation of nucleotides into DNA, stopping DNA synthesis and thus cell division. They also affect RNA synthesis. Examples of purine analogues include azathioprine, mercaptopurine, thioguanine, fludarabine, pentostatin and cladribine. Examples of pyrimidine analogues include 5-fluorouracil (5FU), which inhibits thymidylate synthase, floxuridine (FUDR) and cytosine arabinoside (Cytarabine).

Antifolates are chemotherapy drugs which impair the function of folic acids. A well-known example is Methotrexate, which is a folic acid analogue that inhibits the enzyme dihydrofolate reductase (DHFR), and thus prevents the formation of tetrahydrofolate. This leads to inhibited production of DNA, RNA and proteins (as tetrahydrofolate is also involved in the synthesis of amino acids serine and methionine). Other antifolates include, but are not limited to, trimethoprim, raltitrexed, pyrimethamine and pemetrexed.

Other chemotherapy drugs may also be conjugated to the conditionally active antibodies, such as ellipticine and harmine. Ellipticine and its derivatives such as 9-hydroxyellipticinium, N2-methyl-9-hydroxyellipticinium, 2-(diethyiamino-2-ethyl)9-hydroxyellipticinium acetate, 2-(diethyiamino-2-ethyl)9-hydroxy-ellipticinium acetate and 2-(beta piperidino-2-ethyl)9-hydroxyellipticinium are all effective chemotherapy drugs.

Harmine is a natural plant alkaloid product which was isolated from the *Peganum harmala* seeds. Harmine-based chemotherapy drugs include harmine, harmaline, harmol, harmalol and harman, and quinazoline derivatives: vasicine and vasicinone.

In some embodiments, the cell toxins conjugated to the conditionally active antibodies include taxol, cytochalasin B, gramicidin D, ethidium bromide, emetine, mitomycin, etoposide, tenoposide, vincristine, vinblastine, colchicin, doxorubicin, daunorubicin, dihydroxy anthracinedione, mitoxantrone, mithramycin, actinomycin D, 1-dehydrotestosterone, glucocorticoids, procaine, tetracaine, lidocaine, propranolol, and puromycin and analogs or homologs thereof. Other toxins include, for example, ricin, CC-1065 and analogues, the duocarmycins. Still other toxins include diptheria toxin, and snake venom (e.g., cobra venom).

In some embodiments, the conditionally active antibodies of the present invention may be conjugated to a diagnostic agent. A diagnostic agent used in the present invention can include any diagnostic agent known in the art, as provided, for example, in the following references: Armstrong et al, Diagnostic Imaging, 5$^{th}$ Ed., Blackwell Publishing (2004); Torchilin, V. P., Ed., Targeted Delivery of Imaging Agents, CRC Press (1995); Vallabhajosula, S., Molecular Imaging: Radiopharmaceuticals for PET and SPECT, Springer (2009). A diagnostic agent can be detected in a variety of ways, including using the agent to provide and/or enhance a detectable signal that includes, but is not limited to, a gamma-emission, a radioactive signal, an echogenic signal, an optical signal, a fluorescent signal, an absorptive signal, a magnetic signal or a tomography signal. Techniques for imaging the diagnostic agent can include, but are not limited to, single photon emission computed tomography (SPECT), magnetic resonance imaging (MRI), optical imaging, positron emission tomography (PET), computed tomography (CT), x-ray imaging, gamma ray imaging, and the like.

In some embodiments, a diagnostic agent can include chelators that bind, e.g., to metal ions to be used for a variety of diagnostic imaging techniques. Exemplary chelators include but are not limited to ethylenediaminetetraacetic acid (EDTA), [4-(1,4,8, 11-tetraazacyclotetradec-1-yl) methyl]benzoic acid (CPTA), Cyclohexanediaminetetraacetic acid (CDTA), ethylenebis(oxyethylenenitrilo)tetraacetic acid (EGTA), diethylenetriaminepentaacetic acid (DTPA), citric acid, hydroxyethyl ethylenediamine triacetic acid (HEDTA), iminodiacetic acid (IDA), triethylene tetraamine hexaacetic acid (TTHA), 1,4,7, 10-tetraazacyclodo-decane-1,4,7, 10-tetra(methylene phosphonic acid) (DOTP), 1,4,8, 11-tetraazacyclododecane-1,4,8, 11-tetraacetic acid (TETA), 1,4,7, 10-tetraazacyclododecane-1,4,7, 10-tetraacetic acid (DOTA), and chelating derivatives thereof.

A radioisotope can be incorporated into some of the diagnostic agents described herein and can include radionuclides that emit gamma rays, positrons, beta and alpha particles or X-rays. Suitable radionuclides include, but are not limited to, Ac, As, At, $^{n}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{123}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In certain embodiments, radioactive agents can include $^{m}$In-DTPA, $^{99m}$Tc(CO)3-DTPA, $^{99m}$Tc(CO)$_3$-ENPy2, $^{62/64/67}$Cu-TETA, $^{99m}$Tc(CO)$_3$-IDA, and $^{99m}$Tc(CO)$_3$ triamines (cyclic or linear). In other embodiments, the agents can include DOTA and its various analogs with $^{111}$In, $^{177}$Lu, $^{153}$Sm, $^{88/90}$Y, $^{62/64/67}$Cu, or $^{67/68}$Ga. In some embodiments, the liposomes can be radiolabeled, for example, by incorporation of lipids attached to chelates, such as a DTPA-lipid, as provided in the following references: Phillips et al, Wiley Interdisciplinary Reviews: *Nanomedicine and Nanobiotechnology*, vol. 1, pages 69-83 (2008); Torchilin, V. P. & Weissig, V., Eds. Liposomes 2nd Ed.: Oxford Univ. Press (2003); Elbayoumi, T. A. & Torchilin, V. P., *Eur. J. Nucl. Med. Mol. Imaging*, 33: 1196-1205 (2006); Mougin-Degraef, M. et al, *Int'l J. Pharmaceutics*, 344: 110-1 17 (2007).

In other embodiments, the diagnostic agents may include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives having the general structure of 4,4-difluoro-4-bora-3a,4a-diaza-s-indacene, and/or conjugates and/or derivatives of any of these. Other agents that can be used include, but are not limited to, for example, fluorescein, fluorescein-polyaspartic acid conjugates, fluorescein-polyglutamic acid conjugates, fluorescein-polyarginine conjugates, indocyanine green, indocyanine-dodecaaspartic acid conjugates, indocyanine (NIRD)-polyaspartic acid conjugates, isosulfan blue, indole disulfonates, benzoindole disulfonate, bis(ethylcarboxymethyl)indocyanine, bis(pentylcarboxymethyl)indocyanine, polyhydroxyindole sulfonates, polyhydroxybenzoindole sulfonate, rigid heteroatomic indole sulfonate, indocyaninebispropanoic acid, indocyaninebishexanoic acid, 3,6-dicyano-2,5-[(N,N,N',N'-tetrakis(carboxymethyl)amino] pyrazine, 3,6-[(N,N,N',N'-tetrakis(2-hydroxyethyl)amino] pyrazine-2,5-dicarboxylic acid, 3,6-bis(N-azatedino) pyrazine-2,5-dicarboxylic acid, 3,6-bis(N-morpholino) pyrazine-2,5-dicarboxylic acid, 3,6-bis(N-piperazino) pyrazine-2,5-dicarboxylic acid, 3,6-bis(N-thiomorpholino) pyrazine-2,5-dicarboxylic acid, 3,6-bis(N-thiomorpholino) pyrazine-2,5-dicarboxylic acid S-oxide, 2,5-dicyano-3,6-bis (N-thiomorpholino)pyrazine S,S-dioxide, indocarbocyaninetetrasulfonate, chloroindocarbocyanine, and 3,6-diaminopyrazine-2,5-dicarboxylic acid.

In yet other embodiments, the diagnostic agents may include contrast agents that are generally well known in the art, including, for example, superparamagnetic iron oxide (SPIO), complexes of gadolinium or manganese, and the like. (See, e.g., Armstrong et al, Diagnostic Imaging, 5$^{th}$ Ed., Blackwell Publishing (2004)). In some embodiments, a diagnostic agent can include a magnetic resonance (MR) imaging agent. Exemplary magnetic resonance imaging agents include, but are not limited to, paramagnetic agents, superparamagnetic agents, and the like. Exemplary paramagnetic agents can include, but are not limited torn Gadopentetic acid, Gadoteric acid, Gadodiamide, Gadolinium, Gadoteridol, Mangafodipir, Gadoversetamide, Ferric ammonium citrate, Gadobenic acid, Gadobutrol, or Gadoxetic acid. Superparamagnetic agents can include, but are not limited to, superparamagnetic iron oxide and Ferristene. In certain embodiments, the diagnostic agents can include x-ray contrast agents as provided, for example, in the following references: H. S Thomsen, R. N. Muller and R. F. Mattrey, Eds., Trends in Contrast Media, (Berlin: Springer-Verlag, 1999); P. Dawson, D. Cosgrove and R. Grainger, Eds., Textbook of Contrast Media (ISIS Medical Media 1999); Torchilin, V. P., *Curr. Pharm. Biotech.*, vol. 1, pages 183-215 (2000); Bogdanov, A. A. et al, *Adv. Drug Del. Rev.*, Vol. 37, pages 279-293 (1999); Sachse, A. et ah, *Investigative Radiology*, vol. 32, pages 44-50 (1997). Examples of x-ray contrast agents include, without limitation, iopamidol, iomeprol, iohexol, iopentol, iopromide, iosimide, ioversol, iotrolan, iotasul, iodixanol, iodecimol, ioglucamide, ioglunide, iogulamide, iosarcol, ioxilan, iopamiron, metrizamide, iobitridol and iosimenol. In certain embodiments, the x-ray contrast agents can include iopamidol, iomeprol, iopromide, iohexol, iopentol, ioversol, iobitridol, iodixanol, iotrolan and iosimenol.

In some embodiments, the conditionally active antibody may be conjugated to a protein, such as interleukins, cytokines, enzymes, growth factors, or other antibodies. Some examples of such proteins include, for example, tumor necrosis factor, α-interferon (EFN-α), β-interferon (IFN-β), nerve growth factor (NGF), platelet derived growth factor (PDGF), tissue plasminogen activator (TPA), an apoptotic agent (e.g., TNF-α, TNF-β, AIM I as disclosed in WO 97/33899), AIM II (see WO 97/34911), Fas Ligand (Takahashi et al., *J. Immunol.*, vol. 6, pages 1567-1574, 1994), and VEGI (WO 99/23105), a thrombotic agent or an anti-angiogenic agent (e.g., angiostatin or endostatin); or a biological response modifier such as, for example, a lymphokine (e.g., interleukin-1 ("IL-I"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

In some embodiments, the conditionally active antibodies for crossing the blood-brain barrier (BBB) may be conjugated to a drug for treating a neurological disorder. The drug will be transported across BBB with the antibodies and remain in the brain for treating the neurological disorder. The neurological disorder refers to a disease or disorder which affects the central nervous system (CNS) and/or which has an etiology in the CNS. Exemplary CNS diseases or disorders include, but are not limited to, neuropathy, amyloidosis, cancer, an ocular disease or disorder, viral or microbial infection, inflammation, ischemia, neurodegenerative disease, seizure, behavioral disorders, and a lysosomal storage disease.

For the purposes of this application, the CNS will be understood to include the eye, which is normally sequestered from the rest of the body by the blood-retina barrier. Specific examples of neurological disorders include, but are not limited to, neurodegenerative diseases such as Lewy body disease, postpoliomyelitis syndrome, Shy-Draeger syndrome, olivopontocerebellar atrophy, Parkinson's disease, multiple system atrophy, striatonigral degeneration, tauopathies such as Alzheimers disease and supranuclear palsy, prion diseases such as bovine spongiform encephalopathy, scrapie, Creutzfeldt-Jakob syndrome, kuru, Gerstmann-Straussler-Scheinker disease, chronic wasting disease, and fatal familial insomnia, bulbar palsy, motor neuron disease, and nervous system heterodegenerative disorders such as Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome, dementia including, but not limited to, Pick's disease, and spinocerebellar ataxia), cancer (e.g. of the CNS and/or brain, including brain metastases resulting from cancer elsewhere in the body).

The drug for treating the neurological disorder may include, but is not limited to, antibodies, peptides, proteins, natural ligands of one or more CNS target(s), modified versions of natural ligands of one or more CNS target(s), aptamers, inhibitory nucleic acids (i.e., small inhibitory RNAs (siRNA) and short hairpin RNAs (shRNA)), ribozymes, and small molecules, or active fragments of any of the foregoing. Exemplary neurological disorder drugs include, but are not limited to: antibodies, aptamers, proteins, peptides, inhibitory nucleic acids and small molecules and active fragments of any of the foregoing that either are themselves or specifically recognize and/or act upon (i.e., inhibit, activate, or detect) a CNS antigen or target molecule such as, but not limited to, amyloid precursor protein or portions thereof, amyloid beta, beta-secretase, gamma-secretase, tau, alpha-synuclein, parkin, huntingtin, DR6, presenilin, ApoE, glioma or other CNS cancer markers, and neurotrophins. Non-limiting examples of neurological disorder drugs and disorders they may be used to treat include anti-BACE1 antibody for treating Alzheimer's, acute and chronic brain injury, stroke; anti-Abeta antibody for treating Alzheimer's disease; neurotrophin for treating stroke, acute brain injury, spinal cord injury; brain-derived neurotrophic factor (BDNF) and fibroblast growth factor 2 (FGF-2) for treating chronic brain injury (neurogenesis); anti-Epidermal Growth Factor Receptor (EGFR)-antibody for treating brain cancer; Glial cell-line derived neural factor (GDNF) for treating Parkinson's disease; brain-derived neurotrophic factor (BDNF) for treating Amyotrophic lateral sclerosis and depression; lysosomal enzyme for treating lysosomal storage disorders of the brain; Ciliary neurotrophic factor (CNTF) for treating Amyotrophic lateral sclerosis; Neuregulin-1 for treating Schizophrenia; and anti-HER2 antibody (e.g. trastuzumab) for treating brain metastasis from HER2-positive cancer.

In some embodiments, the conditionally active antibodies may be conjugated on the Fc region of the antibodies. The conjugating molecules, compounds or drugs described above may be conjugated to the Fc region, as described in U.S. Pat. No. 8,362,210. For example, the Fc region may be conjugated to a cytokine or a toxin to be delivered to the site where the conditionally active antibody displays preferential activity. Methods for conjugating polypeptides to the Fc region of antibodies are known in the art. See, e.g., U.S. Pat. Nos. 5,336,603, 5,622,929, 5,359,046, 5,349,053, 5,447, 851, 5,723,125, 5,783,181, 5,908,626, 5,844,095, and 5,112, 946; EP 307,434; EP 367,166; EP 394,827; WO 91/06570, WO 96/04388, WO 96/22024, WO 97/34631, and WO 99/04813; Ashkenazi et al., *Proc. Natl. Acad. Sci. USA*, vol. 88, pages 10535-10539, 1991; Traunecker et al., *Nature*, vol. 331, pages 84-86, 1988; Zheng et al., *J. Immunol.*, vol. 154, pages 5590-5600, 1995; and Vil et al., *Proc. Natl. Acad. Sci. USA*, vol. 89, pages 11337-11341, 1992.

In one embodiment, the conditionally active antibody used for the conjugation disclosed herein preferably has a ratio of the activity at the aberrant condition to the activity at the normal physiological condition at least about 10:1, or at least about 12:1, or at least about 14:1, or at least about 16:1, or at least about 18:1, or at least about 20:1, or at least about 22:1, or at least about 24:1, or at least about 26:1.

In some embodiments, the conditionally active antibody may be covalently attached to the conjugated agent through an intermediate linker having at least two reactive groups, one to react with the conditionally active antibody and one to react with the conjugated agent. The linker, which may include any compatible organic compound, can be chosen such that the reaction with conditionally active antibody or conjugated agent does not adversely affect reactivity and/or selectivity of the conditionally active antibody. Furthermore, the attachment of linker to conjugated agent might not destroy the activity of the conjugated agent.

Suitable linkers for oxidized conditionally active antibodies include those containing a group selected from primary amines, secondary amines, hydrazine, hydrazide, hydroxylamines, phenylhydrazine, semicarbazide and thiosemicarbazide groups. Suitable linkers for reduced conditionally active antibodies include those having certain reactive groups capable of reaction with a sulfhydryl group of a reduced conditionally active antibody. Such reactive groups include, but are not limited to: reactive haloalkyl groups (including, for example, haloacetyl groups), p-mercuribenzoate groups and groups capable of Michael-type addition reactions (including, for example, maleimides and groups of the type described by Mitra and Lawton, *J. Amer. Chem. Soc.* Vol. 101, pages 3097-3110, 1979).

Engineering Multispecific Conditionally Active Antibodies

The multispecific antibody is an antibody with polyepitopic specificity. Multispecific antibodies include, but are not limited to, an antibody comprising a heavy chain variable domain ($V_H$) and a light chain variable domain ($V_L$), where the $V_H V_L$ unit has polyepitopic specificity, antibodies having two or more $V_L$ and $V_H$ domains where each $V_H V_L$ unit binds to a different epitope, antibodies having two or more single variable domains with each single variable domain binding to a different epitope, and antibodies comprising one or more antibody fragments as well as antibodies comprising antibody fragments that have been linked covalently or non-covalently.

To construct multispecific antibodies, including bispecific antibodies, antibody fragments having at least one free sulfhydryl group are obtained. The antibody fragments may be obtained from full-length conditionally active antibodies. The conditionally active antibodies may be digested enzymatically to produce antibody fragments. Exemplary enzymatic digestion methods may employ pepsin, papain and Lys-C. Exemplary antibody fragments include, but are not limited to, Fab, Fab', F(ab')2, Fv, diabodies (Db); tandem diabodies (taDb), linear antibodies (see U.S. Pat. No. 5,641,870, Example 2; Zapata et al., *Protein Eng.*, vol. 8, pages 1057-1062 (1995)); one-armed antibodies, single variable domain antibodies, minibodies (Olafsen et al (2004) *Protein Eng. Design & Sel.*, vol. 17, pages 315-323), single-chain antibody molecules, fragments produced by a Fab expression library, anti-idiotypic (anti-Id) antibodies, CDR (complementary determining region), and epitope-binding fragments. Antibody fragments may also be produced using DNA recombinant technology. The DNA encoding the antibody fragments may be cloned into plasmid expression vectors or phagemid vectors and expressed directly in *E. coli*. Antibody enzymatic digestion methods, DNA cloning and recombinant protein expression methods are well known to those skilled in the art.

Antibody fragments may be purified using conventional techniques and are subjected to reduction to generate a free thiol group. Antibody fragments having a free thiol group are reacted with a crosslinker, for example, bis-maleimide. Such crosslinked antibody fragments are purified and then reacted with a second antibody fragment having a free thiol group. The final product in which two antibody fragments are crosslinked is purified. In certain embodiments, each antibody fragment is a Fab and the final product, in which the two Fabs are linked through bis-maleimide, is referred to herein as bismaleimido-(thio-Fab)2, or bis-Fab. Such multispecific antibodies and antibody analogs, including bis-Fabs, can be exploited to quickly synthesize a large number of antibody fragment combinations, or structural variants of native antibodies or particular antibody fragment combinations.

Multispecific antibodies can be synthesized with modified cross-linkers such that additional functional moieties may be attached to the multispecific antibody. Modified crosslinkers allow for attachment of any sulfhydryl-reactive moiety. In one embodiment, N-succinimidyl-S-acetylthioacetate (SATA) is attached to bis-maleimide to form bis-maleimidoacetylthioacetate (BMata). After deprotection of the masked thiol group, any functional group having a sulfhydryl-reactive (or thiol-reactive) moiety may be attached to the multispecific antibodies.

Exemplary thiol-reactive reagents include a multifunctional linker reagent, a capture reagent, i.e. affinity, a label reagent (e.g. a biotin-linker reagent), a detection label (e.g. a fluorophore reagent), a solid phase immobilization reagent (e.g. SEPHAROSE™, polystyrene, or glass), or a drug-linker intermediate. One example of a thiol-reactive reagent is N-ethyl maleimide (NEM). Such multispecific antibodies or antibody analogs having modified crosslinkers may be further reacted with a drug moiety reagent or other label. Reaction of a multispecific antibody or antibody analog with a drug-linker intermediate provides a multispecific antibody drug conjugate or antibody analog drug conjugate, respectively.

Many other techniques for making multispecific antibodies may also be used in the present invention describing these techniques include: (1) Milstein and Cuello, *Nature*, vol. 305, page 537 (1983)), WO 93/08829, and Traunecker et al., *EMBO J.*, vol. 10, page 3655 (1991) on recombinant co-expression of two immunoglobulin heavy chain-light chain pairs having different specificities; (2) U.S. Pat. No. 5,731,168 on "knob-in-hole" engineering; (3) WO 2009/089004A1 on engineering electrostatic steering effects for making antibody Fc-heterodimeric molecules; (4) U.S. Pat. No. 4,676,980, and Brennan et al., *Science*, vol. 229, page 81 (1985) on cross-linking two or more antibodies or fragments; (5) Kostelny et al., *J. Immunol.*, vol. 148, pages 1547-1553 (1992) on using leucine zippers to produce bi-specific antibodies; (6) Hollinger et al., *Proc. Natl. Acad. Sci. USA*, vol. 90, pages 6444-6448 (1993) on using "diabody" technology for making bispecific antibody fragments; (7) Gruber et al., *J. Immunol.*, vol. 152, page 5368 (1994) on using single-chain Fv (sFv) dimers; (8) Tutt et al. *J. Immunol.* 147: 60 (1991) on preparing trispecific antibodies; and (9) US 2006/0025576A1 and Wu et al. *Nature Biotechnology*, vol. 25, pages 1290-1297 (2007) on engineered antibodies with three or more functional antigen binding sites, including "Octopus antibodies" or "dual-variable domain immunoglobulins" (DVDs).

In one embodiment, the conditionally active antibody for crossing the BBB is engineered to make a multispecific antibody (e.g. a bispecific antibody). This multispecific antibody comprises a first antigen binding site which binds a BBB-R and a second antigen binding site which binds a brain antigen. At least the first antigen binding site for BBB-R is conditionally active. A brain antigen is an antigen expressed in the brain, which can be targeted with an antibody or small molecule. Examples of such antigens include, without limitation: beta-secretase 1 (BACE1), amyloid beta (Abeta), epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), and caspase 6. In one embodiment, the antigen is BACE1.

Multispecific antibodies may have a high selectivity at preferentially targeting tissues containing all or most of the targets (antigens) that the multispecific antibody can bind to. For example, a bispecific antibody may provide selectivity for target cells by displaying a greater preference to target cells that express both of the antigens recognized by the bispecific antibody, in comparison with non-target cells that may express only one of the antigens. Therefore, due to the dynamism of this system, there are more bispecific antibodies being bound to the target cells than non-target cells at equilibrium.

Engineering a Bi-Specific Conditionally Active Antibody Against an Immune Effector-Cell Surface Antigen and a Target Antigen The bi-specific conditionally active antibodies of the invention can attract an immune effector cell to a disease site with the target antigen present. The bi-specific conditionally active antibody is an antibody that can specifically bind to two different antigens: the immune effector-cell surface antigen and the target antigen. The bi-specific antibody may be a full length antibody comprising two arms with one arm binding to the immune effector-cell surface antigen and the other arm binding to the target antigen. The bi-specific antibody may be an antibody fragment comprising only heavy chain variable domains ($V_H$) and light chain variable domains ($V_L$). In one embodiment, the antibody fragment includes at least two $V_H V_L$ units: one for binding to the immune effector-cell surface antigen and the other arm binding to the target antigen. In another embodiment, the antibody fragment includes at least two single variable domains ($V_H$ or $V_L$): one for binding to the immune effector-cell surface antigen and the other arm binding to the target antigen. In some embodiments, the bi-specific conditionally active antibody comprises two scFvs: one binding to the immune effector-cell surface antigen and the other binding to the target antigen.

The attracted immune effector cell, with its binding activity to both an immune effector-cell and a target antigen on diseased cells or diseased tissue, can attract the immune effector-cell to the diseased cells or diseased tissues containing the target antigen. The attracted immune effector-cell will then attack the diseased cells or diseased tissues, thus helping to cure the disease because the immune effector cell is capable of suppressing or even destroying the diseased cells or diseased tissue. For example, the immune effectors cell can destroy tumor cells or infected cells. The immune effector cells include natural killer cells, macrophages, lymphokine-activated killer (LAK) cells and T-cells.

The bi-specific conditionally active antibody has two binding activities, one each to the immune effector-cell surface antigen and the target antigen. In one embodiment, both binding activities are conditional, meaning that the binding activities of the bi-specific conditionally active antibody to the immune effector-cell surface antigen and the target antigen are lower than the binding activities of a wild-type antibody under a normal physiological condition and higher than the wild-type antibody under an aberrant condition. In one embodiment, only one of two binding activities are conditional, meaning that either the binding activity of the bi-specific conditionally active antibody to the immune effector-cell surface antigen or the binding activity of the bi-specific conditionally active antibody to the target antigen is conditional. In this case one of the binding activity of the bi-specific conditionally active antibody to the immune effector-cell surface antigen or the binding activity of the bi-specific conditionally active antibody to the target antigen is lower than the corresponding activity of a wild-type antibody under a normal physiological condition and higher than the corresponding activity of the wild-type antibody under an aberrant condition.

The two arms (e.g., two $V_H V_L$ units or two scFvs) in the bi-specific conditionally active antibody may be joined by means of conventional methods. As is well known in the field, the minimum antibody fragment containing a complete antigen binding site has a dimer of one heavy and one light chain variable domain ($V_H$ and $V_L$) in non-covalent association. This configuration corresponds to the one found in native antibodies where three complementarity determining regions (CDRs) of each variable domain interact to define an antigen binding site on the surface of the $V_H$—$V_L$ dimer. Collectively, the six CDRs confer antigen binding specificity to the antibody. Frameworks (FRs) flanking the CDRs have a tertiary structure that is essentially conserved in native immunoglobulins of species as diverse as human and mouse. These FRs serve to hold the CDRs in their appropriate orientation. The constant domains are not required for binding function, but may aid in stabilizing $V_H$-$V_L$ interaction. Even a single variable domain (or half of an Fv comprising only three CDRs specific for an antigen) has the ability to recognize and bind antigen, although usually at a lower affinity than an entire binding site (Painter et al., "Contributions of heavy and light chains of rabbit immunoglobulin G to antibody activity. I. Binding studies on isolated heavy and light chains," *Biochemistry*, vol. 11 pages 1327-1337, 1972). Hence, said domain of the binding site of the bi-specific conditionally active antibody may be constructed as a pair of $V_H$—$V_L$, $V_H$—$V_H$ or $V_L$—$V_L$ domains of different immunoglobulins.

In some embodiments, the bi-specific conditionally active antibody may be constructed as a contiguous polypeptide chain by means of recombinant DNA techniques, e.g. in such a way that a nucleic acid molecule coding for bi-specific conditionally active antibody is expressed in order to construct a contiguous polypeptide chain (e.g., see Mack et al., "A small bispecific antibody construct expressed as a functional single-chain molecule with high tumor cell cytotoxicity," *Proc. Natl. Acad. Sci. USA*, vol. 92, pages 7021-7025, 2005). The order of $V_H$ and $V_L$ domains within the polypeptide chain is not critical for the present invention, as long as the $V_H$ and $V_L$ domains are arranged so that the antigen binding sites can properly fold to form one binding site for the immune effector-cell surface antigen and one binding site for the target antigen.

Some of the techniques described herein for engineering multi-specific conditionally active antibodies may be used in generating bi-specific conditionally active antibody against the immune effector cell surface antigen and target antigen.

Bi-specific antibodies configured as a single polypeptide chain are known in the art and are described in WO 99/54440, Mack, *J. Immunol.* (1997), 158, 3965-3970, Mack, *PNAS*, (1995), 92, 7021-7025, Kufer, *Cancer Immunol. Immunother.*, (1997), 45, 193-197, Loffler, *Blood*, (2000), 95, 6, 2098-2103, Bruhl, *J. Immunol.*, (2001), 166, 2420-2426. A particularly preferred configuration for the bi-specific antibody is a polypeptide construct wherein the $V_H$ and $V_L$ regions are linked to each other by a linker-domain. The order of the $V_H$ and $V_L$ regions in the single polypeptide chain is not critical. In one embodiment, the single polypeptide chain is configured as $V_{H1}$-linker domain-$V_{L1}$-linker domain-$V_{H2}$-linker domain-$V_{L2}$. In another embodiment, the single polypeptide chain is configured as $V_{L1}$-linker domain-$V_{H1}$-linker domain-$V_{L2}$-linker domain-$V_{H2}$. In another embodiment, the single polypeptide chain is configured as $V_{H1}$-linker domain-$V_{H2}$-linker domain-$V_{L1}$-linker domain-$V_{L2}$. In another embodiment, the single polypeptide chain is configured as $V_{H1}$-linker domain-$V_{L2}$-linker domain-$V_{L1}$-linker domain-$V_{H2}$. The single polypeptide chain can fold into two arms with each capable of binding with the immune effector cell surface antigen or the target antigen.

The linker domain in the bi-specific conditionally active antibody is a peptide fragment long enough to allow intermolecular association between these $V_H$ and $V_L$ domains. The design of linkers suitable for this purpose is described in the prior art, for example in EP 623 679 B1, U.S. Pat. No. 5,258,498, EP 573 551 B1 and U.S. Pat. No. 5,525,491. The linker domain is preferably a hydrophilic flexible linker of 1 to 25 amino acids selected from a Glycine, a Serine and/or a Glycine/Serine. In one embodiment, the linker domain is a 15 amino acid linker of sequence $(Gly_4Ser)_3$.

Additional linker domains comprise oligomerization domains. Oligomerization domains can facilitate the combination of two or several $V_H$ and $V_L$ domains thereof folding into the two arms with each capable of binding with the immune effector cell surface antigen or the target antigen. Non-limiting examples of oligomerization domains comprise leucine zippers (like jun-fos, GCN4, E/EBP; Kostelny, J. *Immunol.* 148 (1992), 1547-1553; Zeng, *Proc. Natl. Acad. Sci.* 94 (1997), 3673-3678, Williams, *Genes Dev.* 5 (1991), 1553-1563; Suter, "Phage Display of Peptides and Proteins", Chapter 11, (1996), Academic Press), antibody-derived oligomerization domains, like constant domains CH1 and CL (Mueller, *FEBS Letters* 422 (1998), 259-264) and/or tetramerization domains like GCN4-LI (Zerangue, *Proc. Natl. Acad. Sci.* 97 (2000), 3591-3595).

In some embodiments, knob-in-hole technology may be used to stabilize the folding of the single polypeptide chain bi-specific conditionally antibody. Knob-in-hole technology is described by Ridgway et al., ("Knobs-into-holes' engineering of antibody CH3 domains for heavy chain heterodimerization," *Protein Eng.* 1996 July; 9(7):617-21). This approach has been used for the packing of amino acid side chains between adjacent a-helices, where the side chains of residues in an a-helix are represented as spaced knobs on the surface of a cylinder alternating with holes in which knobs of an adjacent a-helix might fit (O'Shea et al., (1991) Science, 254, 539-544).

The immune effector-cell surface antigens should be specific to one or a class of immune effector cells. The surface antigens for many of the immune effector cells are known. The natural killer cells have surface antigens including CD56, CD8, CD16, KIR family receptors, NKp46, NKp30, CD244 (2B4), CD161, CD2, CD7, CD3, and killer cell immunoglobulin-like receptors (Angelis et al., "Expansion of CD56-negative, CD16-positive, KIR-expressing natural killer cells after T cell-depleted haploidentical hematopoietic stem cell transplantation," *Acta Haematol.* 2011; 126(1):13-20; Dalle et al., "Characterization of Cord Blood Natural Killer Cells: Implications for Transplantation and Neonatal Infections," *Pediatric Research* (2005) 57, 649-655; Agarwal et al., "Roles and Mechanism of Natural Killer Cells in Clinical and Experimental Transplantation," *Expert Rev Clin Immunol.* 2008; 4(1):79-91).

The macrophages have a surface antigen including CD11b, F4/80, CD68, CSF1R, MAC2, CD11c, LY6G, LY6C, IL-4Ra, CD163, CD14, CD11b, F4/80 (mice)/EMR1 (human), CD68 and MAC-1/MAC-3, PECAM-1 (CD31), CD62, CD64, CD45, Ym1, CD206, CD45RO, 25F9, S100A8/A9, and PM-2K (Murray et al., "Protective and pathogenic functions of macrophage subsets," *Nature Reviews Immunology*, 11, 723-737; Taylor et al., "Macrophage receptors and immune recognition," *Annu Rev Immunol* 2005; 23:901-44; Pilling, et al., "Identification of Markers that Distinguish Monocyte-Derived Fibrocytes from Monocytes, Macrophages, and Fibroblasts," *PLoS ONE* 4(10): e7475. doi:10.1371/journal.pone.0007475, 2009).

The lymphokine-activated killer (LAK) cells have a surface antigen including T3, T4 T11, T8, TII, Leu7, Leu11 (Ferrini et al., "Surface markers of human lymphokine-activated killer cells and their precursors," Int J Cancer. 1987 Jan. 15; 39(1):18-24; Bagnasco et al., "Glycoproteic nature of surface molecules of effector cells with lymphokine-activated killer (LAK) activity," Int J Cancer. 1987 Jun. 15; 39(6):703-7; Kaufmann et al., "Interleukin 2 induces human acute lymphocytic leukemia cells to manifest lymphokine-activated-killer (LAK) cytotoxicity," The Journal of Immunology, Aug. 1, 1987, vol. 139 no. 3 977-982).

The T-cells, especially cytotoxic T-cells, have a surface antigen including CD2, CD3, CD4, CD5, CD6, CD8, CD28, T58, CD27, CD45, CD84, CD25, CD127, and CD196 (CCR6), CD197 (CCR7), CD62L, CD69, TCR, T10, T11, and CD45RO (Ledbetter et al, "Enhanced transmembrane signalling activity of monoclonal antibody heteroconjugates suggests molecular interactions between receptors on the T cell surface," *Mol Immunol.* 1989 February; 26(2):137-45; Jondal et al., "SURFACE MARKERS ON HUMAN T AND B LYMPHOCYTES," *JOURNAL OF EXPERIMENTAL MEDICINE*, VOLUME 136, 1972, 207-215; Mingari et al., "Surface markers of human T lymphocytes," *Ric Clin Lab.* 1982 July-September; 12(3):439-448).

The bi-specific conditionally active antibody, after binding with an immune effector cell, can bring the immune effector cell to a cell or tissue where the target antigen is present, preferably on the surface. Once the bi-specific conditionally active antibody (with the immune effector cell) binds with the target antigen, the immune effector cell can attack the diseased cell or diseased tissue. The immune effector cells, such as natural killer cells, macrophages, LAK cells, T-cells (cytotoxic), are all capable of killing and/or destroying a diseased cell or tissue, for example, destroying tumor tissue.

The diseased cells or diseased tissue may be selected from cancer, inflammatory disease, neuronal-disorders, diabetes, cardiovascular disease, or infectious diseases. Examples of target antigens include antigens expressed by various immune cells, carcinomas, sarcomas, lymphomas, leukemia, germ cell tumors, blastomas, and cells associated with various hematologic diseases, autoimmune diseases, and/or inflammatory diseases.

The target antigens specific for a cancer which may be targeted by the bi-specific conditionally active antibody include one or more of 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DRS, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, LI-CAM, IL-13, IL-6, insulin-like growth factor I receptor, integrin $\alpha5\beta1$, integrin $\alpha v\beta3$, MORAb-009, MS4A1, MUC1, mucin CanAg, N-glycolylneuraminic acid, NPC-1C, PDGF-R a, PDL192, phosphatidylserine, prostatic carcinoma cells, RANKL, RON, ROR1, SCH 900105, SDC1, SLAMF7, TAG-72, tenascin C, TGF beta 2, TGF-$\beta$, TRAIL-R1, TRAIL-R2, tumor antigen CTAA16.88, VEGF-A, VEGFR-1, VEGFR2 or vimentin.

The types of cancers to be treated with the genetically engineered cytotoxic cells or pharmaceutical compositions of the invention include, carcinoma, blastoma, and sarcoma, and certain leukemia or lymphoid malignancies, benign and malignant tumors, and malignancies e.g., sarcomas, carcinomas, and melanomas. The cancers may be non-solid tumors (such as hematological tumors) or solid tumors. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors that may be treated include sarcomas and carcinomas, including fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Target antigens specific for inflammatory diseases which may be targeted by the bi-specific conditionally active antibody include one or more of AOC3 (VAP-1), CAM-3001, CCL11 (eotaxin-1), CD125, CD147 (basigin), CD154 (CD40L), CD2, CD20, CD23 (IgE receptor), CD25 (a chain of IL-2 receptor), CD3, CD4, CD5, IFN-α, IFN-γ, IgE, IgE Fc region, IL-1, IL-12, IL-23, IL-13, IL-17, IL-17A, IL-22, IL-4, IL-5, IL-5, IL-6, IL-6 receptor, integrin a4, integrin α4β7, Lama glama, LFA-1 (CD1 la), MEDI-528, myostatin, OX-40, rhuMAb β7, scleroscin, SOST, TGF beta 1, TNF-α or VEGF-A.

Target antigens specific for neuronal disorders which may be targeted by the bi-specific conditionally active antibody of the invention include one or more of beta amyloid or MABT5102A. Antigens specific for diabetes which may be targeted by the bi-specific conditionally active antibody of the invention include one or more of L-Iβ or CD3. Antigens specific for cardiovascular diseases which may be targeted by the bi-specific conditionally active antibody of the invention include one or more of C5, cardiac myosin, CD41 (integrin alpha-lib), fibrin II, beta chain, ITGB2 (CD 18) and sphingosine-1-phosphate.

Target antigens specific for infectious diseases which may be targeted by the bi-specific conditionally active antibody of the invention include one or more of anthrax toxin, CCR5, CD4, clumping factor A, cytomegalovirus, cytomegalovirus glycoprotein B, endotoxin, *Escherichia coli*, hepatitis B surface antigen, hepatitis B virus, HIV-1, Hsp90, Influenza A hemagglutinin, lipoteichoic acid, *Pseudomonas aeruginosa*, rabies virus glycoprotein, respiratory syncytial virus and TNF-α.

Further examples of target antigens include surface proteins found on cancer cells in a specific or amplified fashion, e.g. the IL-14 receptor, CD19, CD20 and CD40 for B-cell lymphoma, the Lewis Y and CEA antigens for a variety of carcinomas, the Tag72 antigen for breast and colorectal cancer, EGF-R for lung cancer, folate binding protein and the HER-2 protein which is often amplified in human breast and ovarian carcinomas, or viral proteins, e.g. gp120 and gp41 envelope proteins of HIV, envelope proteins from the Hepatitis B and C viruses, glycoprotein B and other envelope glycoproteins of human cytomegalovirus, and the envelope proteins from oncoviruses such as Kaposi's sarcoma-associated Herpes virus. Other potential target antigens include CD4, where the ligand is the HIV gp120 envelope glycoprotein, and other viral receptors, for example ICAM, which is the receptor for the human rhinovirus, and the related receptor molecule for poliovirus.

Human immunodeficiency virus (HIV) cannot enter human cells unless it first binds to two key molecules on the cell surface, CD4 and a co-receptor. The co-receptor that is initially recognized is CCR5, later in the life cycle of the virus another chemokine receptor CXCR4 becomes the co-receptor for HIV-1 (D'Souza, Nature Med. 2, 1293 (1996); Premack, Nature Med. 2, 1174; Fauci, Nature 384, 529 (1996)). The HIV-1 strains that cause most transmissions of viruses by sexual contact are called M-tropic viruses. These HIV-1 strains (also known as non-syncytia inducing (NSI) primary viruses) can replicate in primary CD4+ T-cells and macrophages and use the chemokine receptor CCR5 (and, less often, CCR3) as their coreceptor. The T-tropic viruses (sometimes called syncytia inducing (SI) primary viruses) can also replicate in primary CD4+ T-cells but can in addition infect established CD4+ T-cell lines in vitro, which they do via the chemokine receptor CXCR4 (fusin). Many of these T-tropic strains can use CCR5 in addition to CXCR4, and some can enter macrophages via CCR5, at least under certain in vitro conditions (D'Souza, Nature Med. 2, 1293 (1996); Premack, Nature Med. 2, 1174; Fauci, Nature 384, 529 (1996)). Because M-tropic HIV-1 strains are implicated in about 90% of sexual transmissions of HIV, CCR5 is the predominant coreceptor for the virus in patients.

The numbers and identity of coreceptor molecules on target cells, and the ability of HIV-1 strains to likely enter cells via the different coreceptors, seem to be critical determinants of disease progression. High expression of CCR3 and CCR5 was also observed in T cells and B cells of lymph nodes derived from patients with Hodgkin's disease. Diabetes type I is considered to be a T-cell mediated autoimmune disease. The expression of CCR5 receptor in the pancreas was associated with the progression of type I diabetes in relevant animal models (Cameron (2000) *J. Immunol.* 165, 1102-1110). In one embodiment, the bi-specific conditionally active antibody binds to CCR5 as the target antigen, which may be used to suppress HIV infection of host cells as well as to slow the progression of other diseases.

Several antibodies specifically binding to (human) CCR5 are known in the art and comprise MC-1 (Mack (1998) *J. Exp. Med.* 187, 1215-1224 or MC-5 (Blanpain (2002) *Mol Biol Cell.* 13:723-37, Segerer (1999) *Kidney Int.* 56:52-64, Kraft (2001) *Biol. Chem.* 14; 276:34408-18). Therefore, it is preferred that the bi-specific conditionally active antibody comprises, for example, $V_L$ and $V_H$ domains of an antibody (i.e. an Ig-derived second domain) specific for CCR5, preferably the human CCR5, and $V_H$ and $V_L$ domains of an antibody specific for the CD3 antigen on T-cells.

In another embodiment, the present invention provides for a bi-specific conditionally active antibody against CD3 on T-cells and CD19 as the target antigen. CD19 has proved to be a very useful medical target. CD19 is expressed in the whole B cell lineage from the pro B cell to the mature B cell, as well as uniformly expressed on all lymphoma cells, and is absent from stem cells (Haagen, *Clin Exp Immunol* 90 (1992), 368-75; Uckun, *Proc. Natl. Acad. Sci. USA* 85 (1988), 8603-7). Combination therapy employing both an antibody directed against CD19 and an additional immunoregulatory antibody has been disclosed for the treatment of B cell malignancies (WO 02/04021, US2002006404, US2002028178) and autoimmune diseases (WO 02/22212, US2002058029). WO 00/67795 discloses the use of antibodies against CD19 for the treatment of indolent and aggressive forms of B-cell lymphomas, as well as acute and chronic forms of lymphatic leukemias. WO 02/80987 discloses the therapeutic use of immunotoxins based on antibodies against the antigen CD19 for the treatment of such diseases as B cell non-Hodgkin's lymphoma, Hodgkin's lymphoma or B cell leukemias (e.g. B cell acute lymphatic leukemia (B-ALL), (e.g. hairy cell lymphoma) B cell precursor acute lymphatic leukemia (pre-B-ALL), B cell chronic lymphatic leukemia (B-CLL)).

In a further embodiment, the present invention provides for bi-specific conditionally active antibody against CD3 on T-cells and CD20 as the target antigen. CD20 is one of the cell surface proteins present on B-lymphocytes. CD20 antigen is found in normal and malignant pre-B and mature B lymphocytes, including those in over 90% of B-cell non-Hodgkin's lymphomas (NHL). The antigen is absent in hematopoetic stem cells, activated B lymphocytes (plasma cells) and normal tissue. Several antibodies mostly of murine origin have been described: 1F5 (Press et al., 1987, *Blood* 69/2, 584-591), 2B8/C2B8, 2H7, 1H4 (Liu et al., 1987, *J Immunol* 139, 3521-3526; Anderson et al., 1998, U.S. Pat. No. 5,736,137; Haisma et al., 1998, *Blood* 92, 184-190; Shan et al., 1999, *J. Immunol.* 162, 6589-6595).

CD20 has been described in immunotherapeutic strategies for the treatment of plasma cell malignancies using vaccination with DNA encoding scFv linked to a carrier protein (Treon et al., 2000, *Semin Oncol* 27(5), 598) and immunotherapeutic treatment using CD20 antibodies (IDEC-C2B8) have been shown to be effective in the treatment of non-Hodgkin's B-cell lymphoma.

In some embodiments, the bi-specific conditionally active antibody is a single polypeptide chain encoded by a polynucleotide molecule. The polynucleotide may be, e.g., DNA, cDNA, RNA or synthetically produced DNA or RNA or a recombinantly produced chimeric nucleic acid molecule comprising any of those polynucleotides either alone or in combination. The polynucleotide can be part of a vector, e.g., an expression vector, including plasmids, cosmids, viruses and bacteriophages, or any expression system used conventionally in genetic engineering. The vectors may comprise further genes, such as marker genes, that allow for the selection of the vector in a suitable host cell and under suitable conditions.

In one aspect, the polynucleotide is operatively linked to expression control sequences allowing expression in prokaryotic or eukaryotic cells. Expression vectors derived from viruses such as retroviruses, vaccinia virus, adenoassociated virus, herpes viruses, or bovine papilloma virus, may be used for delivery of the polynucleotides or vectors into mammalian cells. The vectors containing the polynucleotides of the invention can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Engineering Masked Conditionally Active Biologic Protein

The conditionally active biologic protein, especially the conditionally active antibody, of the present invention may have its conditional activity masked, and/or have the activity of its conjugated agent masked by a masking moiety. The masked activity will become available once the masking moiety is removed or cleaved from the conditionally active biologic protein. Suitable masking technology is described, for example, in Desnoyers et al., "Tumor-Specific Activation of an EGFR-Targeting Probody Enhances Therapeutic Index," *Sci. Transl. Med.* 5, 207ra144, 2013.

In some embodiments, the conditionally active antibody is linked with a masking moiety, which masks the conditional activity and/or the activity of its conjugated agent. For example, when the conditionally active antibody is coupled to a masking moiety, such coupling or modification can effect a structural change which reduces or inhibits the ability of the conditionally active antibody to specifically bind with its antigen. Once the conditionally active antibody reaches the target tissue or microenvironment, the masking moiety is cleaved by an enzyme present in the target tissue or the microenvironment, thus releasing the masked activity. For example, the enzyme may be a protease commonly active in the tumor microenvironment, which can cleave the masking moiety to release the conditionally active antibody with activity within a tumor tissue.

In some embodiments, the activity is masked to be less than about 50% of the original activity, or less than about 30% of the original activity, or less than about 10% of the original activity, or less than about 5% of the original activity, or less than about 2% of the original activity, or less than about 1% of the original activity, or less than about 0.1% of the original activity, or less than about 0.01% of the original activity. In some embodiments, for example, in order to ensure adequate time for delivery, the masking effect is designed to last for at least 2, 4, 6, 8, 12, 28, 24, 30, 36, 48, 60, 72, 84, 96 hours, or 5, 10, 15, 30, 45, 60, 90, 120, 150, 180 days, or 1, 2, 3, 4, 5, 6, 7, 8, 9, 10, 11, 12 months or greater when measured in vivo or in a target displacement in vitro immunoabsorbent assay.

In certain embodiments, the masking moiety is structurally similar to the natural binding partner (antigen) of the conditionally active antibody. The masking moiety may be a modified natural binding partner of the conditionally active antibody, which contains amino acid changes that at least slightly decrease the affinity and/or avidity of binding to the conditionally active antibody. In some embodiments the masking moiety contains no or substantially no homology to the conditionally active antibody's In other embodiments the masking moiety has a sequence identify of no more than 5%, 10%, 15%, 20%, 25%, 30%, 35%, 40%, 45%, 50%, 55%, 60%, 65%, 70%, 75%, or 80% to the natural binding partner of the conditionally active antibody.

The masking moiety can be provided in a variety of different forms. In certain embodiments, the masking moiety can be a known binding partner of the conditionally active antibody, provided that the masking moiety binds to the conditionally active antibody with less affinity and/or avidity than the target protein to which the conditionally active antibody is targeted following cleavage of the masking moiety so as to reduce interference of the masking moiety with the desired binding to the target. Thus, the masking moiety is preferably one that masks the conditionally active antibody from target binding before the masking moiety is cleaved, but does not substantially or significantly interfere with or compete for binding of the active molecule to the target when after the masking moiety has been cleaved from the antibody. In a specific embodiment, the conditionally active antibody and masking moiety do not contain the amino acid sequences of a naturally-occurring binding partner pair, such that at least one of the conditionally active antibody and masking moiety does not have the amino acid sequence of a member of a naturally occurring binding partner.

Alternatively, the masking moiety may not specifically bind to the conditionally active antibody, but rather interfere with conditionally active antibody-target binding through non-specific interactions such as steric hindrance. For example, the masking moiety may be positioned such that the structure or conformation of the antibody allows the masking moiety to mask the conditionally active antibody through, for example, a charge-based interaction, thereby interfering with target access to the conditionally active antibody.

In some embodiments, the masking moiety is coupled to the conditionally active antibody by covalent binding. In another embodiment, the conditionally active antibody is prevented from binding to its target by binding the masking moiety to an N-terminus of the conditionally active antibody. In yet another embodiment, the conditionally active antibody is coupled to the masking moiety by cysteine-cysteine disulfide bridges between the masking moiety and the conditionally active antibody.

In some embodiments, the conditionally active antibody is further coupled to a cleavable moiety (CM). The CM is capable of being cleaved by an enzyme, or the CM is capable of being reduced by a reducing agent, or the CM is capable of being photo lysed. In one embodiment, the amino acid sequence of the CM may overlap with or be included within the masking moiety. In another embodiment, the CM is between the conditionally active antibody and the masking moiety. It should be noted that all or a portion of the CM may facilitate masking of the conditionally active antibody before cleavage. When the CM is cleaved the conditionally active antibody becomes more active in binding to its antigen.

The CM may be a substrate for an enzyme that is co-localized with the target antigen at a treatment site in a subject. Alternatively, or in addition, the CM may have a cysteine-cysteine disulfide bond that is cleavable as a result of reduction of this disulfide bond. The CM may also be a photolabile substrate, activatable by a light source.

The enzymes that cleave the CM should be preferentially located in a desired target tissue of the conditionally active antibody where the conditionally active antibody is more active at the condition presented in the target tissue (aberrant condition), such as diseased tissue or tumor tissue. For example, there are known proteases with increased level in a number of cancers, e.g., solid tumors. See, e.g., La Rocca et al, (2004) *British J. of Cancer* 90(7): 1414-1421. Non-liming examples of such diseases include: all types of cancers (breast, lung, colorectal, prostate, head and neck, pancreatic, etc), rheumatoid arthritis, Crohn's disease, melanomas, SLE, cardiovascular damage, ischemia, etc. As such, a suitable CM may be selected which comprises a peptide substrate that is cleavable by a protease that is present in tumor tissue, particularly that is present at elevated levels in the tumor tissue as compared to non-cancerous tissues.

In some embodiments, the CM may be a substrate for an enzyme selected from legumain, plasmin, TMPRSS-3/4, MMP-9, MT1-MMP, cathepsin, caspase, human neutrophil elastase, beta-secretase, uPA and PSA. The enzyme that cleaves the CM is present at relatively higher levels in target tissue of a treatment site (for example diseased tissue or tumor tissue; for example for therapeutic treatment or diagnostic treatment) than in tissue of non-treatment sites (for example in healthy tissue). Therefore, besides the conditional activity of the antibody, which may be more active at the diseased tissue or tumor tissue, the enzyme presented at the diseased tissue or tumor tissue can cleave the CM, which further enhances the activity of the conditionally active antibody, or the activity of a conjugated agent. The unmodified or uncleaved CM can allow for efficient inhibition or masking of the activity of the conditionally active antibody, such that the conditionally active antibody is less active at normal tissue (normal physiological condition). The dual mechanism of suppressing the activity of conditionally active antibody at normal tissue (conditional activity and masking moiety) allows use of a much high dosage of the conditionally active antibody to be used without causing significant adverse effects.

In some embodiments, the CM may be a substrate of an enzyme selected from the enzymers listed in Table 1 below.

TABLE 1

Exemplary Enzymes/Proteases

| | | | |
|---|---|---|---|
| ADAM10 | Caspase 8 | Cathepsin S | MMP 8 |
| ADAM12 | Caspase 9 | FAP | MMP 9 |
| ADAM17 | Caspase 10 | Granzyme B | MMP-13 |
| ADAMTS | Caspase 11 | Guanidinobenzoatase (GB) | MMP 14 |
| ADAMTS5 | Caspase 12 | Hepsin | MT-SP1 |
| BACE | Caspase 13 | Human Neutrophil Elastase (HNE) | Neprilysin |
| Caspases | Caspase 14 | Legumain | NS3/4A |
| Caspase 1 | Cathepsins | Matriptase 2 | Plasmin |
| Caspase 2 | Cathepsin A | Meprin | PSA |
| Caspase 3 | Cathepsin B | MMP 1 | PSMA |
| Caspase 4 | Cathepsin D | MMP 2 | TACE |
| Caspase 5 | Cathepsin E | MMP 3 | TMPRSS 3/4 |
| Caspase 6 | Cathepsin K | MMP 7 | uPA |
| Caspase 7 | MT1-MMP | | |

Alternatively or in addition, the CM can include a disulfide bond of a cysteine pair, which is thus cleavable by a reducing agent such as a cellular reducing agent including glutathione (GSH), thioredoxins, NADPH, flavins, ascorbate, and the like, which can be present in large amounts in tissue of, or surrounding, a solid tumor.

In some embodiments, the conditionally active antibody contains both CM and a masking moiety. The activity of the conditionally active antibody is unmasked upon cleavage of the CM by an enzyme. In some embodiments, it may be desirable to insert one or more linkers, e.g., flexible linkers, between the antibody, the masking moiety and the CM, so as to provide for flexibility. For example, the masking moiety and/or CM may not contain a sufficient number of residues (e.g., Gly, Ser, Asp, Asn, especially Gly and Ser, particularly Gly) to provide the desired flexibility. As such, it may be beneficial to introduce one or more amino acids to provide for a flexible linker. For example, the masked conditionally active antibody may have the following structures (where the formula below represent an amino acid sequence in either N- to C-terminal direction or C- to N-terminal direction):

(MM)-$L_1$-(CM)-(AB)

(MM)-(CM)-$L_1$-(AB)

(MM)-$L_1$-(CM)-$L_2$-(AB)

Cyclo[$L_1$-(MM)-$L_2$-(CM)-$L_3$-(AB)]

wherein MM is the masking moiety and AB is the conditionally active antibody; $L_1$, $L_2$, and $L_3$ represent each independently and optionally present or absent, being the same or different flexible linkers that include at least one flexible amino acid (e.g., Gly); and cyclo where present, the entire structure is in the form of a cyclic structure due to the presence of a disulfide bond between a pair of cysteines at or near both N- and C-terminus of the structure.

Linkers suitable for use in the invention are generally ones that provide flexibility to the masking moiety to facilitate the inhibition of the activity of the conditionally active antibody. Such linkers are generally referred to as flexible linkers. Suitable linkers can be readily selected and can be of any of suitable different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $(GSGGS)_n$, SEQ ID NO:1 and $(GGGS)_n$, SEQ ID NO:2, where n is an integer of at least one, glycine-alanine polymers, alanine-serine polymers, and other flexible linkers known in the art. Exemplary flexible linkers include, but are not limited to Gly-Gly-Ser-Gly (SEQ ID NO:3), Gly-Gly-Ser-Gly-Gly (SEQ ID NO:4), Gly-Ser-Gly-Ser-Gly (SEQ ID NO:5), Gly-Ser-Gly-Gly-Gly (SEQ ID NO:6), Gly-Gly-Gly-Ser-Gly (SEQ ID NO:7), Gly-Ser-Ser-Ser-Gly (SEQ ID NO:8), and the like.

Some of the techniques used for masking the activity of the conditionally active antibody is described in WO2010081173A2.

Pharmaceutical Compositions

The present disclosure provides at least one composition comprising (a) a conditionally active biologic protein; and (b) a suitable carrier or diluent. The present disclosure also provides at least one composition comprising (a) a conditionally active biologic protein encoding nucleic acid as described herein; and (b) a suitable carrier or diluent. The carrier or diluent can optionally be pharmaceutically acceptable, according to known carriers or diluents. The composition can optionally further comprise at least one further compound, protein or composition. In some embodiments, the conditionally active biologic protein is a conditionally active antibody.

The conditionally active biologic protein may be in the form of a pharmaceutically acceptable salt. Pharmaceutically acceptable salts means which can be generally used as salts of an therapeutic protein in pharmaceutical industry, including for example, salts of sodium, potassium, calcium and the like, and amine salts of procaine, dibenzylamine, ethylenediamine, ethanolamine, methylglucamine, taurine, and the like, as well as acid addition salts such as hydrochlorides, and basic amino acids and the like.

The present disclosure further provides at least one conditionally active biologic protein method or composition, for administering a therapeutically effective amount to modulate or treat at least one parent molecule related condition in a cell, tissue, organ, animal or patient and/or, prior to, subsequent to, or during a related condition, as known in the art and/or as described herein. Thus, the disclosure provides a method for diagnosing or treating a condition associated with the wild-type protein in a cell, tissue, organ or animal, comprising contacting or administering a composition comprising an effective amount of at least one conditionally active biologic protein of the disclosure with, or to, the cell, tissue, organ or animal. The method can optionally further comprise using an effective amount of 0.001-50 mg/kilogram of a conditionally active biologic protein of the disclosure to the cells, tissue, organ or animal. The method can optionally further comprise using the contacting or the administrating by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal. The method can optionally further comprise administering, prior, concurrently, or after the conditionally active biologic protein contacting or administering at least one composition comprising an effective amount of at least one compound or protein selected from at least one of a detectable label or reporter, a TNF antagonist, an antirheumatic, a muscle relaxant, a narcotic, a non-steroid anti-inflammatory drug (NSAK)), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog thereof, a cytotoxic or other anti-cancer agent, an anti-metabolite such as methotrexate, or an antiproliferative agent.

The present disclosure further provides at least one conditionally active biologic protein method for diagnosing at least one wild-type protein related condition in a cell, tissue, organ, animal or patient and/or, prior to, subsequent to, or during a related condition, as known in the art and/or as described herein.

Pharmaceutically acceptable carriers are determined in part by the particular composition being administered, as well as by the particular method used to administer the composition. Accordingly, there is a wide variety of suitable formulations of pharmaceutical compositions of the present invention. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of conditionally active biologic protein in these formulations can vary widely, and will be selected primarily based on fluid volumes, viscosities, body weight and the like in accordance with the particular mode of administration selected and the patient's needs.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Pharmaceutical compositions and formulations of the invention for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropyhnethyl cellulose, or sodium carboxymethylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscannellose sodium, talc, magnesium stearate, stearic acid, and other excipients, colorants, fillers, binders, diluents, buffering agents, moistening agents, preservatives, flavoring agents, dyes, disintegrating agents, and pharmaceutically acceptable carriers.

The invention provides aqueous suspensions comprising a conditionally active biologic protein, in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolality.

Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art. It is recognized that the conditionally active biologic protein, when administered orally, must be protected from digestion. This is typically accomplished either by complexing the conditionally active biologic protein with a composition to render it resistant to acidic and enzymatic hydrolysis or by packaging the conditionally active biologic protein in an appropriately resistant carrier such as a liposome. Means of protecting proteins from digestion are well known in the art. The pharmaceutical compositions can be encapsulated, e.g., in liposomes, or in a formulation that provides for slow release of the active ingredient.

The packaged conditionally active biologic protein, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like. Suitable formulations for rectal administration include, for example, suppositories, which consist of the packaged nucleic acid with a suppository base. Suitable suppository bases include natural or synthetic triglycerides or paraffin hydrocarbons, in addition, it is also possible to use gelatin rectal capsules which consist of a combination of the packaged nucleic acid with a base, including, for example, liquid triglycerides, polyethylene glycols, and paraffin hydrocarbons.

Dermal or topical delivery compositions of the invention may include in addition to a conditionally active biologic protein, a pharmaceutically acceptable carrier in a cream, ointment, solution or hydrogel formulation, and other compounds so long as the added component does not deleteriously affect delivery of the therapeutic protein. Conventional pharmaceutically acceptable emulsifiers, surfactants, suspending agents, antioxidants, osmotic enhancers, extenders, diluents and preservatives may also be added. Water soluble polymers can also be used as carriers.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives, in the practice of this invention, compositions can be administered, for example, by intravenous infusion, orally, topically, intraperitoneally, intravesically or intrathecally. In one aspect, parenteral modes of administration are preferred methods of administration for compositions comprising a conditionally active biologic protein. The compositions may conveniently be administered in unit dosage form and may be prepared by any of the methods well-known in the pharmaceutical art, for example as described in Remington's Pharmaceutical Sciences, Mack Publishing Co. Easton Pa., $18^{th}$ Ed., 1990. Formulations for intravenous administration may contain a pharmaceutically acceptable carrier such as sterile water or saline, polyalkylene glycols such as polyethylene glycol, oils of vegetable origin, hydrogenated naphthalenes and the like. Also see and adapt the description in U.S. Pat. No. 4,318,905.

The formulations of packaged compositions comprising a conditionally active biologic protein can be presented in unit-dose or multi-dose sealed containers, such as ampoules and vials. Injection solutions and suspensions can be prepared from sterile powders, granules, and tablets of the kind previously described.

The present disclosure also provides at least one conditionally active biologic protein composition, device and/or method of delivery for diagnosing of at least one wild-type protein related condition, according to the present disclosure.

Also provided is a composition comprising at least one conditionally active biologic protein and at least one pharmaceutically acceptable carrier or diluent. The composition can optionally further comprise an effective amount of at least one compound or protein selected from at least one of a detectable label or reporter, a cytotoxic or other anti-cancer agent, an anti-metabolite such as methotrexate, an antiproliferative agent, a cytokine, or a cytokine antagonist, a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog.

Also provided is a medical device, comprising at least one conditionally active biologic protein of the disclosure, wherein the device is suitable to contacting or administering the at least one conditionally active biologic protein by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal.

In a further aspect, the disclosure provides a kit comprising at least one conditionally active biologic protein or fragment of the disclosure in lyophilized form in a first container, and an optional second container comprising sterile water, sterile buffered water, or at least one preservative selected from the group consisting of phenol, m-cresol, p-cresol, o-cresol, chlorocresol, benzyl alcohol, phenylmercuric nitrite, phenoxyethanol, formaldehyde, chlorobutanol, magnesium chloride, alkylparaben, benzalkonium chloride, benzethonium chloride, sodium dehydroacetate and thimerosal, or mixtures thereof in an aqueous diluent. In one aspect, in the kit, the concentration of conditionally active biologic protein or specified portion or variant in the first container is reconstituted to a concentration of about 0.1 mg/ml to about 500 mg/ml with the contents of the second container, in another aspect, the second container further comprises an isotonicity agent. In another aspect, the second container further comprises a physiologically acceptable buffer. In one aspect, the disclosure provides a method of treating at least one wild-type protein mediated condition, comprising administering to a patient in need thereof a formulation provided in a kit and reconstituted prior to administration.

Also provided is an article of manufacture for human pharmaceutical or diagnostic use comprising packaging material and a container comprising a solution or a lyophilized form of at least one conditionally active biologic protein of the present disclosure. The article of manufacture can optionally comprise having the container as a component of a parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal delivery device or system.

The present disclosure further provides any disclosure described herein.

Example 1: General Description of a Multiwall Assay (for Example, 96-Well Assay) for Temperature Mutants Fluorescent substrate is added to each well of a multiwall plate, at both wild-type and new, lower reaction temperatures (for example, either 37° C. or 25° C. as mentioned above) for an appropriate time period. Fluorescence is detected by measuring fluorescence in a fluorescent plate reader at appropriate excitation and emission spectra (for example, 320 nm excitation/405 nm emission). Relative fluorescence units (RFU) are determined. Supernatant from wild type molecule and plasmid/vector transformed cells are used as positive and negative controls. Duplicate reactions are performed for each sample, reaction temperature, and positive and negative control.

Mutants that are active at the lower temperature (for example, the mutants active at 25° C.) and that have a decrease in activity at the wild type temperature (for example, a 10%, 20%, 30%, 40% or more decrease in activity at 37° C.), thus having a ratio of activities greater than or equal to about 1.1 or more (e.g., the ratio of the activities at 25° C. or 37° C. (25° C./37° C.) is greater than or equal to 1.1 or more), can be deemed to be putative primary temperature sensitive hits. These putative primary temperature sensitive hits can then be rescreened, using the same assay, to confirm any primary hits.

Example 2: General Description of a Different Assay Format for Confirmation of Activity (for Example, a 14-mL Assay) for Temperature Mutants Mutants that are identified as temperature sensitive primary hits are expressed in 14 ml culture tubes and their enzymatic activity is measured at wild type (for example, 37° C.) and the lower temperature (for example, 25° C.). Protein is expressed and purified as described above for the multiwall format, with the exception that the expression is performed in different format (14 ml tubes) rather than the multiwall (96-well plate) format.

Each mutant supernatant is transferred to a multiwall plate, for example a 96-well microplate. Fluorescent substrate is added to each tube at the indicated reaction temperatures (wild-type, lower temperature) for a required period of time. Wild-type molecules are used as a positive control and supernatant from cells transformed with only vector is used as a negative control. Fluorescence is detected by measuring fluorescence in a fluorescent plate reader at the appropriate emission spectra (for example, 320 nm excitation/405 ran emission). Relative fluorescence units (RFU) are determined. Duplicate reactions can are performed for each sample, reaction temperature, and positive and negative control.

Mutants that are active at the lower temperatures (for example, 25° C.) but that demonstrate at least a 30% or more decreased activity at wild type (for example, 37° C.), thus have a ratio of activity at lower temperature (for example, 25° C.) to wild type temperature (for example, 37° C.) equal to or greater than 1.5, are identified as temperature sensitive hits.

The activities of mutants at the lower temperature (for example 25° C.) are compared to the activity of the wild-type molecule at the wild-type temperature (for example 37° C.). If molecules are more active than the wild-type molecules at the lower temperature (for example 25° C.), as indicated by a residual activity >1, preferably 2 or greater than 2, and if the mutants demonstrate an overall decrease in activity when compared to the wild-type molecule at the wild-type temperature (37° C.), the phenotype of the mutants as temperature sensitive mutants can be confirmed.

Example 3: General Description of Further Evolution of Hits Discovered

If desired, a new, combinatorial variant library is generated from all or selected mutant hits previously identified. The new library can be designed to contain every possible combination of amino acid variants for each of the selected mutants, and rescreened as described for new hits.

Example 4: General Description of Reversibility of Enzymatic Activity Following Decrease in Temperature Temperature sensitive, evolved mutants can be further assayed to determine whether enzymatic activity at lower temperatures (for example, 25° C.) is reversible or irreversible by exposing the mutants to elevated temperatures followed by a return to the lower temperature (for example, 25° C.). The temperature sensitive mutants are expressed in any desired format, for example in 14 ml culture tubes, as briefly described. The mutants are tested for their activities under several conditions, including the wild-type temperature (for example, 37° C.) as well as other temperatures, and subsequently re-exposure to the requisite lower temperature of (25° C. for example). Mutants that are active at lower temperatures, show decreased activity when raised to higher or wild-type temperatures (i.e., the ratio of the activities at lower to higher temperatures is equal to or greater than 1, 1.5, or 2 or higher), and exhibit a baseline activity when lowered again to the lower temperature are scored as "Reversible Hits". Mutants that are active at the lower temperature, show decreased activity when raised to higher or wild-type temperatures (i.e., the ratio of the activities at the lower to higher temperatures is equal to or greater than 1, 1.5 or 2 or higher), and exhibit at least the same amount of decreased activity when lowered again to the lower temperature are scored as "Irreversible Hits".

Example 5: Materials and Methods to Screen for Conditionally Active Angiostatin Variants Materials and methods to screen for conditionally active angiostatin variants can be adapted from Chi and Pizzo, "Angiosatin is directly cytotoxic to tumor cells at low extracellular pH: a mechanism dependent on cell surface-associated ATP synthase", *Cancer Res.* 2006; 66(2):875-882.

Materials. Wild-type angiostatin kringles 1 to 3, derived from human plasminogen, can be obtained from Calbiochem (Darmstadt, Germany) and reconstituted in sterile PBS. Polyclonal antibodies directed against the catalytic beta-subunit of ATP synthase can be generated and bovine F1 ATP synthase subunit can be purified as previously described (Moser et al., "Angiostatin binds ATP synthase on the surface of human endothelial cells", *Proc Natl Acad Sci USA* 1999; 96:2811-6; Moser et al. "Endothelial cell surface F1-FO ATP synthase is active in ATP synthesis and is inhibited by angiostatin", *Proc Natl Acad Sci USA;* 2001; 98:6656-61). Cariporide can be solubilized in sterile water and sterile filtered.

Cell culture. A549 (human epithelial cell line derived from a lung carcinoma tissue), or an alternative cancer cell line (DU145, LNCaP, or PC-3 cells) can be obtained from, for example, the ATCC. Human umbilical vein endothelial cells (HUVEC) can be isolated from human umbilical veins as described. (Grant et al., "Matrigel induces thymosin h 4 gene in differentiating endothelial cells", *J Cell Sci* 1995; 108:3685-94). HUVEC cells can be used as a positive control as a cell line that express ATP synthase on the cell surface. Cells can be cultured in DMEM (Life Technologies, Carlsbad, Calif.) with 1% penicillin streptomycin and 10% serum replacement medium 3 (Sigma, St. Louis, Mo.) to minimize the presence of plasminogen. Low-pH (6.7) medium can be prepared by reducing bicarbonate to 10 mmol/L at 5% $CO_2$ and supplementing with 34 mmol/L NaCl to maintain osmolality or incubation of 22 mmol/L bicarbonate medium under 17% $CO_2$ conditions. The method of lowering pH used can be varied by experimental constraints and assay.

Flow cytometry. To assure ATP synthase is functional on the cell surface of the tumor cell line, flow cytometry experiments can be performed. For example, A549 Cell lines can be cultured in varying pH medium (10, 22, and 44 mmol/L bicarbonate DMEM), under hypoxia (0.5% $O_2$, 5% $CO_2$, $N_2$ balanced) versus normoxia (21% $O_2$, 5% $CO_2$) for 0, 12, 24, 48, and 72 hours. Live cells can be blocked, incubated with anti-β-subunit antibody, washed, blocked, incubated with a secondary goat anti-rabbit antibody-FITC (Southern Biotech, Birmingham, Ala.), and again washed, with all steps performed at 4 degrees C. Propidium iodide (BD Biosciences, San Jose, Calif.) can be included with all samples to discriminate cells with compromised membranes. The mean fluorescent intensity of FITC in 10,000 cells can be quantified by FACSCalibur flow cytometer (Becton Dickinson, Franklin Lakes, N.J.) and cells with propidium iodide uptake can be excluded to eliminate detection of mitochondrial ATP synthase on CELLQuest software (BD Biosciences).

Cell surface ATP generation assay. A549 or 1-LN cells (60,000 per well) in 96-well plates can be refreshed with medium and treated with angiostatin, angiosatain variant, anti-beta-subunit antibody, rabbit IgG raised to bovine serum albumin (Organon Teknika, West Chester, Pa.), piceatannol (a known inhibitor of ATP synthase F1 used as a positive control, Sigma), or medium alone for 30 minutes at 37 degrees C., 5% $CO_2$. Cells can be then incubated with 0.05 mmol/L ADP for 20 seconds. Supernatants can be removed and assayed for ATP production by CellTiterGlo luminescence assay (Promega, Madison, Wis.) as described (23). Cell lysates can be similarly analyzed to confirm that intracellular pools of ATP did not vary under any conditions. Recordings can be made on the Luminoskan Ascent (Thermo Labsystems, Helsinki, Finland). Data are expressed in moles of ATP per cell based on standards determined for each independent experiment.

Cell proliferation assay. The effect of angiostatin on cancer cell lines can be assessed with a 3-(4,5-dimethylthiazol-2-yl)-5-(3-carboxymethoxyphenyl)-2-(4-sulfophenyl)-2H-tetrazolium, inner salt (MTS) proliferation assay in serum-free medium. Relative cell numbers in each well of a 96-well microplate after incubation for 20 hours, 37 degrees C., and 5% $CO_2$ in the presence or absence of angiostatin can be determined using the AQueous One Cell Proliferation Assay (Promega) per protocol of the manufacturer. Medium pH can be regulated at 5% $CO_2$ through bicarbonate concentration.

Assessment of cellular cytotoxicity. To quantify cell death and cell lysis, the activity of lactate dehydrogenase (LDH) released from the cytosol into supernatant can be measured with the Cytotoxicity Detection kit (Roche, Indianapolis, Ind.). Cancer cells (e.g. A549 cells) (5,000 per well) treated with angiostatin, angiostatin variant, anti-beta-subunit antibody, rabbit IgG, cariporide, and Triton X (a detergent used to permeabilize cells as a positive control) can be incubated at 37 degrees C. and 5% $CO_2$ or 17% $CO_2$ for 15 hours at neutral and low pH conditions, respectively. An index of cytotoxicity can be calculated by dividing the average absorbance from treated samples in quadruplicate by the average absorbance from untreated samples in quadruplicate corresponding to the same pH medium. Assessment of cellular necrosis and apoptosis. To determine the mode of angiostatin induced cell death a histone-DNA ELISA can be performed. The effects of angiostatin, angiostatin variants, anti-beta-subunit antibody, rabbit IgG, and cariporide on A549 cells (5,000 per well) can be determined using an ELISA apoptosis and necrosis assay (Roche) that is dependent on detection of extranuclear histone-DNA fragments. Apoptosis or necrosis can be determined from, respectively, the cell lysates or supernatants of quadruplicate samples after 15 hours of incubation at 37 degrees C., in the presence or absence of agents. The apoptotic or necrotic indices can be calculated by dividing the average absorbance from treated samples in quadruplicate by the average absorbance from untreated samples in quadruplicate corresponding to the same pH medium. Medium pH can be regulated by incubation at 5% $CO_2$ or 17% $CO_2$.

Intracellular pH (pHi) measurement. pHi can be measured by fluorescence in cells plated on 35-mm microwell dishes with glass coverslips (MatTek, Ashland, Mass.). Cells can be plated on growth factor-reduced, phenol-red free Matrigel (BD Biosciences). After overnight growth, medium can be changed and cells can be loaded with the pH-sensitive fluorescent dye cSNARF (Molecular Probes, Eugene, Oreg.) for 15 minutes followed by 20 minutes recovery in fresh medium. Cells can then be mounted on a microscope stage at 37 degrees C., 5% $CO_2$ for 1 hour-long collection of emission spectra from which pHi can be calculated as described from fields containing between 7 and 15 cells each (Wahl M L, Grant D S. "Effects of microenvironmental extracellular pH and extracellular matrix proteins on angiostatin's activity and on intracellular pH", *Gen Pharmacol* 2002; 35:277-85). At the start of spectra collection, medium can be removed from the dish and cells can be challenged with 1 mL of fresh medium in the presence or absence of pH inhibitors angiostatin, anti-beta-subunit, rabbit IgG, or cariporide, a sodium-proton exchange inhibitor. Medium pH can be regulated by bicarbonate concentration, as described above, with fixed % $CO_2$.

Example 6: Evolving a Light Chain or a Heavy Chain of an Antibody

The heavy chain and light chain of an antibody F1-10F10 were separately evolved using CPE. The light chain mutants were screened to discover 26 light chain mutants with conditional activity, in this case the mutants were more active at pH 6.0 than the wild-type and the mutants less active at pH 7.4 than the wild-type. The 26 light chain mutants had their mutations at 8 different positions in the light chain. 3 of the 8 positions appeared in more than 5 of the 26 light chain mutants. These 3 positions were deemed to be hot spots in the light chain. The heavy chain mutants were screened to discover 28 heavy chain mutants with conditional activity. The 28 heavy chain mutants had their mutations at 8 different positions in the heavy chain. 3 of the 8 positions appeared in more than 5 of the 28 heavy chain mutants. These 3 positions were deemed to be hot spots in the heavy chain. The conditional activity of the light chain mutants and heavy chain mutants was confirmed by an ELISA assay.

The best conditionally active antibody generated by this example had a 17-fold difference in its activity at pH 6.0 to its activity at pH 7.4. In addition, many of the conditionally active antibodies had an activity that was reversible at a pH between the normal physiologic pH of 7.4 and the aberrant pH of 6.0. Interestingly, most of the conditionally active antibodies generated from this example exhibited optimal binding activity at a pH of about 5.5 to 6.5, when the activity of the conditionally active antibodies was tested in the pH range of 5.0 to 7.4 by the ELISA assay.

The activity of the conditionally active antibodies generated by this example was also confirmed by a FACS (Fluorescence-activated cell sorting) assay using whole cells, where CHO cells were used to express the antigen of the antibodies at pH 6.0 and pH 7.4. The conditionally active antibodies were added to CHO cells in order to measure the binding activity. The FACS assay confirmed the general trend in the results of the ELISA assay for the selectivity of the conditionally active antibodies at pH 6.0 relative to pH 7.4.

Example 7: Selecting Conditionally Active Antibodies in a Special Buffer

Mutant antibodies generated by an evolving step in accordance with the present invention were subjected to an assay at a normal physiologic pH of 7.4 and to an assay at an aberrant pH of 6.0. Both assays were performed using a phosphate buffered saline (PBS) solution including a bicarbonate found in human serum. The concentration of Bicarbonate in the solution was a typical concentration of Bicarbonate in a human serum, i.e. a physiological concentration. A comparative test was done using the same PBS solution without bicarbonate.

The assay for measuring the binding activity for the mutant antibodies or conditionally active antibodies in this example was an ELISA assay, which was carried out as follows:
1. The pre-day of ELISA: the wells were coated with 100 ul of antibody Ab-A ECD his tag (2.08 mg/ml) antigen at 1 ug/ml with PBS, 3. The buffer solution was flicked off from the 96 well plate coated with Antibody Ab-A-His antigen, and blotted dry on paper towels.

4. The plates were washed 3× with buffer N or PBS,

5. The plates were blocked with 200 ul of designated buffer at room temperature for 1 hour, 6. The selected CPE/CPS mutants and the wild type protein were diluted to 75 ng/ml in designated buffer solutions according to the layout. The pH of the buffer solution was set to either 6.0 or 7.4 (hereinafter "the designated buffer solution"), 6. The buffer was flicked off and 100 ul of 75 ng/ml sample was added to each well according to the plate layout, 7. The plates were incubated at room temperature for 1 hour, 8. The buffer was flicked off from the 96 well plate, and blotted dry on paper towels, 9. The plate was washed with 200 ul of the designated buffer solution for a total of 3 times according to the layout, 10. Anti-Flag HRP was prepared in the designated buffer solution at a 1:5000 dilution and 100 ul of the Anti-Flag horseradish peroxide (HRP) was added to each well according to the layout, 11. The plate was incubated at room temperature for 1 hour, 13. The plate was washed with 200 ul of the designated buffer solution a total of 3 times, 14. The plate was developed with 50 ul of 3,3', 5,5-tetramethylbenzidine (TMB) for 1.5 min.

It was found that the assays in the PBS buffer solution containing bicarbonate resulted in a significantly higher success rate for the selection of conditionally active antibodies. In addition, the conditionally active antibodies selected using the PBS buffer solution containing bicarbonate tended to have much higher ratio of their activity at pH 6.0 to the activity at pH 7.4 thereby providing a significantly higher selectivity.

It was further observed that when the selected conditionally active antibodies (using PBS buffer solution with bicarbonate were tested in the PBS buffer solution without bicarbonate, the selectivity of the conditionally active antibodies at pH 6.0 relative to pH 7.0 was significantly reduced. However, when bicarbonate was added to this PBS buffer solution in a physiological amount, the selectivity of the same conditionally active antibodies was restored.

In another assay, the selected conditionally active antibodies were tested in a Krebs buffer solution with added bicarbonate. The higher ratio of the activity at pH 6.0 to the activity at pH 7.4 was also observed in this Krebs buffer solution with added bicarbonate. It appears that this may have been at least partly due to the presence of bicarbonate in the Krebs buffer solution.

When the concentration of bicarbonate was reduced in the PBS buffer solution to concentrations below its physiological concentration, it was observed that the activity of the conditionally active antibody at the normal physiological pH of 7.4 was increased. The increase in the activity of the conditionally active antibody at pH 7.4 was observed to be related to the decrease in the concentration of bicarbonate in the PBS buffer solution.

The wild-type antibody was not affected by the different amounts of bicarbonate in the PBS buffer solution when assayed at pH 7.4 as its activity remained the same at all the same concentrations of bicarbonate in the PBS buffer solution that were tested for the conditionally active antibody.

Example 8: Selecting Conditionally Active Antibodies in Different Buffers

The mutant antibodies generated by an evolving step according to the present invention were subjected to an ELISA assay at a normal physiologic pH (7.4) and an ELISA assay at an aberrant pH (6.0). Both ELISA assays were performed using different buffers, including buffers based on Krebs buffer with bovine serum albumin (BSA), and buffers based on PBS buffer with bicarbonate and BSA.

The ELISA assay was carried out as follows:

1. The pre-day of ELISA: wells were coated with 100 ul of Antibody Ab-A ECD his tag (2.08 mg/ml) antigen at 1 ug/ml with coating buffer (Carbonate-Bicarbonate buffer).

2. The buffer solution was flicked off from the 96 well plate coated with Antibody Ab-A-His antigen, and blotted dry on paper towels.

3. The plates were washed 3× with 200 ul of 20 buffers.

4. The plates were blocked with 200 ul of 20 buffers at room temperature for 1 hour.

5. The mutants and chimera were diluted to 75 ng/ml in 20 buffers according to the layout.

6. The buffer was flicked off and 100 ul of diluted sample was added to each well according to the plate layout.

7. The plates were incubated at room temperature for 1 hour.

8. The buffer from the 96 well plate was flicked off, and the plate was blotted dry using paper towels.

9. The plates were washed with 200 ul of 20 buffers a total of 3 times.

10. An anti-flag IgG HRP was prepared in 20 buffers at 1:5000 dilution. 100 p1 of the anti-flag IgG HRP solution was added to each well.

11. The plates were incubated at room temperature for 1 hour.

12. The plates were washed with 200 ul of 20 buffers a total of 3 times.

13. The plates were developed with 50 ul 3,3', 5,5-tetramethylbenzidine for 30 seconds.

The conditionally active antibodies selected using assays in the PBS buffer solution with bicarbonate exhibited a much higher ratio of the activity at pH 6.0 to the activity at pH 7.4, in comparison with those selected using an assay in PBS buffer solution without bicarbonate. In addition, the Krebs buffer solution with added bicarbonate also provided a higher ratio of the activity at pH 6.0 to the activity at pH 7.4 when comparison with the assay in PBS buffer solution without bicarbonate. It appears the bicarbonate is important to the selection of desirable conditionally active antibodies.

Example 9: Selecting Conditionally Active Antibodies in Different Buffers

Conditionally active antibodies to an antigen that are more active at pH 6.0 than the wild type antibody and less active at pH 7.4 than the wild type antibody were screened in this example. The screening steps were conducted using the buffers in Tables 2 and 3 below. The buffers in Table 2 were based on Krebs buffer, with additional components added as shown in column 1 of Table 2.

TABLE 2

Krebs Buffer Based Assay Buffers

| Additional components in | Buffer 1 | | Buffer 2 | | Buffer 3 | | Buffer 4 | | Buffer 5 |
|---|---|---|---|---|---|---|---|---|---|
| pH of the buffers | pH 6.0 | pH 7.4 | pH 6.0 | pH 7.4 | pH 6.0 | pH 7.4 | pH 6.0 | pH 7.4 | pH 6.0 |
| D-Glucose | 0 | 0 | 1.8 | 1.8 | 1.8 | 1.8 | 1.8 | 1.8 | 1.8 |
| Magnesium Chloride | 0.0468 | 0.468 | 0 | 0 | 0.0468 | 0.0468 | 0.0468 | 0.0468 | 0.0468 |
| Potassium Chloride | 0.34 | 0.34 | 0.34 | 0.34 | 0 | 0 | 0.34 | 0.34 | 0.34 |
| Sodium Chloride | 7 | 7 | 7 | 7 | 7 | 7 | 7 | 7 | 7 |
| Sodium Phosphate Dibasic | 0.1 | 0.1 | 0.1 | 0.1 | 0.1 | 0.1 | 0.1 | 0.1 | 0 |
| Sodium Phosphate Monobasic | 0.18 | 0.18 | 0.18 | 0.18 | 0.18 | 0.18 | 0.18 | 0.18 | 0.18 |
| Sodium Bicarbonate | 1.26 | 1.26 | 1.26 | 1.26 | 1.26 | 1.26 | 1.26 | 1.26 | 1.26 |
| Lactic acid | 16 mM | 1 mM | 16 mM | 1 mM | 16 mM | 1 mM | 16 mM | 1 mM | 16 mM |
| 85A | 10 | 10 | 10 | 10 | 10 | 10 | 10 | 10 | 10 |

| Additional components in | Buffer 5 | Buffer 6 | | Buffer 7 | | Buffer 8 (KREBS) | |
|---|---|---|---|---|---|---|---|
| pH of the buffers | pH 7.4 | pH 6.0 | pH 7.4 | pH 6.0 | pH 7.4 | pH 6.0 | pH 7.4 |
| D-Glucose | 1.8 | 1.8 | 1.8 | 1.8 | 1.8 | 1.8 | 1.8 |
| Magnesium Chloride | 0.0468 | 0.0468 | 0.0468 | 0.0468 | 0.0468 | 0.0468 | 0.0468 |
| Potassium Chloride | 0.34 | 0.34 | 0.34 | 0.34 | 0.34 | 0.34 | 0.34 |
| Sodium Chloride | 7 | 7 | 7 | 7 | 7 | 7 | 7 |
| Sodium Phosphate Dibasic | 0. | 0.1 | 0.1 | 0.1 | 0.1 | 0.1 | 0.1 |
| Sodium Phosphate Monobasic | 0.18 | 0 | 0 | 0.18 | 0.18 | 0.18 | 0.18 |
| Sodium Bicarbonate | 1.26 | 1.26 | 1.26 | 0 | 0 | 1.26 | 1.26 |
| Lactic acid | 1 mM | 16 mM | 1 mM | 16 mM | 1 mM | 16 mM | 1 mM |
| 85A | 10 | 10 | 10 | 10 | 10 | 10 | 10 |

Some assay buffers based on PBS buffer with additional components were shown in Table 3 below. Note that the components in the buffers of Table 2 and 3 are presented as amount in grams added in one liter of buffer. But the concentration of human serum is 10 wt. % of the buffer.

TABLE 3

PBS Buffer Based Assay Buffers

| | Additional Component | | | |
|---|---|---|---|---|
| | Buffer 9 (PBS, commercial) | | Buffer 10 (PBS + NaHCO3) | |
| pH of buffers | pH 6.0 | pH 7.4 | pH 6.0 | pH 7.4 |
| KH2PO4 | 0.144 | 0.144 | 0.144 | 0.144 |
| NaCl | 9 | 9 | 9 | 9 |
| Na2HPO4 | 0.795 | 0.795 | 0.795 | 0.795 |
| Lactic acid | 16 mM | 1 mM | 16 mM | 1 mM |
| Sodium Bicarbonate | NA | NA | 1.26 | 1.26 |
| BSA | 10 | 10 | 10 | 10 |

The screening was carried out using an ELISA assay with these assay buffers. The ELISA assay was carried out as described in Examples 7-8. The selected conditionally active antibodies for each of the 10 assay buffers were presented in Table 4 below. The OD 450 absorbance is reversely correlated with the binding affinity in the ELISA assay.

TABLE 4

Selected Conditionally Active Antibodies (Mutants) Using Different Assay Buffers

| | OD 450 | Selected mutants | wild type |
|---|---|---|---|
| Buffer 1 | pH 6.0 | 0.859 | 1.6414 |
| | pH 7.4 | 0.0883 | 1.2474 |
| Buffer 2 | pH 6.0 | 0.6599 | 1.1708 |
| | pH 7.4 | 0.0717 | 1.1839 |
| Buffer 3 | pH 6.0 | 0.4806 | 0.7765 |
| | pH 7.4 | 0.0723 | 1.3497 |

TABLE 4-continued

Selected Conditionally Active Antibodies (Mutants) Using Different Assay Buffers

| | OD 450 | Selected mutants | wild type |
|---|---|---|---|
| Buffer 4 | pH 6.0 | 1.7364 | 1.7777 |
| | pH 7.4 | 0.4457 | 1.6173 |
| Buffer 5 | pH 6.0 | 0.6776 | 1.6905 |
| | pH 7.4 | 0.0747 | 1.3987 |
| Buffer 6 | pH 6.0 | 0.7244 | 1.4123 |
| | pH 7.4 | 0.0731 | 1.3439 |
| Buffer 7 | pH 6.0 | 0.6212 | 1.348 |
| | pH 7.4 | 0.8044 | 1.7381 |
| Buffer 8 | pH 6.0 | 0.7977 | 1.3893 |
| | pH 7.4 | 0.1042 | 1.5535 |
| Buffer 9 | pH 6.0 | 0.468 | 1.5087 |
| | pH 7.4 | 0.4455 | 1.347 |
| Buffer 10 | pH 6.0 | 0.5626 | 1.3439 |
| | pH 7.4 | 0.0727 | 1.2547 |

The selectivity of some of the selected conditionally active antibodies was confirmed using buffers 8 and 9 and it was found that they do have the desired selectivity in pH 6.0 over pH 7.4, as presented in FIG. 1. Note that using different buffers affected the selectivity of the conditionally active antibodies.

It must be noted that as used herein and in the appended claims, the singular forms "a", "an", and "the" include plural references unless the context clearly dictates otherwise. Furthermore, the terms "a" (or "an"), "one or more," and "at least one" can be used interchangeably herein. The terms "comprising," "including," "having," and "constructed from" can also be used interchangeably.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

It is to be understood that each component, compound, substituent or parameter disclosed herein is to be interpreted as being disclosed for use alone or in combination with one or more of each and every other component, compound, substituent or parameter disclosed herein.

It is also to be understood that each amount/value or range of amounts/values for each component, compound, substituent or parameter disclosed herein is to be interpreted as also being disclosed in combination with each amount/value or range of amounts/values disclosed for any other component(s), compounds(s), substituent(s) or parameter(s) disclosed herein and that any combination of amounts/values or ranges of amounts/values for two or more component(s), compounds(s), substituent(s) or parameters disclosed herein are thus also disclosed in combination with each other for the purposes of this description.

It is further understood that each range disclosed herein is to be interpreted as a disclosure of each specific value within the disclosed range that has the same number of significant digits. Thus, a range of from 1-4 is to be interpreted as an express disclosure of the values 1, 2, 3 and 4. It is further understood that each lower limit of each range disclosed herein is to be interpreted as disclosed in combination with each upper limit of each range and each specific value within each range disclosed herein for the same component, compounds, substituent or parameter. Thus, this disclosure to be interpreted as a disclosure of all ranges derived by combining each lower limit of each range with each upper limit of each range or with each specific value within each range, or by combining each upper limit of each range with each specific value within each range.

Furthermore, specific amounts/values of a component, compound, substituent or parameter disclosed in the description or an example is to be interpreted as a disclosure of either a lower or an upper limit of a range and thus can be combined with any other lower or upper limit of a range or specific amount/value for the same component, compound, substituent or parameter disclosed elsewhere in the application to form a range for that component, compound, substituent or parameter, All documents mentioned herein are hereby incorporated by reference in their entirety or alternatively to provide the disclosure for which they were specifically relied upon. The applicant(s) do not intend to dedicate any disclosed embodiments to the public, and to the extent any disclosed modifications or alterations may not literally fall within the scope of the claims, they are considered to be part hereof under the doctrine of equivalents.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

What is claimed is:

1. A method of selecting a conditionally active biologic protein, wherein the conditionally active biologic protein is a protein which exhibits a lower activity in an assay under a normal physiological condition compared to a same activity of the conditionally active biologic protein in an assay under an aberrant condition, the method comprising a step of:

selecting the conditionally active biologic protein from a library of wild-type proteins wherein the conditionally active biologic protein exhibits a lower activity in the assay under the normal physiological condition compared to the activity of the conditionally active biologic protein in the assay under the aberrant condition, wherein the assay under the normal physiological condition and the assay under the aberrant condition are performed in assay solutions containing at least one component at substantially the same concentration, said at least one component being selected from:

(a) an inorganic compound selected from boric acid, calcium chloride, di-ammonium phosphate, mono-ammonium phosphate, potassium sulfate, copper sulfate, iron sulfate, manganese sulfate, zinc sulfate, magnesium sulfate, calcium nitrate, calcium chelate, copper chelate, iron chelate, manganese chelate, zinc chelate, ammonium molybdate, ammonium sulphate, calcium carbonate, magnesium phosphate, potassium nitrate, hydrochloric acid, sulfuric acid, phosphoric acid, uric acid, and hydrogen chloride;

b. an ion selected from a phosphorus ion, a sulfuric ion, an ammonium ion, an iron ion, a zinc ion, a copper ion, a sulfate ion, a bisulfate ion, a carbonate ion, a bicarbonate ion, a nitrate ion, a nitrite ion, a persulfate ion, a monopersulfate ion, and a borate ion; and c. an organic molecule selected from amino acids, organic acids and sugars.

2. The method of claim 1, wherein the selecting step comprises selecting the conditionally active biologic protein which exhibits both: (a) a decrease in the activity in the assay under the normal physiological condition compared to a reference protein, and (b) an increase in the activity in the assay under the aberrant condition compared to the reference protein, wherein the reference protein has substantially the same activity in both the assay under the normal physiological condition and the aberrant condition.

3. The method of claim 1, wherein the wild-type proteins are wild-type antibodies.

4. The method of claim 1, wherein the wild-type protein library is a collection of proteins encoded by cDNAs.

5. The method of claim 1, wherein the wild-type protein library is a bacteriophage display library.

6. The method of claim 1, wherein the wild-type protein library is a collection of recombinant proteins.

7. The method of claim 1, wherein the selected conditionally active biologic protein is subjected to steps of:
  i. evolving DNA which encodes the selected conditionally active biologic protein using one or more evolutionary techniques to create mutant DNAs;
  ii. expressing the mutant DNAs to obtain mutant proteins; and
  iii. selecting an improved conditionally active biologic protein from the mutant proteins which exhibits both (a) a decrease in activity in the assay under the normal physiological condition compared to the selected conditionally active biologic protein, and (b) an increase in activity in the assay under the aberrant condition compared to the selected conditionally active biologic protein.

8. The method of claim 7, wherein the improved conditionally active biologic protein has an increased ratio of the activity in the assay under the aberrant condition to the activity under the normal physiological condition, as compared to the selected conditionally active biologic protein employed in step (i).

9. The method of claim 7, wherein the improved conditionally active biologic protein has one or more of an improved binding affinity, expression and humanization, as compared to the selected conditionally active biologic protein employed in step (i).

10. The method of claim 1 wherein the at least one component is a component that is present in a bodily fluid of a mammal and the at least one component is present in a normal physiological concentration.

11. The method of claim 1, wherein the at least one component is a component that is present in a bodily fluid of a mammal and has a concentration in the range of from about 5% to about 500% of the normal physiologic concentration.

12. The method of claim 1, wherein the at least one component is a component that is present in a bodily fluid of a mammal and has a concentration in the range of from about 75% to about 150% of the normal physiologic concentration.

13. The method of claim 1, wherein the at least one component comprises the inorganic compound.

14. The method of claim 1, wherein the at least one component comprises the ion and the ion is selected from ammonium ion, iron ion, zinc ion, and copper ion.

15. The method of claim 1, where the at least one component comprises one or more of uric acid in concentration range of 2-7.0 mg/dL, iron ion in a concentration range of 0.028-0.210 mg/dL, and carbonic acid in a concentration range of 15-30 mM.

16. The method of claim 1, wherein the at least one component comprises an organic molecule selected from the group consisting of an amino acid selected from Histidine, Alanine, Isoleucine, Arginine, Leucine, Asparagine, Lysine, Aspartic acid, Methionine, Cysteine, Phenylalanine, Glutamic acid, Threonine, Glutamine, Tryptophan, Glycine, Valine, Pyrrolysine, Proline, Selenocysteine, Serine, and Tyrosine.

17. The method of claim 1, wherein at least one component comprises an organic acid selected from the group consisting of citric acid, α-ketoglutaric acid, succinic acid, malic acid, fumaric acid, acetoacetic acid, β-hydroxybutyric acid, lactic acid, pyruvic acid, α-ketonic acid, acetic acid and volatile fatty acids.

18. The method of claim 1, wherein the at least one component comprises an organic molecule selected from the group consisting of glucose, pentose, hexose, xylose, ribose, mannose, galactose, lactose, GlcNAcβ1-3Gal, Galα1-4Gal, Manα1-2Man, GalNAcβ1-3Gal and O-, N-, C-, and S-glycosides.

19. The method of claim 1, wherein the ion is selected from sulfate ion, bisulfate ion, carbonate ion, bicarbonate ion, nitrate ion, nitrite ion, persulfate ion, monopersulfate ion and borate ion.

20. The method of claim 1, wherein the aberrant condition is a pH that is different from the normal physiological pH.

21. The method of claim 20, wherein the ion has a pKa that is within about 1 pH unit from the pH of the aberrant condition.

22. The method of claim 20, wherein the ion has a pKa that is within about 0.4 pH unit from the pH of the aberrant condition.

23. The method of claim 1, further comprising a step of evolving the selected conditionally active biologic protein to produce an improved conditionally active biologic protein with at least one improved property selected from binding affinity, expression level and humanization.

24. The method of claim 23, wherein the at least one improved property is an increased ratio of the activity in the assay under the aberrant condition to the activity under the normal physiological condition, as compared to the selected conditionally active biologic protein.

25. The method of claim 23, further comprising a step of conjugating the selected conditionally active protein to an agent selected from cytokines, interleukins, enzymes, hormones, growth factors, cytotoxic agents, chemotherapy drugs, radioactive particles and diagnostic agents.

26. The method of claim 1, wherein the protein is an antibody and further comprising a step of engineering the selected conditionally active antibody selected to be a bi-specific antibody.

27. The method of claim 1, wherein the protein is an antibody and further comprising a step of engineering the improved conditionally active antibody to be a bi-specific antibody to bind to both an immune effector cell surface antigen and a different target antigen and the immune effector cell is selected from a natural killer cell, a macrophage, a lymphokine-activated killer cell and a T-cell.

28. The method of claim 27, wherein the immune effector cell is a T-cell and the immune effector cell surface antigen is CD3.

29. The method of claim 1, wherein the protein is an antibody capable of binding an antigen of a diseased cell or diseased tissue.

30. The method of claim 1, further comprising the step of engineering the selected conditionally active biologic protein to include a cleavable moiety adapted to be cleaved from the conditionally active biologic protein when proximate to a diseased cell or diseased tissue.

31. The method of claim 1, wherein the assay solutions for the assay under the normal physiological condition and the assay under the aberrant condition contain no human serum.

32. The method of claim 1, wherein the at least one component comprises a component selected from the group consisting of urea, potassium bicarbonate and carbon dioxide.

* * * * *

UNITED STATES PATENT AND TRADEMARK OFFICE
CERTIFICATE OF CORRECTION

| | | |
|---|---|---|
| PATENT NO. | : 11,254,932 B2 | Page 1 of 1 |
| APPLICATION NO. | : 16/733358 | |
| DATED | : February 22, 2022 | |
| INVENTOR(S) | : Short et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 69 days.

Signed and Sealed this
Seventh Day of February, 2023

*Katherine Kelly Vidal*

Katherine Kelly Vidal
*Director of the United States Patent and Trademark Office*